US012709642B2

(12) United States Patent
Mannent et al.

(10) Patent No.: US 12,709,642 B2
(45) **Date of Patent: *Aug. 18, 2026**

(54) METHODS FOR TREATING NASAL POLYPOSIS BY ADMINISTERING AN IL-4R ANTAGONIST

(71) Applicants: Sanofi Biotechnology, Paris (FR); Regeneron Pharmaceuticals, Inc., Tarrytown, NY (US)

(72) Inventors: Leda Mannent, Paris (FR); Gianluca Pirozzi, Bridgewater, NJ (US); Allen Radin, Tarrytown, NY (US); Namita A. Gandhi, Tarrytown, NY (US); Robert Evans, Tarrytown, NY (US)

(73) Assignees: SANOFI BIOTECHNOLOGY, Gentilly (FR); REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/038,816

(22) Filed: Jul. 18, 2018

(65) Prior Publication Data

US 2019/0040146 A1 Feb. 7, 2019

Related U.S. Application Data

(63) Continuation of application No. 14/310,419, filed on Jun. 20, 2014, now Pat. No. 10,059,771.

(60) Provisional application No. 61/837,912, filed on Jun. 21, 2013.

(30) Foreign Application Priority Data

May 7, 2014 (EP) .................................... 14305670

(51) Int. Cl.

| | |
|---|---|
| ***A61K 39/395*** | (2006.01) |
| ***A61K 31/135*** | (2006.01) |
| ***A61K 31/136*** | (2006.01) |
| ***A61K 31/137*** | (2006.01) |
| ***A61K 31/167*** | (2006.01) |
| ***A61K 31/56*** | (2006.01) |
| ***A61K 31/58*** | (2006.01) |
| ***A61K 45/06*** | (2006.01) |
| ***A61P 11/00*** | (2006.01) |
| ***C07K 16/28*** | (2006.01) |
| *A61K 39/00* | (2006.01) |

(52) U.S. Cl.

CPC ........ *C07K 16/2866* (2013.01); *A61K 31/135* (2013.01); *A61K 31/136* (2013.01); *A61K 31/137* (2013.01); *A61K 31/167* (2013.01); *A61K 31/56* (2013.01); *A61K 31/58* (2013.01); *A61K 39/395* (2013.01); *A61K 39/3955* (2013.01); *A61K 45/06* (2013.01); *A61K 2039/505* (2013.01); *C07K 2317/21* (2013.01)

(58) Field of Classification Search

CPC ....................... A61K 39/3955; C07K 16/2866

See application file for complete search history.

(56) References Cited

U.S. PATENT DOCUMENTS

| | | | |
|---|---|---|---|
| 5,599,905 | A | 2/1997 | Mosley et al. |
| 5,714,146 | A | 2/1998 | Lewis et al. |
| 5,717,072 | A | 2/1998 | Mosley et al. |
| 5,856,296 | A | 1/1999 | Mosley et al. |
| 5,985,280 | A | 11/1999 | Ritter et al. |
| 6,156,877 | A | 12/2000 | Ritter et al. |
| 6,391,581 | B1 | 5/2002 | Mosley et al. |
| 6,548,655 | B1 | 4/2003 | Mosley et al. |
| 6,596,541 | B2 | 7/2003 | Murphy et al. |
| 6,716,587 | B2 | 4/2004 | Mosley et al. |
| 6,927,044 | B2 | 8/2005 | Stahl et al. |
| 7,141,653 | B2 | 11/2006 | Greenfeder et al. |
| 7,186,809 | B2 | 3/2007 | Pluenneke |
| 7,317,090 | B2 | 1/2008 | Mosley et al. |
| 7,422,742 | B2 | 9/2008 | Greenfeder et al. |
| 7,465,450 | B2 | 12/2008 | Pluenneke |
| 7,531,169 | B2 | 5/2009 | Singh et al. |
| 7,582,298 | B2 | 9/2009 | Stevens et al. |
| 7,605,237 | B2 | 10/2009 | Stevens et al. |
| 7,608,693 | B2 | 10/2009 | Marton et al. |
| 7,794,717 | B2 | 9/2010 | Stevens et al. |
| 8,030,003 | B2 | 10/2011 | Rothenberg |
| 8,075,887 | B2 | 12/2011 | Martin et al. |
| 8,075,897 | B2 | 12/2011 | Spertini et al. |
| 8,092,802 | B2 | 1/2012 | Stevens et al. |
| 8,092,804 | B2 | 1/2012 | Eriksson et al. |

(Continued)

FOREIGN PATENT DOCUMENTS

| | | | |
|---|---|---|---|
| AU | 2009231482 | A1 | 10/2009 |
| CA | 2737044 | A1 | 5/2010 |

(Continued)

OTHER PUBLICATIONS

Portolano et al., J. Immunol., 1993, vol. 150(3):880-887.*

(Continued)

*Primary Examiner* — Xiaozhen Xie

(74) *Attorney, Agent, or Firm* — LATHROP GPM LLP; James H. Velema, Esq.; Judith L. Stone-Hulslander

(57) ABSTRACT

The present invention provides methods for treating nasal polyposis. The methods include administering to a subject in need thereof a therapeutic composition comprising an interleukin-4 receptor (IL-4R) antagonist such as an anti-IL-4R antibody or antigen binding fragment thereof.

32 Claims, 1 Drawing Sheet

Specification includes a Sequence Listing.

(56) References Cited

U.S. PATENT DOCUMENTS 8,178,098 B2 5/2012 Lahn et al.
8,252,284 B2 8/2012 Singh et al.
8,324,192 B2 12/2012 Dohil et al.
8,337,839 B2 12/2012 Martin et al.
8,338,135 B2 12/2012 Stevens et al.
8,497,528 B2 7/2013 Lee et al.
8,604,171 B2 12/2013 Singh et al.
8,637,239 B2 1/2014 Furuta et al.
8,735,095 B2 5/2014 Martin et al.
8,945,559 B2 2/2015 Dix et al.
9,238,692 B2 1/2016 Dix et al.
9,415,015 B2 8/2016 Jacobi et al.
9,574,004 B2 2/2017 Ardeleanu et al.
9,864,091 B2 1/2018 Chen et al.
10,059,771 B2 8/2018 Mannent et al.
10,066,017 B2 9/2018 Mannent et al.
10,137,193 B2 11/2018 Pirozzi et al.
10,392,439 B2 8/2019 Stahl et al.
10,485,844 B2 11/2019 Radin
10,676,530 B2 6/2020 Stahl et al.
10,815,205 B2 10/2020 Collin-Kropelin et al.
11,034,768 B2 6/2021 Amin et al.
11,167,004 B2 11/2021 Radin et al.
11,214,621 B2 1/2022 Mannent et al.
11,292,847 B2 4/2022 Bansal et al.
11,485,788 B2 11/2022 Stahl et al.
11,771,743 B2 10/2023 Hamilton et al.
11,845,800 B2 12/2023 Ardeleanu et al.
11,866,503 B2 1/2024 Orengo et al.
11,964,016 B2 4/2024 Asrat et al.
12,090,201 B2 9/2024 Bansal et al.
12,398,212 B2 8/2025 Staudinger et al.
2002/0002132 A1 1/2002 Pluenneke et al.
2003/0103938 A1 6/2003 Jinquan et al.
2003/0113387 A1 6/2003 Tsuchida et al.
2003/0124121 A1 7/2003 Pluenneke
2005/0031609 A1 2/2005 Hultsch et al.
2005/0032164 A1 2/2005 Watson et al.
2005/0074462 A1 4/2005 Holmgren et al.
2005/0118176 A1 6/2005 Mosley et al.
2005/0255532 A1 11/2005 Ruben et al.
2005/0282181 A1 12/2005 Yan et al.
2006/0013811 A1 1/2006 Dina
2007/0041976 A1 2/2007 Pluenneke et al.
2007/0274996 A1 11/2007 Carter et al.
2008/0054606 A1 3/2008 Mitsuo et al.
2008/0160035 A1 7/2008 Stevens et al.
2009/0062168 A1 3/2009 Timar et al.
2009/0074793 A1 3/2009 Martin et al.
2009/0098142 A1 4/2009 Kassalan et al.
2009/0264392 A1 10/2009 Warndahl et al.
2010/0021476 A1 1/2010 Stevens et al.
2010/0047254 A1 2/2010 Martin et al.
2010/0144646 A1* 6/2010 Paterson ............ G01N 33/6893 514/1.1
2010/0291107 A1 11/2010 Stevens et al.
2011/0195500 A1 8/2011 Rothenberg
2012/0004205 A1 1/2012 Rothenberg
2012/0047954 A1 3/2012 Coppola et al.
2012/0052072 A1 3/2012 Martin et al.
2012/0088814 A1 4/2012 Gregory
2012/0097565 A1 4/2012 Dix et al.
2012/0135010 A1 5/2012 Stevens et al.
2012/0164080 A1 6/2012 Hill et al.
2012/0207815 A1 8/2012 Al.
2012/0240930 A1 9/2012 Kristensson et al.
2013/0052190 A1 2/2013 Pearce Collins et al.
2013/0078675 A1 3/2013 Martin et al.
2013/0324435 A1 12/2013 Rothenberg et al.
2014/0056920 A1 2/2014 Ardeleanu et al.
2014/0072583 A1 3/2014 Ardeleanu et al.
2014/0187523 A1 7/2014 Dohil et al.
2014/0271658 A1 9/2014 Murphy et al.
2014/0271681 A1 9/2014 Martin et al.
2015/0185228 A1 7/2015 Reisacher et al.
2015/0246119 A1 9/2015 Pirozzi et al.
2016/0102147 A1 4/2016 Dix et al.
2016/0185866 A1 6/2016 Mannent et al.
2018/0016343 A1 1/2018 Ardeleanu et al.
2018/0155436 A1 6/2018 Orengo et al.
2019/0040146 A1 2/2019 Mannent et al.
2019/0040147 A1 2/2019 Mannent et al.
2019/0078160 A1 3/2019 Dressen et al.
2019/0125865 A1 5/2019 Pirozzi et al.
2019/0169299 A1 6/2019 Amin
2019/0364622 A1 11/2019 Carlsson et al.
2019/0367622 A1 12/2019 Graham
2021/0000949 A1 1/2021 Goulaouic et al.
2021/0032354 A1 2/2021 Staudinger et al.
2021/0087284 A1 3/2021 Xu et al.
2021/0322546 A1 10/2021 Pirozzi et al.
2021/0380705 A1 12/2021 Amin et al.
2022/0169739 A1 6/2022 Xu et al.
2022/0204631 A1 6/2022 Mannent et al.
2023/0146317 A1 5/2023 Stjepanovic et al.
2023/0183362 A1 6/2023 Laws
2023/0340101 A1 10/2023 Haddad et al.
2024/0199751 A1 6/2024 Ardeleanu et al.
2024/0360232 A1 10/2024 Abdulai et al.
2025/0388685 A1 12/2025 Laws et al.

FOREIGN PATENT DOCUMENTS

CN 101522716 A 9/2009
CN 102046658 A 5/2011
CN 102197052 A 9/2011
CN 104755495 A 7/2015
CN 105517570 A 4/2016
CN 106232140 A 12/2016
CN 107206073 A 9/2017
EP 0 604 693 A1 7/1994
EP 0 367 566 A1 5/1997
EP 1 229 034 B1 4/2005
EP 1 113 818 B1 5/2006
EP 2 022 507 A1 2/2009
EP 1 527 100 B1 7/2009
EP 1 283 851 B1 3/2012
EP 2 888 281 A1 7/2015
EP 2970460 A2 1/2016
EP 3 010 539 A1 4/2016
EP 3 107 575 A1 12/2016
EP 3 218 412 A1 9/2017
EP 3 470 432 A1 4/2019
EP 3 613 432 A1 2/2020
EP 3703818 A1 9/2020
EP 3962515 A1 3/2022
JP H105-246874 A 9/1993
JP 2006-131623 A 5/2006
JP 2012-507294 A 3/2012
JP 2015-527364 A 9/2015
JP 2015-528576 9/2015
JP 2016-521713 A 7/2016
JP 6463351 B2 1/2019
NO 2017143270 A1 8/2017
RU 2162711 C2 2/2001
RU 2488595 C2 7/2013
RU 2674680 C2 12/2018
TW 201029664 A 8/2010
TW 201221141 A 6/2012
WO WO 1992/019259 A1 11/1992
WO WO 1994/014975 A1 7/1994
WO WO 2000/016804 A1 3/2000
WO 2001092340 A2 12/2001
WO 2002/007745 A1 1/2002
WO WO 2003/048083 A2 6/2003
WO WO 2003/085089 A2 10/2003
WO 2005047331 A2 5/2005
WO 2005085284 A1 9/2005
WO WO 2006/003407 A2 1/2006
WO 2006072564 A1 7/2006
WO WO 2006/083390 A2 8/2006
WO WO 2007/085815 A2 8/2007
WO 2008/054606 A2 5/2008
WO WO 2008/116165 A2 9/2008

(56) References Cited

FOREIGN PATENT DOCUMENTS

| | | | |
|---|---|---|---|
| WO | WO 2009/081201 A2 | 7/2009 | |
| WO | WO 2009/124954 A1 | 10/2009 | |
| WO | 2010053751 A1 | 5/2010 | |
| WO | WO 2010/065557 A2 | 6/2010 | |
| WO | 2010120524 A2 | 10/2010 | |
| WO | WO 2011/026966 A2 | 3/2011 | |
| WO | WO 2011/156000 A2 | 12/2011 | |
| WO | WO 2011/159821 A1 | 12/2011 | |
| WO | WO-2012047954 A1 * | 4/2012 | ............ A61M 5/315 |
| WO | WO 2012/094643 A2 | 7/2012 | |
| WO | WO 2012/177945 A2 | 12/2012 | |
| WO | WO 2013/051928 A1 | 4/2013 | |
| WO | WO 2013/066780 A2 | 5/2013 | |
| WO | 2013/088109 A1 | 6/2013 | |
| WO | WO 2013/155010 A1 | 10/2013 | |
| WO | 2014/031610 A1 | 2/2014 | |
| WO | 2014/039461 A1 | 3/2014 | |
| WO | WO 2014/059178 A1 | 4/2014 | |
| WO | WO 2014/164959 A2 | 10/2014 | |
| WO | WO 2014/031610 A8 | 11/2014 | |
| WO | 2014/197470 A1 | 12/2014 | |
| WO | 2014205365 A1 | 12/2014 | |
| WO | 2015006571 A1 | 1/2015 | |
| WO | 2015/127229 A1 | 8/2015 | |
| WO | 2016/077675 A1 | 5/2016 | |
| WO | WO 2017/143270 A1 | 8/2017 | |
| WO | 2018/057776 A1 | 3/2018 | |
| WO | WO 2018/045130 A1 | 3/2018 | |
| WO | WO 2018/102597 A1 | 6/2018 | |
| WO | WO 2018/190990 A1 | 10/2018 | |
| WO | WO 2019/028367 A1 | 2/2019 | |
| WO | WO 2019/089473 A1 | 5/2019 | |
| WO | WO 2019/224246 A1 | 11/2019 | |
| WO | WO 2020/096381 A1 | 5/2020 | |
| WO | WO 2020/135710 A1 | 7/2020 | |
| WO | WO 2020/223541 A1 | 11/2020 | |
| WO | WO 2021/011614 A1 | 1/2021 | |
| WO | WO 2021/119028 A1 | 6/2021 | |

OTHER PUBLICATIONS

Clackson et al., Nature, 1991, vol. 352:624-628.*

Knappik et al., J. Mol. Biol., 2000, vol. 296(1):57-86.*

Trangsrud et al., Pharmacotherapy, 2002, vol. 22(11):1458-1467 (abstract).*

Mendelsohn et al., Ann. Otol. Rhinol. Laryngol., 2011, vol. 120(3):162-166.*

Dellon Evan S. (2016) "19—A randomized, Double-Blind, Placebo-Controlled Trail of a Novel Recombinant, Humanized, Anti-Interleukin-13 Monoclonal Antibody (RPC4046) in Patients with Active Eosinophilic: Results of the HEROES Study," ACG 2016 Annual Scientific Meeting and PostGraduate Course, The Venetian Las Vegas NV, Oct. 14-19, 2016, 3 pages.

Ikuo Hirano et al. (2017) "Dupilumab Efficacy and Safety in Adult Patients With Active Eosinophilic Espophagitis: a Randomized Double-Blind Placebo-Controlled Phase 2 Trial," World Congress of Gastroenterology ACG 2017, Orlando Florida, Oct. 13-18, 2017, 20 pages.

Pesek et al. (2018) "Emerging drugs for eosinophilic esophagitis," Expert Opinion on Emerging Drugs, 23(2):173-183.

Rothenberg et al. (2015) "Intravenous anti-IL-13 mAb QAX576 for the treatment of eosinophilic esophagitis," J. Allergy Clin. Immunol., 135(2):500-507.

Collins et al. (May 2018) "Baseline Characteristics and Correlation Between Dysphagia and Disease Activity in Patients with Eosinophilic Esophagitis in a Randomized, Placebo-Controlled, Phase 2 Dupilumab Trial," Sa115 Abstract, AGA Abstract, p. S-259.

Ikuo Hirano et al. (May 2018) "Correlation between esophageal distensibility and objectivity measures of disease in patients with active eosinophilic esopagitis a post hoc analysis of a randomized, placebo-controlled, phase 2 dupilumab trial," Sa1113 Asbtract, AGA Abstract, p. S-244.

Al-Lazikani et al. (1997) "Standard conformations for the canonical structures of immunoglobulins," J. Mol. Biol. 273:927-948.

American Academy of Allergy, Asthma & Immunology. "Rhinitis (Hay Fever)" American Academy of Allergy, Asthma & Immunology. Accessible on the Internet at URL: http://www.aaaai.org/conditions-and-treatments/allergies/rhinitis. [Last Accessed May 7, 2016].

Angal et al. (1993) "A single amino acid substitution abolishes the heterogeneity of chimeric mouse/human (IgG4) antibody," Molecular Immunology. 30:105.

Borish et al. (2001) "Efficacy of soluble IL-4 receptor for the treatment of adults with asthma," J. Clin. Allergy Clin. Immunol. 107:963-970.

Brorson et al. (1999) "Mutational analysis of avidity and fine specificity of anti-levan antibodies," J. Immunol. 163:6694-6701.

Brummell et al. (1993) "Probing the combining site of an anti-carbohydrate antibody by saturation-mutagenesis: role of the heavy-chain CDR3 residues," Biochemistry. 32:1180-1187.

Burmeister-Getz et al. (2009) "Human Pharmacokinetics/Pharmacodynamics of an Interleukin-4 and Interleukin-13 Dual Antagonist in Asthma," J. Clin. Pharmacol. 49:1025-1036.

Cho et al. (Apr. 11, 2012) "Spontaneous Eosinophilic Nasal Inflammation in a Genetically-Mutant Mouse: Comparative Study with an Allergic Inflammation Model," PLoS One. 7(4):e35114. pp. 1-8.

Colman (1994) "Effects of amino acid sequence changes on antibody-antigen interactions," Research in Immunology. 145:33-36.

Figueiredo et al. (2008) "Inflammatory genes in nasal polyposis," Curr. Opin. Otolaryngol. Head Neck Surg. 16:18-21.

Frois et al. (2009) "Inhaled corticosteroids or long-acting beta-agonists alone or in fixed-dose combinations in asthma treatment: a systematic review of fluticasone/budesonide and formoterol/salmeterol," Clinical Therapeutics. 31(12):2779-2802.

Giembycz et al. (2008) "A Holy Grail of asthma management: toward understanding how long-acting beta(2)-adrenoceptor agonists enhance the clinical efficacy of inhaled corticosteroids," British Journal of Pharmacology.153:1090-1104.

Glare et al. (1999) "Asthmatic airway biopsy specimens are more likely to express the IL-4 alternative splice variant IL-4δ2," J. Allergy Clin. Immunol. 104:978-982.

Groves et al. (2007) "Inhibition of IL-4 and IL-13 with an IL-4 mutein (Aeroderm) protects against flares in atopic eczema," AERODERM in AD. Poster at St. John's Institute of Dermatology.

Grunewald et al. (1998) "An antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo," The Journal of Immunology. 160(8):4004-4009.

Jia et al. (Aug. 1, 2012) "Periostin is a systemic biomarker of eosinophilic airway inflammation in asthmatic patients," J. Allergy Clin. Immunol. 130:647-654.

Junitlla et al. (2008) "Tuning sensitivity to IL-4 and IL-13: differential expression of IL-4Ra, IL-13Ral, and Yc regulates relative cytokine sensitivity," J. Exp. Med. 205(11):2595-2608.

Kakkar et al. (2011) "Population PK and IgE Pharmacodynamic Analysis of a Fully Human Monoclonal Antibody Against IL4 Receptor," Pharmaceutical Research. 28(10):2530-2542.

KEGG: Kyoto Encyclopedia of Genes and Genomes. "Drug: D10354," Kegg Drug Entry No. D10354. Kanehisa Laboratories. Accessible on the Internet at URL: http://www.genomajp/dbget-bin/www_bget?dr:D10354. [Last Accessed on Jan. 12, 2016].

Kobayashi et al. (1999) "Tryptophan H33 plays an important role in pyrimidine (6-4) pyrimidone photoproduct binding by a high-affinity antibody," Protein Engineering. 12:879-844.

Kopf et al. (1993) "Disruption of the murine IL-4 gene blocks Th2 cytokine responses," Letters to Nature. 362:245-248.

Kostic et al. (2010) "A Fully Human IL4Ra Antibody for Inhibition of IL-4/IL-13-driven TH2 Responses in Allergic Disease," Clinical Immunology. 135:S105-S106.

Langer (1990) "New methods of drug delivery," Science. 249:1527-1533.

Lilly et al. (1999) "Elevated plasma eotaxin levels in patients with acute asthma," J. Allergy Clin. Immunol. 104:786-790.

(56) References Cited

OTHER PUBLICATIONS

Ludmila et al. (Feb. 3, 2014) "Poster 1013: IL-4R alpha antibody inhibits IgE production and airway remodeling in the mouse model of house dust mite-induced eosinophilic asthma," World Allergy Organization Journal. 7(1):P8.
Martin et al. (1989) "Modeling antibody hypervariable loops: a combined algorithm," Proc. Natl. Acad. Sci. USA. 86:9268-9272.
Mordenti et al. (1991) "Interspecies scaling of clearance and vol. of distribution data for five therapeutic proteins," Pharma. Res. 8:1351.
Morioka et al. (2009) "IL-4/IL-13 antagonist DNA vaccination successfully suppresses Th2 type chronic dermatitis," British Journal of Dermatology. 160(6):1172-1179.
National Heart, Lung, and Blood Institute (Nhlbi) (2007) "Quick Refernece Charts for the Classification and Stepwise Treatment of Asthma," 2 pgs.
Niranjan et al. (May 21, 2013) "Pathogenesis of allergen-induced eosinophilic esophagitis is independent of Interleukin (IL)-13," Immunology and Cell Biology. 91(6):408-415.
PUBCHEM Database [online] (Feb. 2, 2014) "CAS Registry No. 1190264-60-8," PubChem SID No. 172232447. National Center for Biotechnology Information. Accessible on the Internet at URL: http://pubchem.ncbi.nlm.nih.gov/substance/172232447#section=Top. [Mar. 14, 2016].
Sanofi With Regeneron Pharmaceuticals (Mar. 2, 2013) "Sanofi and Regeneron Report Positive Proof-of-Concept Data for Dupilumab, and IL-4R alpha Antibody, in Atopic Dermatitis." Presented at the 71st Annual Meeting of the American Academy of Dermatology. Accessibile on the Internet at URL: http://investor.regeneron.com/releasedetail.cfm?releaseid=744703.
Schmidt-Weber (Mar. 13, 2012) "Anti-IL-4 as a New Strategy in Allergy," Chem. Immunol. Allergy. 96:120-125.
Taylor et al. (1992) "A transgenic mouse that expresses a diversity of human sequence heavy and light chain mmunoglobulins," Nucl. Acids Res. 20:6287-6295.
Tazawa et al. (2004) "Relative importance of IL-4 and IL-13 in lesional skin of atopic dermatitis," Arch. Dermatol. Res. 295:459-464.
Walker et al. (1993) "Atopic dermatitis: correlation of peripheral blood T cell activation, eosinophilia and serum factors with clinical severity," Clinical and Experimental Allergy. 23:145-153.
Walker et al. (2008) "Use of Biologics as Immunotherapy in Asthma and Related Diseases," Expert Review of Clinical Immunology. 4(6):743-756.
Wenzel et al. (Apr. 27, 2016) "Dupilumab efficacy and safety in adults with uncontrolled persistent asthma despite use of medium-to-high-dose inhaled corticosteroids plus a long-acting beta2 agonist: a randomised double-blind placebo-controlled pivotal phase 2b dose-ranging trial," Lancet. 388:31-44.
Wils-Karp et al. (2008) "Untangling the Complex Web of IL-4 and IL-13 Mediated Signaling Pathways," Science Signaling. 1(51):1-5.
World Health Organization (Jan. 1, 2012) "International Nonproprietary Names for Pharmaceutical Substances (INN)," WHO Drug Information. 26(4):401-471.
Wu et al. (1987) "Receptor-mediated in vitro gene transformation by a soluble DNA carrier system," J. Biol. Chem. 262:4429-4432.
Zuo et al. (2010) "IL-13 Induced Esophageal Remodeling and Gene Expression by an Eosinophil-Independent, IL-13R {alpha} 2-Inhibited Pathway," Journal of Immunology. 185:660-669.
International Search Report with Written Opinion corresponding to International Patent Application No. PCT/US2015/016852, mailed May 11, 2015.
Small et al., J. Allergy Clin. Immunol., 2005, vol. 116:1275-1281.
Newton et al., Ther. Clin. Risk Manag., 2008, vol. 4(2):507-512.
Knappik et al., J. Mol. Bioi., 2000, vol. 296(1):57-86.
Clinical Trials, "History of Changes for Study: NCT01548404 Study of Dupilumab in Adult Patients With Extrinsic Moderate-to-Severe Atopic Dermatitis", U.S. National Library of Medicine, Retrieved at URL: https://clinicaltrials.gov/ct2/history/NCT01548404?V2=view#StudyPageTop.
Clinical Trials, History of Changes for Study: NCT01259323 Sequential Ascending Dose Study to Assess the Safety and Tolerability of REGN668 (SAR231893) in Patients With Atopic Dermatitis, U.S. National Library of Medicine, Retrieved at URL: https://clinicaltrials.gov/ct2/history/NCT01259323?V_5=View#StudyPageTop.
Regeneron Apr. 2011 Annual Report (12 pages).
Gevaert et al. (Nov. 2011) "Mepolizumab, a humanized anti-IL-5 mAb, as a treatment option for severe nasal bolyposis," J. Allergy Clin. Immunol. 128(5):989-995.
Gu et al. (Feb. 2011) "Expression and role of acidic mammalian chitinase and eotaxin-3 in chronic rhinosinusitis with nasal polyps," Journal of Otolaryngology-Head and Neck Surgery. 40(1):64-69.
Kimura et al. (Feb. 17, 2011) "Increased expression and role of thymic stromal lymphopoietin in nasal polyposis," Allergy Asthma Immunol. Res. 3(3):186-193.
Regeneron Pharmaceuticals, Inc. (Sep. 30, 2014) "Regeneron and Sanofi Announce Positive Phase 2 Top-Line Dupilumab Results in Patients with Chronic Sinusitis with Nasal Polyps," Acquire Media.
Schubert et al. (1998) "Evaluation and treatment of allergic fungal sinusitis. I. Demographics and diagnosis," J. Allergy Clin. Immunol. 102(3):387-394.
Schubert et al. (1998) "Evaluation and treatment of allergic fungal sinusitis. II. Treatment and follow-up," J. Allergy Clin. Immunol. 102(3):395-402.
Sheahan et al. (Feb. 2010) "Local IgE production in nonatopic nasal polyposis," Journal of Otolaryngology-Head and Neck Surgery. 39(1):45-51.
Van Zele et al. (2006) "Differentiation of chronic sinus diseases by measurement of inflammatory mediators," Allergy. 61:1280-1289.
Van Zele et al. (2010) "Oral steroids and doxycycline: two different approaches to treat nasal polyps," J. Allergy Clin. Immunol. 125(5):1069-1076.
Vlaminck et al. (May 2014) "The importance of local eosinophilia in the surgical outcome of chronic rhinosinusitis: a 3-year prospective observational study," Am. J. Rhinol. Allergy. 28(3):260-264.
Basic Local Alignment Search Tool. Search Results: "Alignment Heavy Chain Dupilumab with SEQ ID No. 9," National Center for Biotechnology Information. [Retrieved on Jan. 12, 2016].
Basic Local Alignment Search Tool. Search Results: "Alignment Heavy Chain Dupilumab with SEQ ID No. 10," National Center for Biotechnology Information. [Retrieved on Jan. 12, 2016].
International Search Report with Written Opinion corresponding to International Patent Application No. PCT/US2015/060540, mailed Feb. 17, 2016.
Bagnasco et al. (2016) "A Critical Evaluation of Anti-IL-13 and Anti-IL-4 Strategies in Severe Asthma," Int Arch Allergy Immunol;170; pp. 122-131.
Durham et al. (2016) "Targeted anti-inflammatory therapeutics in asthma and chronic obstructive lung disease," Translational Research, vol. 167, No. 1, pp. 192-203.
Romaniuk, L.I., "Allergan-specific immunotherapy: mechanisms, methods and efficacy," Clinical Immunology, Allergology and Infectology, 2012, special issue, pp. 44-47. (with English translation of the cited portion).
Regeneron Press Release, Nov. 22, 2013 "Sanofi and Regeneron Report Positive Results with Sarilumab In First Phase 3 Rheumatoid Arthritis Registration Trial," 3 pp.
Almagro et al. (2008) "Humanization of antibodies." Frontiers in Bioscience, 13, pp. 1619-1633.
Blauvelt et al. (2016) "Long-term management of moderate-to-severe atopic dermatitis with dupilumab and concomitant topical corticosteroids (Liberty Ad Chronos): a 1-year, randomised, double-blinded, placebo-controlled, phase 3 trial." The Lancet, Published online May 4, 2016 at www.thelancet.com (http://dx.doi.org/10.1016/S0140-6736(17)31191-1), 65 pp.
Hamilton et al. (2015) "Drug evaluation review: dupilumab in atopic dermatitis." Immunotherapy, 7 (10), 16 pp.
Martel et al. (2017) "Translational Animal Models of Atopic Dermatitis for Preclinical Studies." Yale Journal of Biology and Medicine, 90, 14 pp.
Oetjen et al. (2017) "Sensory Neurons Co-opt Classical Immune Signaling Pathways to Mediate Chronic Itch." Cell, 171, 26 pp.

(56) References Cited

OTHER PUBLICATIONS

Silverberg et al. (2017) "Dupilumab Treatment Rapidly Improves Itch in Patients With Moderate-to-Severe Atopic Dermatitis." Presented at the 75th Annual Scientific Meeting of the American College of Asthma, Allergy, and Immunology (ACAAI) 2017; Boston, MA, USA; Oct. 26-30, 2017, 1 pg.
Silverberg et al. (2017) "Dupilumab Treatment Induces Rapid Clinical Improvement of Itch in Patients With Moderate-to-Severe Atopic Dermatitis." Presented at the 76th American Academy of Dermatology Annual Meeting; San Diego, CA, USA; Feb. 16-20, 2018, 1 pg.
Simpson et al. (2016) "Two Phase 3 Trials of Dupilumab versus Placebo in Atopic Dermatitis." The New England Journal of Medicine, Downloaded from nejm.org on Sep. 30, 2016, 14 pp.
Barranco et al. (2017) "Dupilumab in the management of moderate-to-severe asthma," Therapeutics and Clinical Management, vol. 13, pp. 1139-1149.
Clinicaltrials.gov (Nov. 4, 2019) "Efficacy, Safety, and Tolerability of Dupilumab in Patients With Persisten Moderate to Severe Eosinophilic Asthma," [accessible on the internet at: https://clinicaltrials.gov/ct2/show/NCT01312961].
International Preliminary Report on Patentability corresponding to International Patent Application No. PCT/US2013/055747, issued Feb. 24, 2015.
Regeneron: "Highlights of Prescribing Information," https://www.regeneron.com/sites/default/files/Dupixent_FPI.pdf (Apr. 7, 2017), XP055534130.
Huang et al., " Severe Atopic Dermatitis in Children", Current Allergy and Asthma Reports, Current Science, US, vol. 18, No. 6, (May 10, 2018) pp. 1-8, XP036511794.
Akinlade et al., "Conjunctivitis in dupilumab clinical trials", British Journal of Dermatology, (Mar. 9, 2019) pp. 1-5, XP55610279.
Regeneron: "Dupixent: Highlights of Prescribing Information", https://d1egnxy4x1q3f.cloudfront.net/ Regeneron/Dupixent_FPI.pdf (Mar. 1, 2019) pp. 1-8, XP55610296.
Paller et al., " Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4, XP55610351.
Paller et al., "621 Dupilumab in adolescents with moderate-to-severe atopic dermatitis and a history of inadequate response, or intolerance to cyclosporine: subgroup analysis from a pivotal 16-week trial", XP002793332.
Cork, M.J., "605 Efficacy and safety of dupilumab in adolescent patients with moderate-to-severe atopic dermatitis", (May 1, 2019) XP002793331.
International Search Report dated Aug. 20, 2019 in related PCT Application No. PCT/US2019/031801 (19 pages).
International Search Report, PCT/US2013/055747, Dated Feb. 13, 2014. 8 pages.
Corren et al. 'A Randomized, Controlled, Phase 2 Study of AMG 317, an IL-4R Antagonist, in Patients with Asthma'. American Journal of Respiratory and Critical Care Medicine. 2010, vol. 181, No. 8, pp. 788-796.
Wenzel et al. 'ERS—Programme'. European Respiratory Society, Annual Congress 2010, pp. 3980.
Otulana et al. 'A Phase 2b Study of Inhaled Pitrakinra, an IL-4R/IL-13 Antagonist, Successfully Identified Responder Subpopulations of Patients with Uncontrolled Asthma'. American Journal of Respiratory and Critical Care Medicine. 2011, vol. 183, pp. A6179.
Slager et al. 'IL-4 Receptor Polymorphisms Predict Reduction in Asthma Exacerbations During Response to an AntiIL-4Receptor Antagonist'. Journal of Allergy and Clinical Immunology. 2012, vol. 130, No. 2, pp. 516-522.
Mrchow et al. 'Cellular and immunological markers of allergic and intrinsic bronchial asthma.' Lung. 1994, vol. 172, No. 6, pp. 313-334.
Bateman et al. 'Can guideline-defined asthma control be achieved? The Gaining Optimal Asthma Control study.' American journal of respiratory and critical care medicine. 2004. vol. 170, No. 8, pp. 836-844.
Sekiya et al. Increased levels of a TH2-type CC chemokine thymus and activation-regulated chemokine (TARC) in serum and induced sputum of asthmatics.' Allergy. 2002, vol. 57, No. 2, pp. 173-177.
Getz et al. 'Human Pharmacokinetics/Pharmacodynamics of an Interleukin-4 and Interleukin-13 Dual Antagonist in Asthma.' The Journal of Clinical Pharmacology. 2009, vol. 49, No. 9, pp. 1025-1036.
Davies et al. 'Affinity improvement of single antibody VH domains: residues in all three hypervariable regions affect antigen binding.' Immunotechnology. 1996, vol. 2, No. 3, pp. 169-179.
Gavett et al. 'Interleukin-4 receptor blockade prevents airway responses induced by antigen challenge in mice.' American Journal of Physiology-Lung Cellular and Molecular Physiology. 1997, vol. 16, No. 2, pp. L253.
Holt et al. 'Domain antibodies: proteins for therapy.' Trends in Biotechnology. 2003, vol. 21, No. 11, pp. 484-490.
Maliszewski et al. 'In Vivo Biological Effects of Recombinant Soluble Interleukin-4 Receptor.' Experimental Biology and Medicine. 1994, vol. 206, No. 3, pp. 233-237.
Oh et al. 'Investigational therapeutics targeting the IL-4/IL-13/STAT-6 pathway for the treatment of asthma.' European Respiratory Review. 2010, vol. 19, No. 115, pp. 46-54.
Sato et al. 'Recombinant soluble murine IL-4 receptor can inhibit or enhance IgE responses in vivo.' The Journal of Immunology. 1993, vol. 150, No. 7, pp. 2717-2723.
Tomkinson et al. 'A murine IL-4 receptor antagonist that inhibits IL-4-and IL-13-induced responses prevents antigen-induced airway eosinophilia and airway hyperresponsiveness.' The Journal of Immunology. 2001, vol. 166, No. 9, pp. 5792-5800.
Wenzel et al. 'Effect of an interleukin-4 variant on late phase asthmatic response to allergen challenge in asthmatic patients: results of two phase 2a studies.' The Lancet. 2007, vol. 370, No. 9596, pp. 1422-1431.
Arron et al. 'Peripheral biomarkers of an IL-13 induced bronchial epithelial gene signature in asthma.' Journal of Allergy and Clinical Immunology. 2009, vol. 179, No. 2, pp. A2536.
Woodruff et al. 'T-helper type 2-driven inflammation defines major subphenotypes of asthma.' American Journal of Respiratory and Critical Care Medicine. 2009, vol. 180, No. 5, pp. 388-395.
Zurawski et al. 'The primary binding subunit of the human interleukin-4 receptor is also a component of the Interleukin-13 receptor.' Journal of Biological Chemistry. 1995, vol. 270, No. 23, pp. 13869-13878.
Wenzel et al. 'Dupilumab in Persistent Asthma with Elevated Eosinophil Levels.' The New England Journal of Medicine. 2013, vol. 368, No. 26, pp. 2455-2466.
Sanofi with Regeneron Pharmaceuticals. 'An Evaluation of Dupilumab in Patients with Nasal Polyposis and Chronic Symptoms of Sinusitis.' Trial in Progress (Jun. 2014). ClinicalTrials.gov Identifier: NCT01920893 Retrieved from the Internet URL: http://clinicaltrials.gov/show/NCT01920893 Accessed on Sep. 29, 2014.
International Search Report and Written Opinion of the International Searching Authority, dated Oct. 6, 2014 (14 pages).
Bachert, Claus, et al. "Pharmacological management of nasal polyposis."Drugs 65.11 (2005): 1537-1552.
Molfino, N. A., et al. "Molecular and clinical rationale for therapeutic targeting of interleukin-5 and its receptor." Clinical & Experimental Allergy 42.5 (2012): 712-737.
Gevaert, Philippe, et al. "Nasal IL-5 levels determine the response to anti-IL-5 treatment in patients with nasal polyps." Journal of allergy and clinical immunology 118.5 (2006): 1133-1141.
Ezcano-Meza, D., et al. "Interleukin (IL)-4 and to a lesser extent either IL-13 or interferon-gamma regulate the production of eotaxin-2/CCL24 in nasal polyps. "Allergy 58.10 (2003): 1011-1017.
Scavuzzo, M. C., et al. "Inflammatory mediators and eosinophilia in atopic and non-atopic patients with nasal bolyposis." Biomedicine & pharmacotherapy 59.6 (2005): 323-329.
Hopkins, C., et al. "Psychometric validity of the 22-item Sinonasal Outcome Test." Clinical Otolaryngology 34.5 (2009): 447-454.

(56) References Cited

OTHER PUBLICATIONS

Hopkins, Claire, et al. "The Lund-Mackay staging system for chronic rhinosinusitis: How is it used and what does it predict?." Otolaryngology-Head and Neck Surgery 137.4 (2007): 555-561.
Akiyama et al. (1997) "[A study on indoor allergens measured in home environments of adult-asthmatic patients]," Housing Research Foundation. No. 24. Study No. 9620.—English Synopsis Only.
Bieber et al. (2012) "Atopic dermatitis: a candidate for disease-modifying strategy," Allergy. 67:969-975.
Burton et al. (2012) "Direct effects of IL-4 on mast cells drive their intestinal expansion and increase susceptibility to anaphylaxis in a murine model of food allergy," Mucosal Immunol. 6(4):740-50.
Dupixent Food and Drug Administration Label (Issued Mar. 2017) "Highlights of Prescribing Information (DUPIXENT), " Regeneron Pharmaceuticals, Inc.
Hong et al. (2011) "Management of Itch in Atopic Dermatitis," Semin. Cutan. Med. Surg. 30(2):71-86.
Vashkin et al. (2013) [Eosinophilic Esophagitis: A Training Manual for Doctors]. Moscow, Russia. pp. 13-21, 57-62.—provided with an English machine translation.
Mathias et al. (2011) "IgE-mediated systemic anaphylaxis and impaired tolerance to food antigens in mice with enhanced IL-4 receptor signaling," J. Allergy Clin. Immunol. 127(3):795-805.
Nadeau et al. (2012) "Oral Immunotherapy and Anti-IgE Antibody-Adjunctive Treatment for Food Allergy," Immunol Allergy Clin. North Am. 32(1):111-33.
Paton (Sep. 2017) "Dupilimab: human monoclonal antibody against IL-4Ralpha for moderate to severe atopic dermatitis," Drugs Today (Barc). 53(9):477-487.
Regeneron Pharmaceuticals, Inc. (May 21, 2013) "Sanofi and Regeneron Announce Publication of Positive Phase 2a Results of Dupilumab in Asthma in the New England Journal of Medicine," Press Release. Acquire Media, 3 pgs.
Saeki (2009) "Guidelines for management of atopic dermatitis," Advances in Medicine. Special Issue. 228(1):75-79.—English translation of the abstract only.
Simpson et al. (Jun. 4, 2016) "Dupilumab therapy provides clinically meaningful improvement in patient-reported outcomes (PROs): A phase IIb, randomized, placebo-controlled, clinical trial in adult patients with moderate to severe atopic dermatitis (AD)," J. Am. Acad. Dermatol. 75(3):506-515.
Simpson et al. (Jan. 14, 2016) "Patient burden of moderate to severe atopic dermatitis (AD): Insights from a phase Pb clinical trial of dupilumab in adults," J. Am. Acad. Dermatol. 74(3):491-498.
Terui et al. (2000) "[Learning from Fungus Allergy in Atopic Dermatitis Patients]," Jpn. J. Med. Mycol. 41(3):157-160.—English Abstract Only.
Thai et al. (Oct. 8, 2015) "Efficacy and safety of dupilumab in adults with moderate-to-severe atopic dermatitis nadequately controlled by topical treatments: a randomised, placebo-controlled, dose-ranging phase 2b trial," Lancet. 387(10013):40-52.
Tsianakas et al. (Oct. 8, 2015) "Dupilumab: a milestone in the treatment of atopic dermatitis," Lancet. 387 (10013):4-5.
Wang et al. (2010) "Peanut-induced intestinal allergy is mediated through a mast cell-IgE-FcepsilonRI-IL-13 pathway," J. Allergy Clin. Immunol. 126(2):306-316.
Wong et al. (Sep. 2017) "Guidelines for the management of atopic dermatitis (eczema) for pharmacists," Can. Pharm. J. (Ott). 150(5):285-297.
CORTES (Sep. 2009) "Proton pump inhibitors inhibit IL-4 and IL-13 signaling stat6 activation." Journal of Immunology, vol. 39, p. 5204.
Assa'ad (2011) "What is new in the treatment of eosinophilic eosophag it is?" From Food Allergy and Anaphylaxis Meeting 2011, Venice, Italy. Feb. 17-19, 2011, 1 pg.
Darveaux et al., (2015) "Biologics in Asthma—The Next Step Towards Personalized Treatment," J. Allergy Clin. Immunol. Pract., 3(2):152-161.
Extended European Search Report for European Patent Application No. 18194745.8, dated Jan. 16, 2019.
Meteran et al., (2017) "Novel monoclonal treatments in severe asthma," Journal of Asthma, 54(10):991-1011.
Shannon et al., (2008) "Differences in Airway Cytokine Profile in Severe Asthma Compared to Moderate Asthma," CHEST, 133(2):420-426.
Mueller et al. (2002) "Structure, binding, and antagonists in the IL-4/IL-13 receptor system," Biochimica et Biophysica Acta 1592, 237-250.
Ul-Haq et al. (2016) "Interleukin-4 receptor signaling and its binding mechanism: A therapeutic insight from inhibitors tool box," Cytokine and Growth Factor Reviews, 32:3-15.
Vakharia et al. (2017) "Monoclonal Antibodies for Atopic Dermatitis: Progress and Potential," BioDrugs, 31:409-422.
Anonymous, "Cas: PubChem: DRUG D10354-Dupilumab", Feb. 14, 2014, URL: http://www.genome.jp/dbget-bin/www_bget?dr:D10354, 2 pages.
Bachert et al., "Efficacy and safety of dupilumab in patients with severe chronic rhinosinusitis with nasal polyps (LIBERTY NP SINUS-24 and LIBERTY NP SINUS-52): results from two multicentre, randomised, double-blind, placebo-controlled, parallel-group phase 3 trials" The Lancet, 2019, vol. 394, pp. 1638-1650.
Chan et al., "Expression of Interleukin-4 in the Epidermis of Transgenic Mice Results in a Pruritic Inflammatory Skin Disease: An Experimental Animal Model to Study Atopic Dermatitis", The Journal of Investigative Dermatology, Oct. 2001, vol. 17, No. 4, pp. 977-983.
European Search Report in related European Application No. 19187112.8, dated Jan. 23, 2020, 13 pages.
Klementina et al., "Precision Medicine in Chronic Rhinosinusitis with Nasal Polyps", Current Allergy and Asthma Reports, vol. 18, No. 4, Mar. 24, 2018, 8 pages.
Marone et al., "The Intriguing Role of Interleukin 13 in the Pathophysiology of Asthma", Frontiers in Pharmacology, Dec. 6, 2009, vol. 10, Article 1387, 13 pages.
Naclerio et al., "Dupilumab Improves Sense of Smell and Reduces Anosmia Among Patients with nasal Polyposis and Chronic Sinusitis: Results from a Phase 2a Trial", Journal of Allergy and Clinical Immunology, vol. 139, No. 2, Abstract 286, Feb. 1, 2017, 1 page.
Nicodeme et al., "Esophageal Distensibility as a Measure of Disease Severity in Patients with Eosinophilic Esophagitis", Clin Gastroenterol Hepatol, Sep. 2013, vol. 11, No. 9, 14 pages.
Phan et al., "Assessment of Pruritus Intensity: Prospective Study on Validity and Reliability of the Visual Analogue Scale, Numerical Rating Scale in 471 Patients with Chronic Pruritis", Acta Derm Venereol, 2012, vol. 92, pp. 502-507.
Ring et al., "Guidelines for treatment of atopic eczema (atopic dermatits) Part I", JEADV, 2012, vol. 26, pp. 1045-4060.
Rizk et al., "Role of aspirin desensitization in the management of chronic rhinosinusitis", Current Opinion in Otolaryngology & Head and Neck Surgery, vol. 19, pp. 210-217.
Wegmann, "Targeting cytokines in asthma therapy: could IL-37 be a solution?", Expert Review of Respiratory Machine, 2017, vol. 11, No. 9, pp. 675-677.
WHO Drug Administration, International Non-Proprietary Names for Pharmaceutical Substances (INN) WHO Drug Information, vol. 26, No. 4, Jan. 2, 2012, URL: http://www.who.int/medicines/publications/druginformation/issues/PL_108.pdf, 71 pages.
Chan et al., "An update on the classifications, diagnosis, and treatment of rhinosinusitis", Current Opinion in Otolaryngology & Head and Neck Surgery, Jun. 2009, 17(3): 204-208.
Chin et al., "Nasal polyposis: an inflammatory condition requiring effective anti-inflammatory treatment", Current Opinion in Otolaryngology & Head and Neck Surgery, Feb. 2013, 21(1): 23-30.
International Nonproprietary Names for Pharmaceutical Substances (INN), WHO Drug Information, 2012, vol. 26, No. 4, obtained from url: https://www.who.int/medicines/publications/druginformation/issues/PL_108.pdf.
Kegg Drug: D10354, Dupilumab, originally retrieved on Aug. 16, 2019, obtained from url: https://www.genome.jp/dbget-bin/www_bget?dr:D10354.
Lange et al., "The Sino-Nasal Outcome Test 22 validated for Danish patients", Dan Med Bull., 2011, 58(2): A4235.

(56) References Cited

OTHER PUBLICATIONS

PubChem SID 172232447, Feb. 14, 2014, obtained from url: https://pubchem.ncbi.nlm.nih.gov/substance/172232447.
Wenzel et al., "Dupilumab in Persistent Asthma with Elevated Eosinophil Levels", New England Journal of Medicine, 2013, 368: 2455-2466.
Abonia, et al. (Apr. 2013) "High Prevalence of Eosinophilic Esophagitis in Patients with Inherited Connective Tissue Disorders", Journal of Allergy and Clinical Immunology, vol. 132, No. 2, pp. 378-386.
Aceves, et al. (Feb. 29, 2009) "Relationships Between Eosinophilic Inflammation, Tissue Remodeling and Fibrosis in Eosinophilic Esophagitis", Immunology and Allergy Clinics of North America, vol. 29, No. 1, pp. 197-211.
Akinlade et al. (2019) "Conjunctivities in dupilmab clinical trials," British Journal of Dermatology, Mar. 9, 2019, pp. 1-15.
Alving, et al. (1993) "Increased amount of nitric oxide in exhaled air of asthmatics", European Respiratory Journal, vol. 6, pp. 1368-1370.
"Annual Report 2013", Receptos Inc., Apr. 2013, 411 Pages.
Avdeeva, et al. (Apr. 2018) "Precision Medicine in Chronic Rhinosinusitis with Nasal Polyps", Current Allergy and Asthma Reports, vol. 18, No. 4, p. 25.
Ayars et al. (Mar. 13, 2012) "Pharmacologic Therapies in Pulmonology and Allergy", 2016 Med Clin N Am 100(4): 851-868.
Bachert, et al. (Sep. 19, 2019) "Efficacy and Safety of Dupilumab in Patients with Severe Chronic Rhinosinusitis with Nasal Polyps (LIBERTY NP SINUS-24 and LIBERTY NP SINUS-52): Results from Two Multicentre, Randomised, Double-Blind, Placebo-Controlled, Parallel-Group Phase 3 Trials", The Lancet, vol. 394, pp. 1638-1650.
Balint, et al. (Dec. 27, 1993) "Antibody Engineering by Parsimonious Mutagenesis", Gene, vol. 137, Issue 1, pp. 109-118.
Barnes, et al. (Nov. 3, 2008) "The Cytokine Network in Asthma and Chronic Obstructive Pulmonary Disease", The Journal of Clinical Investigation, vol. 118, No. 11, pp. 3546-3556.
Barthelemy, "Comprehensive analysis of the factors contributing to the stability and solubility of autonomous human VH domains", Journal of Biological Chemistry, 2008, 283:3639-3654.
Beiboer et al., "Guided selection of a pan carcinoma specific antibody reveals similar binding characteristics yet structural divergence between the original murine antibody and its human equivalent", Journal of Molecular Biology, 2000, 296:833-849.
Belikov, Pharmaceutical Chemistry, M., Higher School, 1993, p. 43-47.
Beyer, et al. (Apr. 2, 2002) "Human Milk-Specific Mucosal Lymphocytes of The Gastrointestinal Tract Display a Th2 Cytokine Profile", Journal of Allergy and Clinical Immunology, vol. 109, Issue 4, pp. 707-713.
Bhardwaj, et al. (Sep. 2012) "Biomarkers for Eosinophilic Esophagitis: A Review", Annals of Allergy, Asthma & Immunology, vol. 109, Issue 3, pp. 155-159.
Blanchard et al., (2006) "Eosinophilic esophagitis: Pathogenesis, genetics, and therapy," J. Allergy Clin. Immunol., 118:10549-9.
Blanchard, et al. (Apr. 2010) "Coordinate Interaction Between IL-13 and Epithelial Differentiation Cluster Genes in Eosinophilic Esophagitis", The Journal of Immunology, vol. 184, No. 7 (2010), pp. 4033-4041.
Blanchard, et al. (Aug. 24, 2005) "Inhibition of Human Interleukin-13-Induced Respiratory and Oesophageal Inflammation by Anti-Human-Interleukin-13 Antibody (CAT-354)", Clinical & Experimental Allergy, vol. 35, No. 8, pp. 1096-1103.
Blanchard, et al. (Dec. 2, 2007) "IL-13 Involvement in Eosinophilic Esophagitis: Transcriptome Analysis and Reversibility with Glucocorticoids", Journal of Allergy and Clinical Immunology, vol. 120, No. 6, pp. 1292-1300.
Blanchard, et al. (Feb. 2005) "Eotaxin-3 and a Uniquely Conserved Gene-Expression Profile in Eosinophilic Esophagitis", The Journal of Clinical Investigation, vol. 116, No. 2, pp. 536-547.
Blanchard, et al. (Feb. 2009) "Chemotactic Factors Associated with Eosinophilic Gastrointestinal Diseases", Immunology and allergy clinics of North America, vol. 29, No. 1, pp. 141-148.
Blanchard, et al. (Jan. 1, 2011) "A Striking Local Esophageal Cytokine Expression Profile in Eosinophilic Esophagitis", Journal of Allergy and Clinical Immunology, vol. 127, No. 1, pp. 208-217.
Blankestijn et al., "Could Duratumumab be used to treat severe allergy?", Journal of Allergy and Clinical Immunology, vol. 139, No. 5, Jan. 19, 2017, p. 1677-1678.e3.
Blauvelt et al. (Aug. 6, 2018) "Dupilumab does Not Affect Correlates of Vaccine-Induced Immunity: A Randomized, Placebo-Controlled Trial in Adults with Moderate-to-Severe Atopic Dermatitis", Journal of the American Academy of Dermatology, vol. 80, No. 1, p. 158.
Carr, Topical Calcineurin Inhibitors for Atopic Dermatitis: Review and Treatment Recommendations, Pediatric Drugs, 2013, vol. 15, pp. 303-310.
Carter, Paul J. (May 2006) "Potent Antibody Therapeutics by Design", Nature Reviews Immunology, vol. 6, No. 5, pp. 343-357.
Castro et al. (Jun. 28, 2018) "Dupilumab Efficacy and Safety in Moderate-to-Severe Uncontrolled Asthma", New England Journal of Medicine, vol. 378, No. 26, pp. 2486-2496.
Castro et al. (Nov. 1, 2018) "Dupilumab Efficacy and Safety in Uncontrolled, Moderate-to-Severe Allergic Asthma in the Phase 3 Liberty Asthma Quest Study", Annals of Allergy, Asthma and Immunology, p. S8.
Chan, et al. (Oct. 1, 2001) "Expression of Interleukin-4 in the Epidermis of Transgenic Mice Results in a Pruritic Inflammatory Skin Disease: An Experimental Animal Model to Study Atopic Dermatitis", Journal of Investigative Dermatology, vol. 117, No. 4, pp. 977-983.
Chehade, et al. (Feb. 2009) "The Role of Lymphocytes in Eosinophilic Gastrointestinal Disorders", Immunology and Allergy Clinics of North America, vol. 29, Issue 1, pp. 149-158.
Choi et al., "Predicting antibody complementarity determining region structures without classification", Molecular Biosystems, 2011, 7:3327-334.
Cleveland Clinic (Feb. 2017) "Nasal Polyps", Nasal Polyps: Symptoms, Causes, Prevention and Treatment, pp. 1-6.
ClinicalTrials.gov Identifier: NTC02407756, Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.
Colice, et al. (Aug. 2004) "Categorizing Asthma Severity: An Overview of National Guidelines", Clinical Medicine & Research, vol. 2, No. 3, pp. 155-163.
Cork et al., An open-label phase lla trial assessing the pharmacokinetics, safety and efficacy of dupilumab in a paediatric population with moderate-to-severe atopic dermatitis, P94, British Association of Dermatologists, Jul. 2017, 177 (Suppl. 1), pp. 25-77.
Corren (Jun. 6, 2020) "Effects of combined treatment with allergen immunotherapy and dupilumab on nasal allergen challenge and tolerability in immunotherapy", Allergy, p. 78.
Darsow et al., "Pruritus and Atopic Dermatitis", Clinic Rev Allerg Immunol (2011) 41:237-244.
Davis, et al. (Aug. 2004) "The Evolutionary and Structural 'Logic' of Antigen Receptor Diversity", Seminars in Immunology, vol. 16, Issue 4, pp. 239-243.
De Genst et al., "Antibody repertoire development in camelids", Developmental and Comparative Immunology, 30 (2006); 187-198.
Dellon, Evan S. (Apr. 27, 2013) "The Pathogenesis of Eosinophilic Esophagitis: Beyond the Eosinophil", Digestive Diseases and Sciences, vol. 58, pp. 1445-1448.
Desreumaux, et al. (Mar. 1, 1996) "Interleukin 3, Granulocyte-Macrophage Colony-Stimulating Factor, and Interleukin 5 in Eosinophilic Gastroenteritis", Gastroenterology, vol. 110, No. 3, pp. 768-774.
Djukanovic, et al. (2002) "Standardised Methodology of Sputum Induction and Processing", European Respiratory Journal, pp. 1S-2S.
Dupixent (dupilumab) Injection, for Subcutaneous Use, Patient Information, Issued Mar. 2017, 34 pages.

(56) References Cited

OTHER PUBLICATIONS

"Expert Panel Report 3: Guidelines for the Diagnosis and Management of Asthma", National Heart, Blood and Lung Institute, NIH, Aug. 28, 2007, 440 Pages.
Extended European Search Report received for European Application No. 19187112.8, mailed on Jan. 23, 2020, 13 Pages.
Fillon, et al. (2009) "Epithelial Function in Eosinophilic Gastrointestinal Diseases" Immunology and Allergy Clinics of North America, vol. 29, No. 1, pp. 171-178.
Foroughi, et al. (Sep. 1, 2007) "Anti-IgE Treatment of Eosinophil-Associated Gastrointestinal Disorders", Journal of Allergy and Clinical Immunology, vol. 120, Issue 3, pp. 594-601.
Franciosi, et al. (Feb. 2009) "Eosinophilic Esophagitis", Immunology and Allergy Clinics of North America, vol. 29, Issue 1, pp. 19-27.
Frieri, Marianne (Mar. 28, 2014) "Asthma Linked with Rhinosinusitis: An Extensive Review", Allergy & Rhinology (Providence), vol. 5, No. 1, pp. e41-e49.
Goodson, et al. (1984) "Dental Applications", Medical Applications of Controlled Release, vol. 2, pp. 115-138.
Green, et al. (2012) "Molecular Cloning: A Laboratory Manual", Cold Spring Harbor Laboratory Press, Fourth Edition, 34 Pages.
Griffiths et al., "Human anti-self antibodies with high specificity from phage display libraries", The EMBO Journal, 1993, 12:725-734.
HEALTHLINE website (Jan. 25, 2021) "Nasal Polyps", Nasal Polyps: Causes, Symptoms, and Diagnosis, pp. 1-11.
Hijnen, et al. (Feb. 2004) "Serum Thymus and Activation-Regulated Chemokine (TARC) and Cutaneous T Cell-Attracting Chemokine (CTACK) Levels in Allergic Diseases", Journal of Allergy and Clinical Immunology, vol. 113, No. 2, pp. 334-340.
"International Nonproprietary Names for Pharmaceutical Substances (Inn)", Who Drug Information records—World Health Organization, Jan. 1, 2014, pp. 379-422.
International Search Report with Written Opinion corresponding to International Patent Application No. PCT/US2020/042075, mailed Nov. 16, 2020.
Ivashkin, et al. (2012) "Eosinophilic Esophagitis: A Review of the Literature and a Description of its Own Observation", FUGHC, vol. 22, No. 1, Available at: <<RZHGGK online—www.gastro-j.ru>>, pp. 71-81.
Jahnz-Rozyk, et al. (Apr. 6, 2005) "Serum Thymus and Activation-Regulated Chemokine, Macrophage-Derived Chemokine and Eotaxin as Markers of Severity of Atopic Dermatitis", Allergy, vol. 60, No. 5, pp. 685-688.
Jakubke et al., "Amino acids, peptides and proteins", Martin-Luther-Universität Halle-Wittenberg, 1977 The Macmillan Press Ltd. doi 10.1007/978-1-349-02503.
Jakubke, et al. (1985) "Amino Acids, Peptides, Proteins", M: Mir, pp. 92-94.
Jyonouchi, et al. (2013) "Invariant Natural Killer T cells in children with Eosinophilic Esophagitis", Basic Mechanisms in Allergic Disease, Clinical & Experimental Allergy, vol. 44, No. 1, pp. 58-68.
Kagami, et al. (2003) "Significant Elevation of Serum Levels of Eotaxin-3/CCL26, but not of Eotaxin-2/CCL24, in Patients with Atopic Dermatitis: Serum Eotaxin-3/CCL26 Levels Reflect the Disease Activity of Atopic Dermatitis", Clinical & Experimental Immunology, vol. 134, No. 2, pp. 309-313.
Kakinuma, et al. (2002) "Serum Macrophage-Derived Chemokine (MDC) Levels are Closely Related with the Disease Activity of Atopic Dermatitis", Clinical & Experimental Immunology, vol. 127, No. 2, pp. 270-273.
Kakinuma, et al. (Mar. 1, 2001) "Thymus and Activation-Regulated Chemokine in Atopic Dermatitis: Serum Thymus and Activation-Regulated Chemokine Level is Closely Related with Disease Activity", Journal of Allergy and Clinical Immunology, vol. 107, No. 3, pp. 535-541.
Katial, Rohit (Feb. 2009) "Biomarkers for Nononcologic Gastrointestinal Diseases", Immunology and Allergy Clinics of North America, vol. 29, Issue 1, pp. 119-127.
Kim, et al. (Dec. 1, 2004) "Rebound Eosinophilia after Treatment of Hypereosinophilic Syndrome and Eosinophilic Gastroenteritis with Monoclonal Anti-IL-5 Antibody SCH55700", Journal of Allergy and Clinical Immunology, vol. 114, No. 6, pp. 1449-1455.
Klementina, et al. (Mar. 24, 2018) "Precision Medicine in Chronic Rhinosinusitis with Nasal Polyps", Allergy and Asthma Reports, vol. 18, No. 4, 8 Pages.
Klimka et al., "Human anti-CD30 recombinant antibodies by guided phage antibody selection using cell panning", British Journal of Cancer, 2000, 83:252-260.
Konikoff, et al. (Nov. 1, 2006) "A Randomized, Double-Blind, Placebo-Controlled Trial of Fluticasone Propionate for Pediatric Eosinophilic Esophagitis", Gastroenterology, vol. 131, No. 5, pp. 1381-1391.
Kopp et al., (2009) "Combination of omalizumab and specific immunotherapy is superior to immunotherapy in patients with seasonal allergic rhinoconjunctivitis and co-morbid seasonal allergic asthma," Clinical and Experimental Allergy, 39:271-279.
Kottyan, et al. (Aug. 2014) "Genome-Wide Association Analysis of Eosinophilic Esophagitis Provides Insight into the Tissue Specificity of this Allergic Disease", Nature Genetics, vol. 46, No. 8, pp. 895-900.
Kroegel, et al. (May 2009) "Global Initiative for Asthma (GINA) guidelines: 15 Years of Application", Expert Review of Clinical Immunology, vol. 5, No. 3, pp. 239-249.
Kulis, et al. (Nov. 19, 2010) "Single-Tree Nut Immunotherapy Attenuates Allergic Reactions in Mice with Hypersensitivity to Multiple Tree Nuts", Journal of Allergy and Clinical Immunology, vol. 127, No. 1, pp. 81-88.
Leung, et al. (Apr. 2004) "New Insights into Atopic Dermatitis", The Journal of Clinical Investigation, vol. 113, No. 5, pp. 651-657.
Leung, et al. (Mar. 13, 2003) "Effect of Anti-IgE Therapy in Patients with Peanut Allergy", New England Journal of Medicine, vol. 348, No. 11, pp. 986-993.
Liacouras, et al. (Apr. 8, 2011) "Eosinophilic Esophagitis: Updated Consensus Recommendations for Children and Adults", Journal of Allergy and Clinical Immunology, vol. 128, No. 1, pp. 3-20.
Liu, et al. (Aug. 9, 1999) "Hydrodynamics-Based Transfection in Animals by Systemic Administration of Plasmid DNA", Gene Therapy, vol. 6, No. 7, pp. 1258-1266.
Lommatzsch et al. (Dec. 12, 2014) "Severe Asthma Definiteion, Diagnosis and Treatment", Deutsches Arzteblatt International Feb. 2013, vol. 111, No. 50, pp. 847-855.
Lucendo, et al. (Nov. 1, 2012) "Adult Versus Pediatric Eosinophilic Esophagitis: Important Differences and Similarities for the Clinician to Understand", Expert Review of Clinical Immunology, vol. 8, No. 8, pp. 733-745.
Lwin, et al. (Apr. 2011) "Eosinophilic Gastritis: Histopathological Characterization and Quantification of the Normal Gastric Eosinophil Content", Modern Pathology, vol. 24, No. 4, pp. 556-563.
Mannon, et al. (2012) "Interleukin 13 and its Role in Gut Defence and Inflammation", Gut, vol. 61, No. 12, pp. 1765-1773.
Marone, et al. (Dec. 6, 2013) "The Intriguing Role of Interleukin 13 in the Pathophysiology of Asthma", Frontiers in Pharmacology, vol. 10, pp. 1-13.
Mashovsky (2001) Moscow, 2001 Medicines, 14th edition, v1:8-9.
Masterson, et al. (Oct. 2011) "Update on Clinical and Immunological Features of Eosinophilic Gastrointestinal Diseases", Current Opinion in Gastroenterology, vol. 27, No. 6, pp. 515-522.
Mayo Clinic (Jan. 25, 2021) "Nasal Polyps", Nasal Polyps—Symptoms and Causes, pp. 1-4.
Mishra, et al. (Jan. 1, 2001) "An Etiological Role for Aeroallergens and Eosinophils in Experimental Esophagitis", The Journal of Clinical Investigation, vol. 107, No. 1, pp. 83-90.
Mishra, et al. (Mar. 1, 2002) "IL-5 Promotes Eosinophil Trafficking to the Esophagus", The Journal of Immunology, vol. 168, No. 5, pp. 2464-2469.
Mishra, et al. (Nov. 1, 2003) "Intratracheal IL-13 Induces Eosinophilic Esophagitis by an IL-5, Eotaxin-1, and STAT6-Dependent Mechanism", Gastroenterology, vol. 125, No. 5, pp. 1419-1427.
Naclerio, et al. (Feb. 1, 2017) "Dupilumab Improves Sense of Smell and Reduces Anosmia Among Patients with Nasal Polyposis and

(56) References Cited

OTHER PUBLICATIONS

Chronic Sinusitis: Results from a Phase 2a Trial", Journal of Allergy and Clinical Immunology, vol. 139, No. 2, AB90, 1 Page.
Nadeau, et al. (Jun. 2011) "Rapid Oral Desensitization in Combination with Omalizumab Therapy in Patients with Cow's Milk Allergy", The Journal of Allergy and Clinical Immunology, vol. 127, No. 6, pp. 1622-1624.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
Nguyen, et al. (Jul. 2011) "Immune Modulation for Treatment of Allergic Disease", Immunological Reviews, vol. 242, No. 1, pp. 258-271.
Nicodeme, et al. (Sep. 2013) "Esophageal Distensibility as a Measure of Disease Severity in Patients with Eosinophilic Esophagitis", Clinical Gastroenterology and Hepatology, vol. 11, No. 9, pp. 1101-1107.
Niederberger, Verena (Feb. 2009) "Allergen Specific Immunotherapy", Immunology Letters, vol. 122, Issue 2, pp. 131-133.
Noel, et al. (Aug. 24, 2006) "Eosinophilic Esophagitis", The New England Journal of Medicine, vol. 351, pp. 940-941.
Novartis Pharmaceuticals (2013) "A Double Blinded, Randomized, Placebo-Controlled Trial of Intravenous QAX576 in the treatment of Eosinophilic Esophagitis", QAX576.
Ohno, et al. (May 1, 1985) "Antigen-Binding Specificities of Antibodies are Primarily Determined by Seven Residues of VH", Proceedings of the National Academy of Sciences, vol. 82, No. 9, pp. 2945-2949.
Ong, Peck Y. (2012) "Editorial Update on Emerging Treatments of Atopic Dermatitis", Expert Opinion on Emerging Drugs, vol. 17, No. 2, pp. 129-133.
Otani, et al. (Apr. 29, 2013) "Anti-IL-5 Therapy Reduces Mast Cell and IL-9 Cell Numbers in Pediatric Patients with Eosinophilic Esophagitis", Journal of Allergy and Clinical Immunology, vol. 131, Number 6, pp. 1576-1582.
Oyoshi, et al. (Jan. 1, 2009) "Cellular and Molecular Mechanisms in Atopic Dermatitis", Advances in Immunology, vol. 102, pp. 135-226.
Peserico, et al. (2008) "Reduction of Relapses of Atopic Dermatitis with Methylprednisolone Aceptonate Cream Twice Weekly in Addition to Maintenance Treatment with Enrollment: A Multicentre, Randomized, Double-Blind, Controlled Study", British Journal of Dermatology, vol. 158, No. 04, pp. 801-807.
Phan, et al. (2012) "Assessment of Pruritus Intensity: Prospective Study on Validity and Reliability of the Visual Analogue Scale, Numerical Rating Scale and Verbal Rating Scale in 471 Patients with Chronic Pruritus", Acta Dermato-Venereologica, vol. 92, pp. 449-581.
Powell, et al. (Sep.-Oct. 1998) "Compendium of Excipients for Parenteral Formulations", PDA Journal of Pharmaceutical Science and Technology, vol. 52, No. 5, pp. 238-311.
Prieto, et al. (May 24, 2013) "Eosinophilic Esophagitis in Adults: An Update on Medical Management", Current Gastroenterology Reports, vol. 15, No. 6, p. 324.
Prussin, et al. (Dec. 1, 2009) "Eosinophilic Gastrointestinal Disease and Peanut Allergy are Alternatively Associated with IL-51 and IL-5—TH2 Responses", Journal of Allergy and Clinical Immunology, vol. 124, No. 6, pp. 1326-1332.
Rafi, et al. (Jan. 1, 2010) "Effects of Omalizumab in Patients with Food Allergy", In Allergy & Asthma Proceedings, vol. 31, No. 1, pp. 76-83.
Rayapudi (Aug. 2010) "Indoor insect Allergens are Potent Inducers of Experimental Eosinophilic Esophagitis in Mice", Journal of Leukocyte Biology, vol. 88, No. 2, pp. 337-346.
Regeneron Pharmaceuticals (Oct. 16, 2017) "Regeneron and Sanofi Announce Positive Phase 2 Study Results for Dupilumab in Patients Active Moderate'-to-severe Eosinophilic Esophagitis", Acquire Media, 4 Pages.
Regeneron Pharmaceuticals et al. (Jun. 26, 2019) "Dupilumab as an Adjunct for Subcutaneous Grass Immunotherapy", retrieved from Internet at: https://clinicaltrials.gov/ct2/history/NCT03558997?A=4&B=4&C=merged#StudyPageTop, retrieved on Oct. 20, 2020, 10 pgs.
Regeneron Pharmaceuticals et al. (May 11, 2020) "Dupilumab As An Adjunct for Subcutaneous Grass Immunotherapy", retrieved from Internet at: https://clinicaltrials.gov/ct2/history/NCT03558997?V_5=View#StudyPageTop, retrieved on Oct. 20, 2020, 46 pgs.
Regeneron Pharmaceuticals, Apr. 2011 Annual Report (12 pages).
Ring, et al. (2012) "Guidelines for Treatment of Atopic Eczema Part I", Journal of the European Academy of Dermatology and Venereology, vol. 26, pp. 1045-1060.
Rizk, Habib (2011) "Role of Aspirin Desensitization in the Management of Chronic Rhinosinusitis", Current Opinion in Otolaryngology & Head and Neck Surgery, vol. 19, Issue 3, pp. 210-217.
Roitt, et al. (2001) "Immunology—Sixth Edition", Mosby—Harcourt Publishers Limited, pp. 110-111.
Roll, et al. (Jan. 1, 2006) "Safety of Specific Immunotherapy using a Four-Hour Ultra-Rush Induction Scheme in Bee and Wasp Allergy", Journal of Investigational Allergology and Clinical Immunology, vol. 16, No. 2, pp. 79-85.
Rothenberg, Marc E. (Jan. 1, 2004) "Eosinophilic Gastrointestinal Disorders (EGID)", Journal of Allergy and Clinical Immunology, vol. 113, No. 1, pp. 11-28.
Rothenberg, Marc E. (Oct. 2009) "Eosinophilic Esophagitis: Biology to Therapy", Gastroenterology, vol. 137, No. 4, pp. 1238-1249.
Sampson, et al. (May 2011) "A Phase II, Randomized, Double-Blind, Parallel-Group, PlaceboOcontrolled Oral Food Challenge Trial of Xolair (Omalizumab) in Peanut Allergy", The Journal of Allergy and Clinical Immunology, vol. 127, No. 5, pp. 1309-1310. e1.
SANOFI (43671) "A Controlled Clinical Study of Dupilumab in Patients with Bilateral Nasal Polyps (SINUS-24)", ClinicalTrials.gov Identifier: NCT02912468, 18 Pages.
SANOFI (May 18, 2020) "Evaluation of SAR440340 and as Combination Therapy with Dupilumab in Moderate-to-Severe Asthma Participants", Clinical Trials Accession No. NCT03387852, Retrieved from: <<https://clinicaltrials.gov/ct2/show/NCT03387852>>, 10 Pages.
SANOFI (Oct. 19, 2018) "Evaluation of Dupilumab in Patients with Severe Steroid Dependent Asthma (VENTURE)", Archive History for NCT02528214, Retrieved at URL: <<https://clinicaltrials.gov/ct2/history/NCT02528214?V_38=View#StudyPageTop>>, 15 Pages.
SANOFI (Oct. 23, 2019) "Controlled Clinical Study of Dupilumab in Patients with Nasal Polyps (SINUS-52)", ClinicalTrials.gov Identifier: NCT02898454, 18 Pages.
Sanofi, Clinical Trials, "History of Changes for Study: NCT01259323 Sequential Ascending Dose Study to Assess the Safety and Tolerability of REGN668 (SAR231893) in Patients With Atopic Dermatitis,", U.S. National Library of Medicine, Retrieved at URL: https://clinicaltrials.gov/ct2/history/NCT01259323?V_5=View#StudyPageTop.
Sanofi, Clinical Trials, "History of Changes for Study: NCT01548404 Study of Dupilumab in Adult Patients With Extrinsic Moderate-to_ Severe Atopic Dermatitis", U.S. National Library of Medicine, Retrieved at URL: https://clinicaltrials.gov/ct2/history/NCT01548404?V2=view#StudyPageTop.
Sanofi, Clinicaltrials.Gov (Nov. 4, 2019) "Efficacy, Safety, and Tolerability of Dupilumab in Patients With Persisten Moderate to Severe Eosinophilic Asthma," [accessible on the internet at: https://clinicaltrials.gov/ct2/show/NCT01312961].
Schmidt, (Feb. 2011) "Basophil Sensitivity Decreases During the Updosing on SCIT in Subjects Allergic to Grass Pollen", Journal of Allergy and Clinical Immunology, vol. 127, No. S2, p. AB203.
Schmidt, J J. (1985) "DNA Cloning: A Practical Approach vols. I and II", Edited by D M Glover, IRL Press Oxford, 1 Page.
Schmitt, et al. (Dec. 1, 2007) "What are the Best Outcome Measurements for Atopic Eczema? A Systematic Review", Journal of Allergy and Clinical Immunology, vol. 120, No. 6, pp. 1389-1398.
Schneider, et al. (Dec. 1, 2002) "A Pilot Study of Omalizumab to Facilitate Rapid Oral Desensitization in High-Risk Peanut-Allergic Patients", Journal of Allergy and Clinical Immunology, vol. 132, No. 6, pp. 1368-1374.

(56) References Cited

OTHER PUBLICATIONS

"Section 3, The Four Components of Asthma Management", Guidelines for the Diagnosis and Management of Asthma, Aug. 28, 2007, 1 Page.
Sefton, MV (Jan. 1, 1987) "Implantable Pumps", Critical Reviews in Biomedical Engineering, vol. 14, No. 3, pp. 201-240.
Sigfried et al., (2019) "Use of Dupilimab in pediatric atopic dermatits: Access, dosing, and implications for managing severe atopic dermatits", Pediatric Dermatology, 36: 172-176.
Sriaroon et al. (Aug. 17, 2014) "Biological Modulators in Eosinophilic Diseases", Clinical Reviews in Allergy and Immunology, vol. 50, No. 2, pp. 252-272.
Stein, et al. (Dec. 1, 2006) "Anti-IL-5 (Mepolizumab) Therapy for Eosinophilic Esophagitis", Journal of Allergy and Clinical Immunology, vol. 118, No. 6, pp. 1312-1319.
Stone, et al. (Dec. 2008) "Immunomodulatory Therapy of Eosinophil- Associated Gastrointestinal Diseases", Clinical & Experimental Allergy, vol. 38, No. 12, pp. 1858-1865.
Straumann, et al. (Dec. 1, 2001) "Idiopathic Eosinophilic Esophagitis is Associated with a TH2-Type Allergic Inflammatory Response", Journal of Allergy and Clinical Immunology, vol. 108, No. 6, pp. 954-961.
Straumann, et al. (Feb. 1, 2005) "Eosinophilic Esophagitis: Escalating Epidemiology?", Journal of Allergy and Clinical Immunology, vol. 115, 2, pp. 418-419.
Straumann, et al. (Feb. 1, 2009) "Clinical Evaluation of the Adult who has Eosinophilic Esophagitis", Immunology and Allergy Clinics of North America, vol. 29, No. 1, pp. 11-18.
Straumann, et al. (Jan. 1, 2010) "Anti-Interleukin-5 Antibody Treatment (Mepolizumab) in Active Eosinophilic Oesophagitis: A Randomised, Placebo-Controlled, Double-Blind Trial", Gut, vol. 59, No. 1, pp. 21-30.
Straumman et al. (2008) "Anti-TNF-a (infliximab) therapy for severe adult eosinophilic esophagitis," J. Allergy Clin. Immunol., 122(2):425-427.
Tang, et al. (2010) "YKL-40 in Asthmatic Patients, and its Correlations with Exacerbation, Eosinophils and Immunoglobulin E", European Respiratory Society, vol. 35, pp. 757-760.
Tsubouchi et al. (Jan. 1, 2019) "Successful Treatment with Mepolizumab in a Case of Allergic Bronchopulmonary Aspergillosis Complicated with Nontuberculosis Mycobacterial Infection" Respiratory Medicine CME, vol. 28.
Veerappan, et al. (Apr. 1, 2009) "Prevalence of Eosinophilic Esophagitis in an Adult Population Undergoing Upper Endoscopy: A Prospective Study", Clinical Gastroenterology and Hepatology, vol. 7, No. 4, pp. 420-426.
Vestergaard, et al. (Oct. 1, 2000) "A Th2 Chemokine, TARC, Produced by Keratinocytes May Recruit CLA+CCR4+ Lymphocytes into Lesional Atopic Dermatitis Skin", Journal of Investigative Dermatology, vol. 115, No. 4, pp. 640-646.
Wang, et al. (Dec. 1, 2008) "The IIL-17 Cytokine Family and their Role in Allergic Inflammation", Current Opinion in Immunology, vol. 20 Number, pp. 697-702.
Ward et al., Binding activities of a repertoire of single immunoglobin variable domains secreted from *Escherichia coli*, Nature, 1989, 341 :544-546.
Wark, et al. (Aug. 7, 2006) "Latest Technologies for the Enhancement of Antibody Affinity", Advanced Drug Delivery Reviews, vol. 58, No. 5-6, pp. 657-670.
Weber, et al. (Mar. 13, 2012) "Anti-IL-4 as a New Strategy in Allergy", Chemical immunology and Allergy, vol. 96, pp. 120-125.
Wegmann, et al. (2017) "Targeting Cytokines in Asthma Therapy: Could IL-37 be a Solution?", Expert Review of Respiratory Medicine, vol. 11, No. 9, pp. 675-677.
Weihrauch, et al. (Jul. 1, 2005) "Elevated Serum Levels of CC Thymus and Activation-Related Chemokine (Tarc) in Primary Hodgkin's Disease: Potential for a Prognostic Factor", Cancer Research, vol. 65, No. 13, pp. 5516-5519.
Weinbrand-Goichberg, et al. (Jul. 1, 2013) "Eosinophilic Esophagitis: An Immune-Mediated Esophageal Disease", Immunologic Research, vol. 56, No. 2-3, pp. 249-260.
Wershil, Barry K. (Feb. 1, 2009) "Exploring the Role of Mast Cells in Eosinophilic Esophagitis", Immunology and Allergy Clinics of North America, vol. 29, No. 1, pp. 189-195.
Whalley, et al. (Feb. 2004) "A New Instrument for Assessing Quality of Life in Atopic Dermatitis: International Development of the Quality of Life Index for Atopic Dermatitis (Qoliad)", British Journal of Dermatology, vol. 150, pp. 274-283.
"WHO Drug Information", 2012, vol. 26, No. 4, Proposed INN: List 108, p. 412.
Wilhelm, et al. (Nov. 28, 2011) "Innate Lymphoid Cells and Type 2 (TH2) Mediated Immune Responses—Pathogenic or Beneficial?", Frontiers in Immunology, vol. 2, Article 68, pp. 1-4.
Winter et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.
Yang (2002) "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1, 1 page.
Bachert et al. (2005) "Pharmacological management of nasal polyposis," Drugs. 65(11):1537-1552.
Extended European Search Report for European Patent Application No. 21191120.1, mailed Mar. 2, 2022.
Extended European Search Report for European Patent Application No. 21199451.2, mailed May 9, 2022.
International Search Report with Written Opinion corresponding to International Patent Application No. PCT/US2013/055747, mailed Feb. 13, 2014.
Opposition against European Patent No. 3107575 (EP Application No. 15708991.3), filed on May 4, 2022, on behalf of Dr. Hans Ulrich Dörries.
U.S. Appl. No. 61/943,019, filed Feb. 21, 2014, cited in Opposition against European Patent No. 3107575 (EP Application No. 15708991.3), filed on May 4, 2022, on behalf of Dr. Hans Ulrich Dörries.
European Patent Application No. 14306413.7 filed Sep. 15, 2014, cited in Opposition against European Patent No. 3107575 (EP Application No. 15708991.3), filed on May 4, 2022, on behalf of Dr. Hans Ulrich Dörries.
U.S. Appl. No. 62/077,669, filed Nov. 10, 2014, cited in Opposition against European Patent No. 3107575 (EP Application No. 15708991.1), filed on May 4, 2022, on behalf of Dr. Hans Ulrich Dörries.
Barnes, "Scientific rationale for inhaled combination therapy with long-acting ß2- agonists and corticosteroids", The European Respiratory Journal, Jan. 2002, 19(1): 182-191.
FDA drug label "Symbicort", revised May 2012, cited in Opposition against European Patent No. 3107575 (EP Application No. 15708991.3), filed on May 4, 2022, on behalf of Dr. Hans Ulrich Dörries.
FDA drug label "Dulera", revised Jun. 2010, cited in Opposition against European Patent No. 3107575 (EP Application No. 15708991.3), filed on May 4, 2022, on behalf of Dr. Hans Ulrich Dörries.
Bice et al., "Biologic targeted therapy in allergic asthma", Annals of Allergy, Asthma & Immunology, 2014, 112(2): 108-115, cited in Opposition against European Patent No. 3107575 (EP Application No. 15708991.3), filed on May 4, 2022, on behalf of Dr. Hans Ulrich Dörries.
Gibaldi, "Biopharmaceutics and Clinical Pharmacokinetics", 4th Edition, 1991, Lea & Febiger, pp. 12-13, cited in Opposition against European Patent No. 3107575 (EP Application No. 15708991.3), filed on May 4, 2022, on behalf of Dr. Hans Ulrich Dörries.
ClinicalTrials.gov, Information about clinical study "NCT01854047", "An Evaluation of Dupilumab in Patients With Moderate to Severe Uncontrolled Asthma", study record version of Feb. 18, 2014, retrieved from the ClinicalTrials.gov archive url: <https://clinicaltrials.ciovict2/show/record/NCT01854047?intr=Dupilumab+OR+REGN-668+OR+REGN668+OR+SAR-231893+OR+SAR231893&phase=1&draw=3&rank=13>, cited in Opposition against European Patent No. 3107575 (EP Application No. 15708991.3), filed on May 4, 2022, on behalf of Dr. Hans Ulrich Dörries.

(56) References Cited

OTHER PUBLICATIONS

ClinicalTrials.gov, Information about clinical study "NCT02134028", "Long-Term Safety Evaluation of Dupilumab in Patients With Asthma", study record version of Jan. 8, 2015, retrieved from the ClinicalTrials.gov archive url: <https://clinicaltrials.clovict2/show/record/NCT02134028?term=NCT02134028&draw=2&rank=1>, cited in Opposition against European Patent No. 3107575 (EP Application No. 15708991.3), filed on May 4, 2022, on behalf of Dr. Hans Ulrich Dörries.

Annex to the Notice of Opposition against European Patent No. 3107575 (EP Application No. 15708991.3), Facts and Arguments in accordance with Rule 76(2)(c) EPC, filed on May 25, 2022.

International Nonproprietary Names for Pharmaceutical Substances (INN), pp. 401, 402 and 412 of WHO Drug Information, 2012, 26(4):401-471, cited in Annex to the Notice of Opposition against European Patent No. 3107575 (EP Application No. 15708991.3), Facts and Arguments in accordance with Rule 76(2)(c) EPC, filed on May 25, 2022.

EurekAlert! press release "Monoclonal antibody appears effective and safe in asthma Phase IIa trial", May 21, 2013, cited in Annex to the Notice of Opposition against European Patent No. 3107575 (EP Application No. 15708991.3), Facts and Arguments in accordance with Rule 76(2)(c) EPC, filed on May 25, 2022.

Chapter 19, "Dosage regimens", of Aulton's Pharmaceutics: The Science of Dosage Form Design, $2_{nd}$ Edition, 2001, cited in Annex to the Notice of Opposition against European Patent No. 3107575 (EP Application No. 15708991.3), Facts and Arguments in accordance with Rule 76(2)(c) EPC, filed on May 25, 2022.

Ackerman et al., pp. 159 to 162 of Rispens and Vidarsson, Antibody Fc: Linking Adaptive and Innate Immunity, Chapter 9, "Human IgG Subclasses", pp. 159 to 162, 2013; and evidence of its publication date, cited in Annex to the Notice of Opposition against European Patent No. 3107575 (EP Application No. 15708991.3), Facts and Arguments in accordance with Rule 76(2)(c) EPC, filed on May 25, 2022.

Panaccione et al., "Optimal use of biologics in the management of Crohn's disease", Ther. Adv. Gastroenterol., 2010, 3(3): 179-189, which is a review article relating to the optimal use of biologics in the inflammatory disorder, Crohn's disease, cited in Annex to the Notice of Opposition against European Patent No. 3107575 (EP Application No. 15708991.3), Facts and Arguments in accordance with Rule 76(2)(c) EPC, filed on May 25, 2022.

ClinicalTrials.gov, NCT01854047 clinical trial protocol version 22 (Feb. 3, 2014), cited in Annex to the Notice of Opposition against European Patent No. 3107575 (EP Application No. 15708991.3), Facts and Arguments in accordance with Rule 76(2)(c) EPC, filed on May 25, 2022.

Global Initiative for Asthma, pp. 29 to 31 and 58 of the Global Strategy for Asthma Management and Prevention, 2009, cited in Annex to the Notice of Opposition against European Patent No. 3107575 (EP Application No. 15708991.3), Facts and Arguments in accordance with Rule 76(2)(c) EPC, filed on May 25, 2022.

Notice of Opposition against European Patent No. 3107575 (EP Application No. 15708991.3) filed on behalf of Regina Neuefeind, dated May 25, 2022.

Applicants' letter dated Sep. 20, 2016, cited in Notice of Opposition against European Patent No. 3107575 (EP Application No. 15708991.3) filed on behalf of Regina Neuefeind, dated May 25, 2022.

Amended claims enclosed with letter dated Sep. 20, 2016, cited in Notice of Opposition against European Patent No. 3107575 (EP Application No. 15708991.3) filed on behalf of Regina Neuefeind, dated May 25, 2022.

Applicants' letter dated Jul. 25, 2019, cited in Notice of Opposition against European Patent No. 3107575 (EP Application No. 15708991.3) filed on behalf of Regina Neuefeind, dated May 25, 2022.

Amended claims enclosed with letter dated Jul. 25, 2019, cited in Notice of Opposition against European Patent No. 3107575 (EP Application No. 15708991.3) filed on behalf of Regina Neuefeind, dated May 25, 2022.

Radin et al., "Abstract 558: First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J Allergy clin Immunol, Feb. 2013, cited in Notice of Opposition against European Patent No. 3107575 (EP Application No. 15708991.3) filed on behalf of Regina Neuefeind, dated May 25, 2022.

Swanson et al., 2014, "Poster 1023: Dupilumab suppresses Th2 inflammation in adult asthma and atopic dermatitis", World Allergy Organization Journal, Presented on Dec. 13-14, 2013, cited in Notice of Opposition against European Patent No. 3107575 (EP Application No. 15708991.3) filed on behalf of Regina Neuefeind, dated May 25, 2022.

Sanofi and Regeneron Pharmaceuticals Inc., Press Release Nov. 11, 2014, "Dupilumab Demonstrated Improvement in Lung Function, Reductions of Severe Exacerbations", cited in Notice of Opposition against European Patent No. 3107575 (EP Application No. 15708991.3) filed on behalf of Regina Neuefeind, dated May 25, 2022.

Regeneron Pharmaceuticals Inc., Press Release Jul. 9, 2014, at 5:00 PM EDT, "Regeneron and Sanofi Announce Positive Results from Phase 2B Study of Dupilumab in Patients with Moderate -to-Severe Atopic Dermatitis", cited in Notice of Opposition against European Patent No. 3107575 (EP Application No. 15708991.3) filed on behalf of Regina Neuefeind, dated May 25, 2022.

Regeneron Pharmaceuticals Inc., Mar. 2, 2013, at 9:00 AM EST, "Sanofi and Regeneron Report Positive Proof-of-Concept Data for Dupilumab, an IL-4R Alpha Antibody, in Atopic Dermatitis", cited in Notice of Opposition against European Patent No. 3107575 (EP Application No. 15708991.3) filed on behalf of Regina Neuefeind, dated May 25, 2022.

Beck et al., "Dupilumab Treatment in Adults with Moderate-to-Severe Atopic Dermatitis", N Engl J Med, Jul. 10, 2014, 371: 130-139, cited in Notice of Opposition against European Patent No. 3107575 (EP Application No. 15708991.3) filed on behalf of Regina Neuefeind, dated May 25, 2022.

Brusselle et al., "Targeting Immune Pathways for Therapy in Asthma and Chronic Obstructive Pulmonary Disease", Ann Am Thorac Soc, 2014, 11(Suppl. 5): S322-S328, cited in Notice of Opposition against European Patent No. 3107575 (EP Application No. 15708991.3) filed on behalf of Regina Neuefeind, dated May 25, 2022.

Possa et al., "Eosinophilic inflammation in allergic asthma", Frontiers in Pharmacology, 2013, 4(46): 1-9, cited in Notice of Opposition against European Patent No. 3107575 (EP Application No. 15708991.3) filed on behalf of Regina Neuefeind, dated May 25, 2022.

Liang et al., "Moderate Accuracy of Peripheral Eosinophil Count for Predicting Eosinophilic Phenotype in Steroid-Naïve Non-Atopic Adult Asthmatics", Intern Med., 2012, 51: 717-722, cited in Notice of Opposition against European Patent No. 3107575 (EP Application No. 15708991.3) filed on behalf of Regina Neuefeind, dated May 25, 2022.

Katz et al., "Blood Eosinophil Count Is a Useful Biomarker to Identify Patients with Severe Eosinophilic Asthma", Ann Am Thorac Soc., 2014, 11(4): 531-536, cited in Notice of Opposition against European Patent No. 3107575 (EP Application No. 15708991.3) filed on behalf of Regina Neuefeind, dated May 25, 2022.

NHS Health Research Authority, "Dupilumab for adult patients with moderate to severe atopic dermatitis", REC Opinion, May 30, 2014, cited in Notice of Opposition against European Patent No. 3107575 (EP Application No. 15708991.3) filed on behalf of Regina Neuefeind, dated May 25, 2022.

Notice of Opposition against European Patent No. 3470432 (Application No. 18194745.8) filed on Jul. 5, 2022, on behalf of Secerna LLP.

D1—Wenzel, Severe Asthma: from characteristics to phenotypes to endotypes (review), Clinical & Experimental Allergy, Jan. 18, 2012, 42: 650-658, cited in Notice of Opposition against European Patent No. 3470432 (Application No. 18194745.8) filed on Jul. 5, 2022, on behalf of Secerna LLP.

D2—Wenzel, Asthma phenotypes: the evolution from clinical to molecular approaches (review), Nature Medicine, May 4, 2012,

(56) References Cited

OTHER PUBLICATIONS

18(5): 716-725, cited in Notice of Opposition against European Patent No. 3470432 (Application No. 18194745.8) filed on Jul. 5, 2022, on behalf of Secerna LLP.
D3—GINA Report Dec. 2011, Global Strategy for Asthma Management and Prevention, GINA ©2011 & Global Initiative for Asthma, reprinted with permission, Available from www.ginasthma org, cited in Notice of Opposition against European Patent No. 3470432 (Application No. 18194745.8) filed on Jul. 5, 2022, on behalf of Secerna LLP.
D4—GINA Report Dec. 2012, Global Strategy for Asthma Management and Prevention, GINA ©2012 & Global Initiative for Asthma, reprinted with permission, Available from www.ginasthma. org, cited in Notice of Opposition against European Patent No. 3470432 (Application No. 18194745.8) filed on Jul. 5, 2022, on behalf of Secerna LLP.
D5—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Secerna LLP.
D6—Protocol for: Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Secerna LLP.
D7—Weschler, Inhibiting interleukin-4 and interleukin-13 in difficult-to-control asthma, N Engl J Med., May 21, 2013, 368: 2511-2513, cited in Notice of Opposition against European Patent No. 3470432 (Application No. 18194745.8) filed on Jul. 5, 2022, on behalf of Secerna LLP.
D8—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 5, 2022, on behalf of Secerna LLP.
D9—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 5, 2022, on behalf of Secerna LLP.
D10—Study NCT01312961 (v31), Efficacy, Safety, and Tolerability of SAR231893 (REGN668) in Patients with Persistent Moderate to Severe Eosinophilic Asthma, Aug. 20, 2012, cited in Notice of Opposition against European Patent No. 3470432 (Application No. 18194745.8) filed on Jul. 5, 2022, on behalf of Secerna LLP.
D11—Press release: Regeneron reports fourth quarter and full year 2011 financial and operating results, Feb. 13, 2012, https://investor.regeneron.com/news-releases/news-release-details/regeneron-reports-fourth-quarter-and-full-year-2011-financial, cited in Notice of Opposition against European Patent No. 3470432 (Application No. 18194745.8) filed on Jul. 5, 2022, on behalf of Secerna LLP.
D12—Otulana et al., A Phase 2b Study of Inhaled Pitrakinra, an IL-4 / IL-13 antagonist, successfully identified responder subpopulations of patients with uncontrolled asthma, American Journal of Respiratory and Critical Care Medicine, May 18, 2011, 183: A6179, cited in Notice of Opposition against European Patent No. 3470432 (Application No. 18194745.8) filed on Jul. 5, 2022, on behalf of Secerna LLP.
D13—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 5, 2022, on behalf of Secerna LLP.
D14—Hashimoto & Bel, Targeting IL-5 in severe asthma: a DREAM come true?, The Lancet, Aug. 8, 2012, 380(9842): 626-627, cited in Notice of Opposition against European Patent No. 3470432 (Application No. 18194745.8) filed on Jul. 5, 2022, on behalf of Secerna LLP.
D15—Pavord al., Mepolizumab for severe eosinophilic asthma (DREAM): a multicentre, double-blind, placebo-controlled trial, Lancet, Aug. 18, 2012; 380: 651-659, cited in Notice of Opposition against European Patent No. 3470432 (Application No. 18194745.8) filed on Jul. 5, 2022, on behalf of Secerna LLP.
D16—Szefler et al., Asthma Outcomes: Biomarkers, J Allergy Clin Immunol., Mar. 1, 2012, 129: S9-23, cited in Notice of Opposition against European Patent No. 3470432 (Application No. 18194745.8) filed on Jul. 5, 2022, on behalf of Secerna LLP.
D17—Spector & Tan, Is a single blood eosinophil count a reliable marker for "eosinophilic asthma?", Journal of Asthma, Aug. 20, 2012, 49.8: Early Online: 1-4, cited in Notice of Opposition against European Patent No. 3470432 (Application No. 18194745.8) filed on Jul. 5, 2022, on behalf of Secerna LLP.
D18—WHO Drug Information, vol. 26, No.4, p. 412, Dec. 9, 2012, cited in Notice of Opposition against European Patent No. 3470432 (Application No. 18194745.8) filed on Jul. 5, 2022, on behalf of Secerna LLP.
D19—Firszt & Kraft, Pharmacotherapy of Severe Asthma, Curr Opin Pharmacol., Jun. 2010, 10(3): 266-271, cited in Notice of Opposition against European Patent No. 3470432 (Application No. 18194745.8) filed on Jul. 5, 2022, on behalf of Secerna LLP.
D20—Darveax & Busse, Biologics in asthma—the next step to personalised treatment, J Allergy Clin Immunol Pract., Mar.-Apr. 2015, 3(2): 152-161, cited in Notice of Opposition against European Patent No. 3470432 (Application No. 18194745.8) filed on Jul. 5, 2022, on behalf of Secerna LLP.
D21—Eisenstein, Something new under the skin, Nature Biotechnology, Feb. 7, 2011, 29(2): 107-109, cited in Notice of Opposition against European Patent No. 3470432 (Application No. 18194745.8) filed on Jul. 5, 2022, on behalf of Secerna LLP.
D22—Chapter 19, "Dosage regimens" of Aulton's Pharmaceutics: The Science of Dosage Form Design, 2nd Edition, 2001, cited in Notice of Opposition against European Patent No. 3470432 (Application No. 18194745.8) filed on Jul. 5, 2022, on behalf of Secerna LLP.
P1—U.S. Appl. No. 61/691,625, filed Aug. 21, 2012, cited in Notice of Opposition against European Patent No. 3470432 (U.S. Appl. No. 61/691,625, filed Aug. 21, 2012) filed on Jul. 5, 2022, on behalf of Secerna LLP.
P2—U.S. Appl. No. 61/758,097, filed Jan. 29, 2013, cited in Notice of Opposition against European Patent No. 3470432 (U.S. Appl. No. 61/758,097, filed Jan. 29, 2013) filed on Jul. 5, 2022, on behalf of Secerna LLP.
P3—U.S. Appl. No. 61/761,279, filed Feb. 6, 2013, cited in Notice of Opposition against European Patent No. 3470432 (U.S. Appl. No. 61/761,279, filed Feb. 6, 2013) filed on Jul. 5, 2022, on behalf of Secerna LLP.
P4—U.S. Appl. No. 61/783,796, filed Mar. 14, 2013, cited in Notice of Opposition against European Patent No. 3470432 (U.S. Appl. No. 61/783,796, filed Mar. 14, 2013) filed on Jul. 5, 2022, on behalf of Secerna LLP.
P5—U.S. Appl. No. 61/805,797, filed Mar. 27, 2013, cited in Notice of Opposition against European Patent No. 3470432 (U.S. Appl. No. 61/805,797, filed Mar. 27, 2013) filed on Jul. 5, 2022, on behalf of Secerna LLP.
P6—French Patent Application No. 1356994, filed Jul. 16, 2013, cited in Notice of Opposition against European Patent No. 3470432 (Application No. 18194745.8) filed on Jul. 5, 2022, on behalf of Secerna LLP.
A—Divisional Application as filed (EP 18194745.8), dated Sep. 17, 2018, cited in Notice of Opposition against European Patent No. 3470432 (Application No. 18194745.8) filed on Jul. 5, 2022, on behalf of Secerna LLP.
Notice of Opposition against European Patent No. 3470432 (Application No. 18194745.8) filed on Jul. 5, 2022, on behalf of Dr. Hans Ulrich Dorries.
P1—U.S. Appl. No. 61/691,625, filed Aug. 21, 2012, cited in Notice of Opposition against European Patent No. 3470432 (Application No. 18194745.8) filed on Jul. 5, 2022, on behalf of Dr. Hans Ulrich Dorries.

(56) References Cited

OTHER PUBLICATIONS

P2—U.S. Appl. No. 61/758,097, filed Jan. 29, 2013, cited in Notice of Opposition against European Patent No. 3470432 (Application No. 18194745.8) filed on Jul. 5, 2022, on behalf of Dr. Hans Ulrich Dorries.
P3—U.S. Appl. No. 61/761,279, filed Feb. 6, 2013, cited in Notice of Opposition against European Patent No. 3470432 (Application No. 18194745.8) filed on Jul. 5, 2022, on behalf of Dr. Hans Ulrich Dorries.
P4—U.S. Appl. No. 61/783,796, filed Mar. 14, 2013, cited in Notice of Opposition against European Patent No. 3470432 (Application No. 18194745.8) filed on Jul. 5, 2022, on behalf of Dr. Hans Ulrich Dorries.
P5—U.S. Appl. No. 61/805,797, filed Mar. 27, 2013, cited in Notice of Opposition against European Patent No. 3470432 (Application No. 18194745.8) filed on Jul. 5, 2022, on behalf of Dr. Hans Ulrich Dorries.
P6—French Patent Application No. 1356994, filed Jul. 16, 2013, cited in Notice of Opposition against European Patent No. 3470432 (Application No. 18194745.8) filed on Jul. 5, 2022, on behalf of Dr. Hans Ulrich Dorries.
PA—PCT International Publication No. 2014/031610 A1 published Feb. 27, 2014, cited in Notice of Opposition against European Patent No. 3470432 (Application No. 18194745.8) filed on Jul. 5, 2022, on behalf of Dr. Hans Ulrich Dorries.
OA—Divisional application as filed resulting in the opposed patent (European Patent Application No. 21199451.2, filed Sep. 28, 2021), cited in Notice of Opposition against European Patent No. 3470432 (Application No. 18194745.8) filed on Jul. 5, 2022, on behalf of Dr. Hans Ulrich Dorries.
D1—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Dr. Hans Ulrich Dorries.
D2—WHO Drug Information, vol. 26, No.4, pp. 401-471, Proposed INN: List 108, Dec. 9, 2012, cited in Notice of Opposition against European Patent No. 3470432 (Application No. 18194745.8) filed on Jul. 5, 2022, on behalf of Dr. Hans Ulrich Dorries.
D3—O'Byrne et al., Clinical and Experimental Allergy, May 2012, 42(2): 706-711, cited in Notice of Opposition against European Patent No. 3470432 (Application No. 18194745.8) filed on Jul. 5, 2022, on behalf of Dr. Hans Ulrich Dorries.
D4—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 5, 2022, on behalf of Dr. Hans Ulrich Dorries.
D5—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 5, 2022, on behalf of Dr. Hans Ulrich Dorries.
D6—Gibaldi, Biopharmaceutics and Clinical Pharmakokinetics, 4th Ed., 1991, Lea & Febiger, pp. 12-13, cited in Notice of Opposition against European Patent No. 3470432 (Application No. 18194745.8) filed on Jul. 5, 2022, on behalf of Dr. Hans Ulrich Dorries.
Notice of Opposition against European Patent No. 3470432 (Application No. 18194745.8) filed on Jul. 6, 2022, on behalf of D. Young & Co.
D1—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 6, 2022, on behalf of D. Young & Co.
D2—pp. 17, 28, 32, 34, 59 and 61 of the Global Initiative for Asthma: Global Strategy for Asthma Management and Prevention, 2009, cited in Notice of Opposition against European Patent No. 3470432 (Application No. 18194745.8) filed on Jul. 6, 2022, on behalf of D. Young & Co.
D3—Borish, Am J Respir Crit Care Med., 2010, 181: 769-772, cited in Notice of Opposition against European Patent No. 3470432 (Application No. 18194745.8) filed on Jul. 6, 2022, on behalf of D. Young & Co.
D4—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 6, 2022, on behalf of D. Young & Co.
D5—Chapter 19, Dosage Regimens, Alton's Pharmaceutics: The Science of Dosage Form Design, 2nd Ed., 2001, cited in Notice of Opposition against European Patent No. 3470432 (Application No. 18194745.8) filed on Jul. 6, 2022, on behalf of D. Young & Co.
D6—Mould & Sweeney, Current Opinion in Drug Discovery & Development, 2007, 10(1): 84-96, cited in Notice of Opposition against European Patent No. 3470432 (Application No. 18194745.8) filed on Jul. 6, 2022, on behalf of D. Young & Co.
D7—Panaccione and Ghosh, Ther Adv Gastroenterol., 2010, 3(3): 179-189, cited in Notice of Opposition against European Patent No. 3470432 (Application No. 18194745.8) filed on Jul. 6, 2022, on behalf of D. Young & Co.
Notice of Opposition against European Patent No. 3470432 (Application No. 18194745.8) filed on Jul. 6, 2022, on behalf of Ms. Regina Neuefeind.
A—PCT International Publication No. 2014/031610 published Feb. 27, 2014, cited in Notice of Opposition against European Patent No. 3470432 (Application No. 18194745.8) filed on Jul. 6, 2022, on behalf of Ms. Regina Neuefeind.
P1—U.S. Appl. No. 61/691,625, filed Aug. 21, 2012, cited in Notice of Opposition against European Patent No. 3470432 (Application No. 18194745.8) filed on Jul. 6, 2022, on behalf of Ms. Regina Neuefeind.
P2—U.S. Appl. No. 61/758,097, filed Jan. 29, 2013, cited in Notice of Opposition against European Patent No. 3470432 (Application No. 18194745.8) filed on Jul. 6, 2022, on behalf of Ms. Regina Neuefeind.
P3—U.S. Appl. No. 61/761,279, filed Feb. 6, 2013, cited in Notice of Opposition against European Patent No. 3470432 (Application No. 18194745.8) filed on Jul. 6, 2022, on behalf of Ms. Regina Neuefeind.
P4—U.S. Appl. No. 61/783,796, filed Mar. 14, 2013, cited in Notice of Opposition against European Patent No. 3470432 (Application No. 18194745.8) filed on Jul. 6, 2022, on behalf of Ms. Regina Neuefeind.
P5—U.S. Appl. No. 61/805,797, filed Mar. 27, 2013, cited in Notice of Opposition against European Patent No. 3470432 (Application No. 18194745.8) filed on Jul. 6, 2022, on behalf of Ms. Regina Neuefeind.
P6—French Patent Application No. 1356994, filed Jul. 16, 2013, cited in Notice of Opposition against European Patent No. 3470432 (Application No. 18194745.8) filed on Jul. 6, 2022, on behalf of Ms. Regina Neuefeind.
D1—Brusselle and Bracke, Ann Am Thorac Soc., 2014, 11(Suppl. 5): S322-S328, cited in Notice of Opposition against European Patent No. 3470432 (Application No. 18194745.8) filed on Jul. 6, 2022, on behalf of Ms. Regina Neuefeind.
D2—Woodruff et al., Am J Respir Crit Care Med., 2009, 180: 388-395, cited in Notice of Opposition against European Patent No. 3470432 (Application No. 18194745.8) filed on Jul. 6, 2022, on behalf of Ms. Regina Neuefeind.
D3—Liang et al., Intern Med., 2012, 51: 717-722, cited in Notice of Opposition against European Patent No. 3470432 (Application No. 18194745.8) filed on Jul. 6, 2022, on behalf of Ms. Regina Neuefeind.
D4—Gibson, Aust Prescr, 1996, 19: 44-47, cited in Notice of Opposition against European Patent No. 3470432 (Application No. 18194745.8) filed on Jul. 6, 2022, on behalf of Ms. Regina Neuefeind.
D5—WHO Drug Information, vol. 26, No.4, p. 412, 2012, cited in Notice of Opposition against European Patent No. 3470432 (Application No. 18194745.8) filed on Jul. 6, 2022, on behalf of Ms. Regina Neuefeind.

(56) References Cited

OTHER PUBLICATIONS

D6—Pollart et al., American Family Physician, 2009, 79(9): 761-767, cited in Notice of Opposition against European Patent No. 3470432 (Application No. 18194745.8) filed on Jul. 6, 2022, on behalf of Ms. Regina Neuefeind.
D7—Lommatzsch and Virchow, Dtsch Arztebl Int., 2014, 111: 847-855, cited in Notice of Opposition against European Patent No. 3470432 (Application No. 18194745.8) filed on Jul. 6, 2022, on behalf of Ms. Regina Neuefeind.
D8—Applicant's Submission dated Oct. 17, 2019, cited in Notice of Opposition against European Patent No. 3470432 (Application No. 18194745.8) filed on Jul. 6, 2022, on behalf of Ms. Regina Neuefeind.
D9—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 6, 2022, on behalf of Ms. Regina Neuefeind.
D9a—Supplementary Data of D9, cited in Notice of Opposition against European Patent No. 3470432 (Application No. 18194745.8) filed on Jul. 6, 2022, on behalf of Ms. Regina Neuefeind.
D10—Sandeep et al., Lung India, 2010, 27(3), cited in Notice of Opposition against European Patent No. 3470432 (Application No. 18194745.8) filed on Jul. 6, 2022, on behalf of Ms. Regina Neuefeind.
D11—Shannon et al., CHEST, 2008, 133: 420-426, cited in Notice of Opposition against European Patent No. 3470432 (Application No. 18194745.8) filed on Jul. 6, 2022, on behalf of Ms. Regina Neuefeind.
D12—De Boever et al., Asthma and Lower Airway Disease, 2014, 133(4): 989-996, cited in Notice of Opposition against European Patent No. 3470432 (Application No. 18194745.8) filed on Jul. 6, 2022, on behalf of Ms. Regina Neuefeind.
D13—Wenzel et al., Severe asthma in adults, Am J Respir Crit Care Med., 172(2): 149-160; cited in Notice of Opposition against European Patent No. 3470432 (Application No. 18194745.8) filed on Jul. 6, 2022, on behalf of Ms. Regina Neuefeind.
D14—Al-Ramli et al., Journal of Asthma, 2008, 45(S1): 41-44, cited in Notice of Opposition against European Patent No. 3470432 (Application No. 18194745.8) filed on Jul. 6, 2022, on behalf of Ms. Regina Neuefeind.
D15—Bossley et al., J Allergy Clin Immunol., 2012, 129(4): 974-982.e13, cited in Notice of Opposition against European Patent No. 3470432 (Application No. 18194745.8) filed on Jul. 6, 2022, on behalf of Ms. Regina Neuefeind.
D16—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 6, 2022, on behalf of Ms. Regina Neuefeind.
D17—Study NCT01312961 (v31), Efficacy, Safety, and Tolerability of SAR231893 (REGN668) in Patients with Persistent Moderate to Severe Eosinophilic Asthma, Aug. 20, 2012, cited in Notice of Opposition against European Patent No. 3470432 (Application No. 18194745.8) filed on Jul. 6, 2022, on behalf of Ms. Regina Neuefeind.
D18—Birkett, 1996, Aust Prescr 1996, 19: 76-78, retrieved from: https://www.nps.org.au/australian-prescriber/articles/pharmacokinetics-made-easy-11-designing-dose-regimens, cited in Notice of Opposition against European Patent No. 3470432 (Application No. 18194745.8) filed on Jul. 6, 2022, on behalf of Ms. Regina Neuefeind.
D19—Applicant's submission dated Dec. 9, 2011, cited in Notice of Opposition against European Patent No. 3470432 (Application No. 18194745.8) filed on Jul. 6, 2022, on behalf of Ms. Regina Neuefeind.
D20—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 6, 2022, on behalf of Ms. Regina D21—Neuefeind.
D21—Regeneron Science to Medicine, J.P. Morgan Healthcare Conference, Jan. 8, 2013, cited in Notice of Opposition against European Patent No. 3470432 (Application No. 18194745.8) filed on Jul. 6, 2022, on behalf of Ms. Regina Neuefeind.
D21a—Proof of publication date of D21, Jan. 8, 2013, cited in Notice of Opposition against European Patent No. 3470432 (Application No. 18194745.8) filed on Jul. 6, 2022, on behalf of Ms. Regina Neuefeind.
Bachert et al., "Burden of Disease on Chronic Rhinosinusitis with Nasal Polyps", Journal of Asthma and Allergy, 2021, 14: 127-134.
Baiardini, et al., A New Tool to Evaluate the Impact of Chronic Urticaria on Quality of Life: Chronic Urticaria Quality of Life Questionnaire (CU-Q2oL), European Academy of Allergy and Clinical Immunology, vol. 60, No. 8, pp. 1073-1078, 2005.
Bloomstein et al., "Simultaneous treatment of Samter triad and prurigo nodularis with dupilumab", JAAD Case Reports, Dec. 1, 2021, vol. 18, p. 20-22, Retrieved from the Internet: url: https://www.jaadcasereports.org/article/S2352-5126(21)00725-6/pdf.
Brahmer, et al., "Safety and Activity of Anti-PD-L1 Antibody in Patients With Advanced Cancer", New England Journal of Medicine, vol. 366, pp. 2455-2465, Jun. 28, 2012.
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
Canonica, et al., The EAACI/GA2LEN/EDF/WAO Guideline for the Definition, Classification, Diagnosis, and Management of Urticaria: The 2013 Revision and Update, European Academy of Allergy and Clinical Immunology, vol. 69, No. 7, pp. 868-887, 2014.
Casale, et al., Similar Efficacy with Omalizumab in Chronic Idiopathic/Spontaneous Urticaria Despite Different Background Therapy, The Journal of Allergy and Clinical Immunology: In Practice, vol. 3, No. 5, pp. 743-750.e1, 2015.
Celakovska, J. et al., "Sensitization to aeroallergens in atopic dermatitis patients: association with concomitant allergic diseases", JEADV 2015; 29, 1500-1505.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Chen, et al., Different Expression Patterns of Plasma Th1-, Th2-, Th17- and Th22-related Cytokines Correlate With Serum Autoreactivity and Allergen Sensitivity in Chronic Spontaneous Urticaria, Journal of the European Academy of Dermatology & Venereology, vol. 32, No. 3, pp. 441-448, Mar. 2018.
Clinical Trials, Study NCT00436670, "Phase II Study to Evaluate the Efficacy of AMG 317", first posted Feb. 19, 2007, Amgen actual study completion date—Feb. 2009, 7 pages.
Clinical Trials, Study NCT01859988, phase 2b, "Study of Dupilumab Administered to Adult Patients With Moderate-to-Severe Atopic Dermatitis", study completion date—Sep. 2014, 10 pages.
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
Confino-Cohen et al., Low Stimulated Il-4 Secretion in Pbmc From Patients With Chronic Idiopathic Urticaria, Cytokine, vol. 27, No. 2-3, pp. 74-80, 2004.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
D'Erme, Angelo et al., "Spotlight on dupilumab in the treatment of atopic dermatitis: design, development, and potential place in therapy", Drug Des Devel Ther, 2017, vol. 11, p. 1473-1480, DOI:10.2147/DDDT.S113192, Abstract, c. 1475-1478, 8 pages.
Degirmenci et al., Analysis of the Association of Chronic Spontaneous Urticaria With Interlekin-4, -10, Transforming Growth Factor-β1, Interferon-γ, Interleukin-17a and -23 by Autologous Serum Skin Test, Advances in Dermatology and Allergology/Postpy Dermatologii i Alergologii, vol. 34, No. 1, pp. 70-76, 2017.

(56) References Cited

OTHER PUBLICATIONS

Donald, et al., Unknown Publication, Current Opinion in Otolaryngology & Head and Neck Surgery, vol. 21 & 23, 2013.
Errichetti et al., "Recalcitrant chronic urticaria treated with dupilumab: Report of two instances refractory to H1-antihistamines, omalizumab and cyclosporine and brief literature review", Dermatologic Therapy, Mar./Apr. 2021, 34(2): e14821.
FDA (Mar. 1, 2019) "Highlights of Prescribing Information", Sep. 29, 2022, Retrieved from url: https://www.accessdata.fda.gov/drugsatfda_docs/label/2022/761055s044lbl.pdf.
Finkelman, Fred, et al., "Regulation of murine in vivo IgG and IgE responses by a monoclonal anti-IL-4 receptor antibody", Jun. 1991;3(6); 599-607.
Garraud, Olivier, et al., "Regulation of immunoglobulin production in hyper-IgE (Job's) syndrome", J. Allergy Clin. Immunol., Feb. 1999. (2 Pt. 1): 333-340.
Giménez-Arnau, et al., The Pathogenesis of Chronic Spontaneous Urticaria: The Role of Infiltrating Cells, The Journal of Allergy and Clinical Immunology: In Practice, vol. 9, No. 6, pp. 2195-2208, Jun. 2021.
Gong, J.Q et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Gonnet, et al., Exhaustive Matching of the Entire Protein Sequence Database, Science, vol. 256, No. 5062, pp. 1443-1445, Jun. 5, 1992.
Grob, et al., Comparative Study of the Impact of Chronic Urticaria, Psoriasis and Atopic Dermatitis on the Quality of Life, British Journal of Dermatology, vol. 152, No. 2, pp. 289-295, 2005.
Hambly, et al., "Monoclonal Antibodies for the Treatment of Refractory Asthma", Current Opinion in Pulmonary Medicine, vol. 20, Issue 1, pp. 87-94, Jan. 2014.
Hamilton, Jennifer et al., "Dupilumab Normalizes the Eosinophilic Esophagitis Disease Transcriptome in Adult Patients With Eosinophilic", May 1, 2020, Abstract, retrieved from internet on Aug. 5, 2021 at.
Harris, Jeffrey et al., "A randomized trial of the efficacy and safety of quilizumab in adults with inadequately controlled allergic asthma", Respiratory Research (2016) 17:29, 11 pages.
Hawro, et al., The Urticaria Activity Score—Validity, Reliability, and Responsiveness, The Journal of Allergy and Clinical Immunology: In Practice, vol. 6, No. 4, pp. 1185-1190.e1, 2018.
Healio Gastroenterology, "Novel therapy improved disease features in EoE", Oct. 8, 2019, located online at: https://www.healio.com/news/gastroenterology/20191008/novel-therapy-improves-disease-features-in-eoe, 2 pages.
Hendricks et al., "Dupilumab use in dermatologic conditions beyond atopic dermatitis—a systematic review", Journal of Dermatological Treatment, 2023, 23(1): 19-28.
Herdman, et al., Development and Preliminary Testing of the New Five-level Version of EQ-5D (EQ-5D-5L), Quality of Life Research, vol. 20, No. 10, pp. 1727-1736, Apr. 9, 2011.
Hollis, et al., Comparison of Urticaria Activity Score Over 7 Days (UAS7) Values Obtained from Once-Daily and Twice-Daily Versions: Results from the ASSURE-CSU Study, American Journal of Clinical Dermatology, vol. 19, No. 2, pp. 267-274, Jan. 24, 2018.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
International Search Report and Written Opinion for PCT International Patent Application No. PCT/US2018/058039, mailed Jan. 28, 2019.
International Search Report and Written Opinion for PCT International Patent Application No. PCT/US2020/030824, dated Sep. 1, 2020.
International Search Report with Written Opinion for PCT International Patent Application No. PCT/US2020/066559, mailed May 31, 2021.
International Search Report with Written Opinion for PCT International Patent Application No. PCT/US2021/053328, mailed Feb. 23, 2022.
International Search Report with Written Opinion for PCT International Patent Application No. PCT/US2022/038185, mailed Jan. 10, 2023.
International Search Report with Written Opinion for PCT International Patent Application No. PCT/US2022/078341 mailed Mar. 7, 2023.
Kharkevich, "Pharmacology", 10th Ed., GEOTAR-Media, 2010, 908 p. page 42. [Russian w/ English translation].
Kharkevich, "Pharmacology", 9th Ed., Revised, added and corrected, GEOTAR-Media, 2006, pp. 66-67. [Russian language only].
Kim et al., "Engineering of anti-human interleukin-4 receptor alpha antibodies with potent antagonistic activity", Scientific Reports, 2019, vol. 9, Article No. 7772, pp. 1-12.
Krylov and Bobyrev, "Pharmacology", Moscow, 1999, "Routes of administration". [Russian language only].
Kussie, Paul, et al., "A Single Engineered Amino Acid Substitution Changes Antibody Fine Specificity", Journal of Immunology: 152, pp. 146-152, 1994.
Kwiatek, Monika et al., "Mechanical properties of the esophagus in eosinophilic esophagitis" Gastroenterology, 2011, vol. 140, No. 1, pp. 82-90.
Langley, R.G., et al., "Secukinumab in plaque psoriasis—results of two phase 3 trials", New England Journal of Medicine, Jul. 24, 2014, 371:4, pp. 326-338.
Lee et al., "Blockade of IL-33/ST2 ameliorates airway inflammation in a murine model of allergic asthma", Exp Lung Res., Mar. 2014, 40(2): 66-76.
Lee et al., "Dupilumab as a novel therapy for difficult to treat chronic spontaneous urticaria", Clinical Communicatinos, May 2019, 7(5): P1659-1661.E1.
Liew et al., "Interleukin-33 in health and disease", Nat Rev immunology, Nov. 2016, 16(11): 676-689.
Linden, Carey et al., "Analysis of allergen specific IgE cut points to cat and dog in the Childhood Allergy Study", Annals of Allergy, Asthma & Immunology, 2011, 106.2: 153-158. e2.
Liu et al., "Anti-IL-33 antibody treatment inhibits airway inflammation in a murine model of allergic asthma", Biochemical and Biophysical Research Communications, Aug. 14, 2009, 386(1): 181-185.
Lucae, S et al., "IgE responses to exogenous and endogenous allergens in atopic dermatitis patients under long-term systemic cyclosporine A treatment", Allergy 71 (2016); 115-118.
Maes, et al., "Targeting Interleukin-4 in Asthma: Lost in Translation?", American Journal of Respiratory Cell and Molecular Biology, vol. 47, pp. 261-270, 2012.
Mathias, et al., Evaluating the Minimally Important Difference of the Urticaria Activity Score and Other Measures of Disease Activity in Patients With Chronic Idiopathic Urticaria, Annals of Allergy, Asthma & Immunology, vol. 108, No. 1, pp. 20-24, Jan. 2012.
Maurer, et al., Omalizumab for the Treatment of Chronic Idiopathic or Spontaneous Urticaria, The New England Journal of Medicine, vol. 368, No. 10, pp. 924-935, Feb. 24, 2013.
Maurer, et al., Unmet Clinical Needs in Chronic Spontaneous Urticaria. A GA2LEN Task Force Reportt, Allergy, vol. 66, No. 3, pp. 317-330, 2011.
Mayo Foundation for Medical Education and Research (MFMER), "Chronic Sinusitis", Aug. 1, 2020.
Mcgregor et al., "Role of Biologics in Asthma", Am J Respir Crit Care Med., Feb. 15, 2019, 1999(4): 433-445.
Mendelsohn, et al., "Revision Rates after Endoscopic Sinus Surgery: A Recurrence Analysis", Annals of Otology, Rhinology & Laryngology, vol. 120, No. 3, pp. 162-166., 2011.
Mlynek, et al., How to Assess Disease Activity in Patients With Chronic Urticaria?, European Academy of Allergy and Clinical Immunology, vol. 63, No. 6, pp. 777-780, 2008.
Moestrup et al., "Patient-reported outcomes (PROs) in chronic urticaria", Int'l Journal opf Dermatology, Dec. 2017, 56(12): 1342-1348.

(56) References Cited

OTHER PUBLICATIONS

Mulder, DJ et al., "Understanding eosinophilic esophagitis: the cellular and molecular mechanisms of an emerging disease", Mucosal Immunology, Mar. 2011, vol. 4, No. 2, pp. 139-147.
Na et al., "IL-33 enhances Siglec-8 mediated apoptosis of human eosinophils", Cytokine, Oct. 17, 2011, 57(1): 169-174.
Navarini, A., et al., "Interrupting IL-6-receptor signaling improves atopic dermatitis but associates with bacterial superinfection", Nov. 2011 J Allergy Clin Immunol, Letters to the Editor, pp. 1128-1130.
Paller et al., "Efficacy and safety of dupilumab with concomitant topical corticosteroids in children 6 to 11 years old with severe atopic dermatitis: A randomized, double-blinded, placebo-controlled phase 3 trial", J Am Acad Dermatol., Nov. 2020, vol. 83, No. 5, pp. 1282-1293, Epub Jun. 20, 2020.
Radin et al., "First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., page AB158, (made available on Jan. 26, 2013), 2 pgs.
Ramonell et al., Dupilumab treatment for allergic bronchopulmonary aspergillosis: A case series, J Clin Innunol Pract., Feb. 2020, 8(2): 742-743.
Reed, Craig, et al., "Patient-reported outcomes in esophageal diseases", Clinical Gastroenterology and Hepatology, Elsevier, Amsterdam, NL, vol. 16. No. 3, pp. 305-310.
Sandeep et al., Evaluation of serum immunoglobulin E levels in bronchial asthma, Lung India, July-Sep. 2010, 27(3).
Sanofi (Dec. 22, 2017) "Evaluation of SAR440340 and as Combination Therapy with Dupilumab in Moderate-to-Severe Asthma Participants", Clinical Trials Accession No. A327NCT03387852, Retrieved from: <<https://clinicaltrials.gov/ct2/show/NCT03387852>>.
Sanofi, "Dupixent (dupilumab) significantly reduced severe asthma attacks in children and is the only biologic to demonstrate improvement in children's lung function in a randomized Phase 3 trial", Oct. 13, 2020, pp. 1-6, retrieved from url: https://ml-eu.globenewswire.com/Resource/Download/326080b9-593f-4d56-8035-48827a7b5bf4.
Sanofi, clinicaltrials.gov (Aug. 20, 2012) "Efficacy, Safety, and Tolerability of Dupilumab in Patients With Persisten Moderate to Severe Eosinophilic Asthma," [accessible on the internet at: https://clinicaltrials.gov/ct2/show/NCT01312961].
Semprini et al., Change in biomarkers of type-2 inflammation following severe exacerbations of asthma, Thorax, 2019, 74: 95-98.
Shikiar, et al., Minimal Important Difference (MID) of the Dermatology Life Quality Index (DLQI): Results From Patients With Chronic Idiopathic Urticaria, Health and Quality of Life Outcomes, vol. 3, No. 36, pp. 1-5, May 20, 2005.
Staubach et al., "Severe chronic spontaneous urticaria in children - treatment options according to the guidelines and beyond—a 10 years review", Journal of Dermatological Treatment, 2022, 33(2): 1119-1122.
Stull et al., "Analysis of disease activity categories in chronic spontaneous/idiopathic urticaria", British Journal of Dermatology, Oct. 1, 2017, 177(4): 1093-1101.
Tanis et al., "Dupilumab treatment for prurigo nodularis", J Drugs Dermatol., Sep. 1, 2019, 18(9): 940-942, Retrieved from url: https://pubmed.ncbi.nlm.nih.gov/31524352/.
Ulashchik, "The targeted transport of the medicinal substances and the therapeutic physical factors", Voprosy kurortologii, fizioterapii, i lechebnoi fizicheskoi kultury 2014, 91(6): 52-61 [in Russian].
US Securities and Exchange Commission Web Site 2019, Form S-1, Dec. 21, 2018, XP055720304, Retrieved from url: <https://www.sec.gov/Archives/edgar/data/1728117/000119312518356444/d626950ds1.htm>.
Vincent, M. et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.
Waccholz et al., "Detection of Allergen-Specific IgE Antibody Responses", 2005, Journal of Immunotoxicology, 1:3-4, 189-199.
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Weller, Development and Validation of the Urticaria Control Test: a Patient-reported Outcome Instrument for Assessing Urticaria Control, Journal of Allergy and Clinical Immunology, vol. 133, No. 5, pp. 1365-1372.e6, 2014.
Weller, et al., Development, Validation, and Initial Results of the Angioedema Activity Score, European Academy of Allergy and Clinical Immunology, vol. 68, No. 9, pp. 1185-1192, 2013.
Wille, et al., Development of the EQ-5D-Y: a Child-friendly Version of the EQ-5D, Quality of Life Research, vol. 19, No. 6, pp. 875-886, Apr. 20, 2010.
Yamanaka et al. (2011) "The Role of Cytokines/Chemokines in the Pathogenesis of Atopic Dermatitis," Curr. Probl. Dermatol. 41:80-92.
Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.
Yasuhara, et al. (Jul. 2010) "Fundamentals of Clinical Pharmacokinetics", Clinical Pharmacology, vol. 41, Issue 4, pp. 155-158.
Zhu et al., "Potential New Targets for Drug Development in Severe Asthma", World Allergy Organization Journal, Oct. 25, 2018, 11(30): 1-9.
Zuberbier, et al., Epidemiology of Urticaria: a Representative Cross-sectional Population Survey, Clinical and Experimental Dermatology, vol. 35, No. 8, pp. 869-873, 2010.
Zuberbier, et al., The EAACI/GA$^2$LEN/EDF/WAO Guideline for the Definition, Classification, Diagnosis and Management of Urticaria, European Academy of Allergy and Clinical Immunology, vol. 73, No. 7, pp. 1393-1414, 2018.
Third Party Observation dated Aug. 1, 2023, for European Publication No. 4011915 (Application No. 21199451.2).
D1—GINA Report Dec. 2011, Global Strategy for Asthma Management and Prevention, GINA ©2011 & Global Initiative for Asthma, reprinted with permission, Available from www.ginasthma org, cited in Third Party Observation dated Aug. 1, 2023, for European Publication No. 4011915 (Application No. 21199451.2).
D2—Wenzel, Severe Asthma: from characteristics to phenotypes to endotypes (review), Clinical & Experimental Allergy, Jan. 18, 2012, 42: 650-658, cited in Third Party Observation dated Aug. 1, 2023, for European Publication No. 4011915 (Application No. 21199451.2).
D3—Wenzel, Asthma phenotypes: the evolution from clinical to molecular approaches (review), Nature Medicine, May 4, 2012, 18(5): 716-725, cited in Third Party Observation dated Aug. 1, 2023, for European Publication No. 4011915 (Application No. 21199451.2).
D4—U.S. Pat. No. 8,075,887 B2, High Affinity Human Antibodies to Human IL-4 Receptor, issued Dec. 13, 2011, cited in Third Party Observation dated Aug. 1, 2023, for European Publication No. 4011915 (Application No. 21199451.2).
Brandt et al., "Th2 Cytokines and Atopic Dermatitis", J Clin Cell Immunol., Aug. 10, 2011, 2(3): 110.
ClinicalTrials.gov Identifier NCT02528214, Oct. 24, 2017, Evaluation of Dupilumab in Patients with Severe Steroid Dependent Asthma (VENTURE).
ClinicalTrials.gov Identifier: NCT02948959, Oct. 27, 2016, Evaluation of Dupilumab in Children With Uncontrolled Asthma (VOYAGE).
Drugs.com, "Asthma Medications", 2014, obtained from url: <http://web.archive.org/web/20140131041952/http://www.drugs.com/asthma.html>.
Extended European Search Report for European Application No. 23202532.0, dated Mar. 27, 2024.
Extended European Search Report for European Application No. 23206862.7, dated Apr. 24, 2024.

(56) References Cited

OTHER PUBLICATIONS

Peters et al., "Uncontrolled asthma: a review of the prevalence, disease burden and options for treatment", Respir Med., Jul. 2006, 100(7): 1139-1151.
Baturin et al., Micogenic sensibilization in patients having a controlled bronchial asthma, Scientific notes of Orel State University, No. 6, (56), pp. 187-191, 2013.
Beck et al., "Dupilumab Treatment for Generalized Prurigo Nodularis", JAMA Dermatol., Jan. 2019, 155(1): 118-120.
Bhatt et al., "Dupilumab for COPD with Type 2 Inflammation Indicated by Eosinophil Counts", NEJM, May 21, 2023, 389(3): 205-214.
Calugareanu et al., "Dramatic improvement of generalized prurigo nodularis with dupilumab", J Eur Acad Dermatol Venereol, Aug. 2019, 33(8): e303-e304.
Caswell-Smith et al., "Day-time variation of serum periostin in asthmatic adults treated with ICS/LABA and adults without asthma", Allergy Asthma Clin Immunol., 2017, 13: 8, Epublished Feb. 8, 2007.
ClinicalTrials.gov, "An Evaluation of Dupilumab in Patients With Moderate to Severe Uncontrolled Asthma", Clinical Trial Protocol Version 22, Feb. 3, 2014, ClinicalTrials.gov ID: NCT01854047.
Endo et al., "The Interleukin-33-p38 Kinase Axis Confers Memory T Helper 2 Cell Pathogenicity in the Airway", Immunity, Feb. 17, 2015, 42(2): 294-308.
Extended European Search Report for European Application No. 24150594.0, dated Jul. 5, 2024.
Goryachkina et al., Allergic bronchopulmonary aspergillosis, Allergiology, n.2, 2008, pp. 11-14.
Inoue et al., "Periostin as a biomarker for the diagnosis of pediatric asthma", Pediatr Allergy Asthma, Aug. 2016, 27(5): 521-526, Epublished Apr. 7, 2016.
International Search Report with Written Opinion for PCT International Patent Application No. PCT/US2024/020860 mailed Aug. 26, 2024, 2023.
Lee et al., "Inhibition of Murine Allergic Response by Monoclonal Interleukin-4 Receptor Antibody", J Rhinol., 2000, 7(2): 149-153.
Lee et al., "Targeting eosinophils in respiratory diseases: Biological axis, emerging therapeutics and treatment modalities", Life Sciences, 2018, 267: 118973.
Macharadze, Modern Clinical Aspects of total and Specific IGE evaluation, Pediatrics, 2017, vol. 96, No. 2, pp. 121-127.
Mollanazar et al., "Reduced Itch Associated with Dupilumab Treatment in 4 Patients with Prurigo Nodularis", JAMA Dermatology, Jan. 2019, 155(1): 121-122.
Notice of Opposition against European Patent No. 3973987 (Application No. 21191120.1) filed on Oct. 1, 2024, on behalf of Dr. H. Ulrich Dörries.
P1—U.S. Appl. No. 61/943,019 (Feb. 21, 2014), cited in Notice of Opposition against European Patent No. 3973987 (Application No. 21191120.1) filed on Oct. 1, 2024, on behalf of Dr. H. Ulrich Dörries.
P2—EP 14306413.7 (Sep. 15, 2014), cited in Notice of Opposition against European Patent No. 3973987 (Application No. 21191120.1) filed on Oct. 1, 2024, on behalf of Dr. H. Ulrich Dörries.
P3—U.S. Appl. No. 62/077,669 (Nov. 10, 2014), cited in Notice of Opposition against European Patent No. 3973987 (Application No. 21191120.1) filed on Oct. 1, 2024, on behalf of Dr. H. Ulrich Dörries.
WO—WO 2015/127229, parent application as filed, cited in Notice of Opposition against European Patent No. 3973987 (Application No. 21191120.1) filed on Oct. 1, 2024, on behalf of Dr. H. Ulrich Dörries.
D1—Wenzel et al., The New England Journal of Medicine, 368(26):2455-66, published online on May 21, 2013, cited in Notice of Opposition against European Patent No. 3973987 (Application No. 21191120.1) filed on Oct. 1, 2024, on behalf of Dr. H. Ulrich Dörries.
D1a—Supplementary Appendix to D1, published together with D1, cited in Notice of Opposition against European Patent No. 3973987 (Application No. 21191120.1) filed on Oct. 1, 2024, on behalf of Dr. H. Ulrich Dörries.
D2—Gibaldi M., "Biopharmaceutics and Clinical Pharmacokinetics", 4th Edition, 1991, Lea & Febiger, pp. 12-13, cited in Notice of Opposition against European Patent No. 3973987 (Application No. 21191120.1) filed on Oct. 1, 2024, on behalf of Dr. H. Ulrich Dörries.
D3—NCT01312961 clinical trial protocol, version 36, Jan. 13, 2014, cited in Notice of Opposition against European Patent No. 3973987 (Application No. 21191120.1) filed on Oct. 1, 2024, on behalf of Dr. H. Ulrich Dörries.
D4—NCT01854047 clinical trial protocol, version 23, Feb. 18, 2014, cited in Notice of Opposition against European Patent No. 3973987 (Application No. 21191120.1) filed on Oct. 1, 2024, on behalf of Dr. H. Ulrich Dörries.
D5—WO 2014/031610 A1, published on Feb. 27, 2014, cited in Notice of Opposition against European Patent No. 3973987 (Application No. 21191120.1) filed on Oct. 1, 2024, on behalf of Dr. H. Ulrich Dörries.
D6—Wenzel S. et al., Lancet, 388:31-44, published online on Apr. 26, 2016, cited in Notice of Opposition against European Patent No. 3973987 (Application No. 21191120.1) filed on Oct. 1, 2024, on behalf of Dr. H. Ulrich Dörries.
D7—pp. 401, 402 and 412 of WHO Drug Information, vol. 26, No. 4, 2012, cited in Notice of Opposition against European Patent No. 3973987 (Application No. 21191120.1) filed on Oct. 1, 2024, on behalf of Dr. H. Ulrich Dörries.
D8—EurekAlert!, press release; "Monoclonal antibody appears effective and safe in, cited in Notice of Opposition against European Patent No. 3973987 (Application No. 21191120.1) filed on Oct. 1, 2024, on behalf of Dr. H. Ulrich Dörries. asthma Phase IIa trial", May 21, 2013.
D9—Chapter 19, "Dosage regimens", of Aulton's Pharmaceutics: The Science of Dosage Form Design, 2nd Edition, 2001, cited in Notice of Opposition against European Patent No. 3973987 (Application No. 21191120.1) filed on Oct. 1, 2024, on behalf of Dr. H. Ulrich Dörries.
D10—Panaccione R. and Ghosh S., Therapeutic Advances in Gastroenterology, 3(3):179-189, published on May 2010, cited in Notice of Opposition against European Patent No. 3973987 (Application No. 21191120.1) filed on Oct. 1, 2024, on behalf of Dr. H. Ulrich Dörries.
D11—Press release from Regeneron Pharmaceuticals Inc., Mar. 2, 2013, cited in Notice of Opposition against European Patent No. 3973987 (Application No. 21191120.1) filed on Oct. 1, 2024, on behalf of Dr. H. Ulrich Dörries.
D12—Global Initiative for Asthma (GINA) Guidelines 2012, updated in 2012, cited in Notice of Opposition against European Patent No. 3973987 (Application No. 21191120.1) filed on Oct. 1, 2024, on behalf of Dr. H. Ulrich Dörries.
D13—Jin et al., Therapeutics and Clinical Risk Management, 4(1): 269-286, 2008, cited in Notice of Opposition against European Patent No. 3973987 (Application No. 21191120.1) filed on Oct. 1, 2024, on behalf of Dr. H. Ulrich Dörries.
D14—NCT01015027 clinical trial protocol, version 7, Jun. 13, 2013, cited in Notice of Opposition against European Patent No. 3973987 (Application No. 21191120.1) filed on Oct. 1, 2024, on behalf of Dr. H. Ulrich Dörries.
D15—NCT01484600 clinical trial protocol, version 2, Mar. 12, 2012, cited in Notice of Opposition against European Patent No. 3973987 (Application No. 21191120.1) filed on Oct. 1, 2024, on behalf of Dr. H. Ulrich Dorries.
D16—NCT01537653 clinical trial protocol, version 7, Dec. 5, 2013, cited in Notice of Opposition against European Patent No. 3973987 (Application No. 21191120.1) filed on Oct. 1, 2024, on behalf of Dr. H. Ulrich Dörries.
D17—NCT01537640 clinical trial protocol, version 6, Dec. 5, 2013, cited in Notice of Opposition against European Patent No. 3973987 (Application No. 21191120.1) filed on Oct. 1, 2024, on behalf of Dr. H. Ulrich Dörries.

(56) References Cited

OTHER PUBLICATIONS

D18—NCT01259323 clinical trial protocol, version 6, Oct. 2, 2012, cited in Notice of Opposition against European Patent No. 3973987 (Application No. 21191120.1) filed on Oct. 1, 2024, on behalf of Dr. H. Ulrich Dorries.
D19—NCT01385657 clinical trial protocol, version 4, Sep. 27, 2013, cited in Notice of Opposition against European Patent No. 3973987 (Application No. 21191120.1) filed on Oct. 1, 2024, on behalf of Dr. H. Ulrich Dörries.
Notice of Opposition against European Patent No. 3973987 (Application No. 21191120.1) filed on Oct. 9, 2024, on behalf of Secerna LLP.
D1—WHO Drug Information, vol. 26, No. 4, p. 412, Dec. 9, 2012, cited in Notice of Opposition against European Patent No. 3973987 (Application No. 21191120.1) filed on Oct. 9, 2024, on behalf of Secerna LLP.
D2—Wenzel et al., Dupilumab in persistent asthma with elevated eosinophil levels. N Engl J Med. 2013; 368(26): 2455-66, May 21, 2013, cited in Notice of Opposition against European Patent No. 3973987 (Application No. 21191120.1) filed on Oct. 9, 2024, on behalf of Secerna LLP.
D3—Protocol for: Wenzel et al. Dupilumab in persistent asthma with elevated eosinophil levels. N Engl J Med 2013; 368:2455-66, May 21, 2013, cited in Notice of Opposition against European Patent No. 3973987 (Application No. 21191120.1) filed on Oct. 9, 2024, on behalf of Secerna LLP.
D4—Study NCT01854047, An Evaluation of Dupilumab in Patients with Moderate to Severe Uncontrolled Asthma, Feb. 18, 2014, cited in Notice of Opposition against European Patent No. 3973987 (Application No. 21191120.1) filed on Oct. 9, 2024, on behalf of Secerna LLP.
D5—Press release: Sanofi and Regeneron Announce Positive Results from Phase 2b Study of Dupilumab in Patients with Moderate-to-Severe Asthma, https://investor.regeneron.com/news-releases/news-release-details/regeneron-and-sanofi-announce-positive-results-phase-2b-study-0, Nov. 11, 2014, cited in Notice of Opposition against European Patent No. 3973987 (Application No. 21191120.1) filed on Oct. 9, 2024, on behalf of Secerna LLP.
D6—WO 2014/031610 A1 published Feb. 27, 2014, cited in Notice of Opposition against European Patent No. 3973987 (Application No. 21191120.1) filed on Oct. 9, 2024, on behalf of Secerna LLP.
D7—Aulton. Pharmaceutics The Science of Dosage Form Design 2nd Edition. Chapter 19, 275-288, Oct. 2001, cited in Notice of Opposition against European Patent No. 3973987 (Application No. 21191120.1) filed on Oct. 9, 2024, on behalf of Secerna LLP.
D8—Panaccione & Ghosh. Optimal use of biologics in the management of Crohn's disease. Therapeutic Advances in Gastroenterology 2010, 3(3), 179-189, May 2010, cited in Notice of Opposition against European Patent No. 3973987 (Application No. 21191120.1) filed on Oct. 9, 2024, on behalf of Secerna LLP.
D9—Mould & Green, Pharmacokinetics and Pharmacodynamics of Monoclonal Antibodies. Concepts and Lessons for Drug Development, 2010, 24(1), 23-39, Feb. 1, 2010, cited in Notice of Opposition against European Patent No. 3973987 (Application No. 21191120.1) filed on Oct. 9, 2024, on behalf of Secerna LLP.
D10—Eisenstein. Something new under the skin. Nature Biotechnology 2011 29(2), 107-109, Feb. 7, 2011, cited in Notice of Opposition against European Patent No. 3973987 (Application No. 21191120.1) filed on Oct. 9, 2024, on behalf of Secerna LLP.
D11—Costantino et al., Intranasal delivery: Physicochemical and therapeutic, aspects, International Journal of Pharmaceutics, 2007, 337(1-2), Abstract, cited in Notice of Opposition against European Patent No. 3973987 (Application No. 21191120.1) filed on Oct. 9, 2024, on behalf of Secerna LLP.
D12—Gibaldi. Biopharmaceutics and clinical pharmacokinetics. Fourth Edition 1991. 12-13, cited in Notice of Opposition against European Patent No. 3973987 (Application No. 21191120.1) filed on Oct. 9, 2024, on behalf of Secerna LLP.
D13—Press Release: Sanofi and Regeneron Report Positive Proof-of-Concept Data for Dupilumab, an IL-4R alpha Antibody, in Atopic Dermatitis. https://investor.regeneron.com/news-releases/news-release-details/sanofi-and-regeneron-report-positive-proof-concept-data, Mar. 2, 2013, cited in Notice of Opposition against European Patent No. 3973987 (Application No. 21191120.1) filed on Oct. 9, 2024, on behalf of Secerna LLP.
D14—WO 2022/076289 A1 (pp. 1 to 4), published Apr. 14, 2022, cited in Notice of Opposition against European Patent No. 3973987 (Application No. 21191120.1) filed on Oct. 9, 2024, on behalf of Secerna LLP.
D15—Shannon et al. Differences in Airway Cytokine Profile in Severe Asthma Compared to Moderate Asthma, Chest 2007, 133(2), 420-6, Dec. 10, 2007., cited in Notice of Opposition against European Patent No. 3973987 (Application No. 21191120.1) filed on Oct. 9, 2024, on behalf of Secerna LLP.
D16—Bossley et al. Paediatric severe asthma is characterized by eosinophilia and remodelling without TH2 cytokines. J Allergy Clin Immunol. 2012, 129(4), 974-982, Apr. 2012, cited in Notice of Opposition against European Patent No. 3973987 (Application No. 21191120.1) filed on Oct. 9, 2024, on behalf of Secerna LLP.
D17—Emea. Annex I Summary of product characteristics for dupilumab, Sept. 2, 2022, cited in Notice of Opposition against European Patent No. 3973987 (Application No. 21191120.1) filed on Oct. 9, 2024, on behalf of Secerna LLP.
D18—Wenzel. Severe Asthma: from characteristics to phenotypes to endotypes. Clinical & Experimental Allergy 2012, 42, 650-658, Jan. 18, 2012, cited in Notice of Opposition against European Patent No. 3973987 (Application No. 21191120.1) filed on Oct. 9, 2024, on behalf of Secerna LLP.
D19—Wenzel. Severe Asthma in Adults. Am J Respir Crit Care Med. 2005 172(2) 149-160, cited in Notice of Opposition against European Patent No. 3973987 (Application No. 21191120.1) filed on Oct. 9, 2024, on behalf of Secerna LLP.
D20—Nakawah et al. Asthma, Chronic Obstructive Pulmonary Disease (COPD), and the Overlap Syndrome. 2013 J Am Board Fam Med 2013 26:4 470-477, Jul. 2013, cited in Notice of Opposition against European Patent No. 3973987 (Application No. 21191120.1) filed on Oct. 9, 2024, on behalf of Secerna LLP.
D21—Firszt & Kraft, Pharmacotherapy of severe asthma. Curr Opin Pharmacol. 2010. 10(3), 266-271, Jun. 2010, cited in Notice of Opposition against European Patent No. 3973987 (Application No. 21191120.1) filed on Oct. 9, 2024, on behalf of Secerna LLP.
D22—Al-Ramli et al. Th-17 cell-related cytokines' potential role in the pathogenesis of severe asthma. J Asthma. 2008 45, Suppl 1: 41-44, Jul. 2, 2009, cited in Notice of Opposition against European Patent No. 3973987 (Application No. 21191120.1) filed on Oct. 9, 2024, on behalf of Secerna LLP.
D23—Jennifer D Hamilton et al. Biomarkers elevated in atopic dermatitis (AD) are reduced by therapeutic blockade of IL-4 receptor alpha signalling with patients with moderate-to-severe AD. Abstract 1042, International Investigative Dermatology, XP055566280,, cited in Notice of Opposition against European Patent No. 3973987 (Application No. 21191120.1) filed on Oct. 9, 2024, on behalf of Secerna LLP. Edinburgh, May 8, 2013.
D24—EMEA Guideline for Industry—dose-response information to support drug registration ICH-E4, Nov. 1994, cited in Notice of Opposition against European Patent No. 3973987 (Application No. 21191120.1) filed on Oct. 9, 2024, on behalf of Secerna LLP.
D25—Dirks & Meibohm. Population Pharmacokinetics of Therapeutic Monoclonal Antibodies. Clin. Pharmacokinet. 2010; 49 (10) 633-659, cited in Notice of Opposition against European Patent No. 3973987 (Application No. 21191120.1) filed on Oct. 9, 2024, on behalf of Secerna LLP.
D26—Bai et al. A guide to rational dosing of monoclonal antibodies. Clin. Pharmacokinet. 2012, 52(2)119-135, cited in Notice of Opposition against European Patent No. 3973987 (Application No. 21191120.1) filed on Oct. 9, 2024, on behalf of Secerna LLP.
P1—U.S. Appl. No. 61/943,019 (Provisional), filed on Feb. 21, 2014, cited in Notice of Opposition against European Patent No. 3973987 (Application No. 21191120.1) filed on Oct. 9, 2024, on behalf of Secerna LLP.
P2—EP 14306413.7, filed on Sep. 15, 2014, cited in Notice of Opposition against European Patent No. 3973987 (Application No. 21191120.1) filed on Oct. 9, 2024, on behalf of Secerna LLP.

(56) References Cited

OTHER PUBLICATIONS

P3—U.S. Appl. No. 62/077,669 (Provisional), filed on Nov. 10, 2014, cited in Notice of Opposition against European Patent No. 3973987 (Application No. 21191120.1) filed on Oct. 9, 2024, on behalf of Secerna LLP.
A—Divisional application as filed, Apr. 30, 2022, cited in Notice of Opposition against European Patent No. 3973987 (Application No. 21191120.1) filed on Oct. 9, 2024, on behalf of Secerna LLP.
Notice of Opposition against European Patent No. 3973987 (Application No. 21191120.1) filed on Oct. 10, 2024, on behalf of Dr. Luigi Rumi.
TM1—WO 2015/127229 A1, published Aug. 27, 2015, cited in Notice of Opposition against European Patent No. 3973987 (Application No. 21191120.1) filed on Oct. 10, 2024, on behalf of Dr. Luigi Rumi.
TM2—U.S. Appl. No. 61/943,019 (Provisional), filed on Feb. 21, 2014, cited in Notice of Opposition against European Patent No. 3973987 (Application No. 21191120.1) filed on Oct. 10, 2024, on behalf of Dr. Luigi Rumi.
TM3—EP 14306413, filed on Sep. 15, 2014, cited in Notice of Opposition against European Patent No. 3973987 (Application No. 21191120.1) filed on Oct. 10, 2024, on behalf of Dr. Luigi Rumi.
TM4—U.S. Appl. No. 62/077,669 (Provisional), filed on Nov. 10, 2014, cited in Notice of Opposition against European Patent No. 3973987 (Application No. 21191120.1) filed on Oct. 10, 2024, on behalf of Dr. Luigi Rumi.
TM5—EP 3973987 A1, published Mar. 30, 2022 (divisional application as filed resulting in the opposed patent) , cited in Notice of Opposition against European Patent No. 3973987 (Application No. 21191120.1) filed on Oct. 10, 2024, on behalf of Dr. Luigi Rumi.
TM6—WHO Drug Information vol. 26(4), 412, Dec. 9, 2012, cited in Notice of Opposition against European Patent No. 3973987 (Application No. 21191120.1) filed on Oct. 10, 2024, on behalf of Dr. Luigi Rumi.
TM7—Regeneron press release, "Sanofi and Regeneron report positive proof-of- concept data for dupilumab, an IL-4R alpha antibody in atopic dermatitis", Mar. 2, 2013, cited in Notice of Opposition against European Patent No. 3973987 (Application No. 21191120.1) filed on Oct. 10, 2024, on behalf of Dr. Luigi Rumi.
TM8—Pollart S.M. and Elward K.S. Overview of changes to asthma guidelines: diagnosis and screening. Am Fam Physician. May 1, 2009;79(9):761-7, cited in Notice of Opposition against European Patent No. 3973987 (Application No. 21191120.1) filed on Oct. 10, 2024, on behalf of Dr. Luigi Rumi.
TM9—"Global Strategy for Asthma Management and Prevention", Global Initiative for Asthma (GINA), 2011, cited in Notice of Opposition against European Patent No. 3973987 (Application No. 21191120.1) filed on Oct. 10, 2024, on behalf of Dr. Luigi Rumi.
TM10—Wenzel S. et al. Dupilumab in persistent asthma with elevated eosinophil levels. N Engl J Med. Jun. 2, 20137;368(26):2455-66. doi: 10.1056/NEJMoa1304048. Epub May 21, 2013, cited in Notice of Opposition against European Patent No. 3973987 (Application No. 21191120.1) filed on Oct. 10, 2024, on behalf of Dr. Luigi Rumi.
TM11—Mutschler Arzneimittelwirkungen—Lehrbuch der Pharmakologie and Toxikologie, p. 83, 3.3.1 Dosierung, "Initialdosis, Erhaltungsdosis", cited in Notice of Opposition against European Patent No. 3973987 (Application No. 21191120.1) filed on Oct. 10, 2024, on behalf of Dr. Luigi Rumi.
TM12—NCT01854047, Feb. 18, 2014 (v23) , cited in Notice of Opposition against European Patent No. 3973987 (Application No. 21191120.1) filed on Oct. 10, 2024, on behalf of Dr. Luigi Rumi.
TM13—WO 2014/031610 A1, published Feb. 27, 2014, cited in Notice of Opposition against European Patent No. 3973987 (Application No. 21191120.1) filed on Oct. 10, 2024, on behalf of Dr. Luigi Rumi.
Notice of Opposition against European Patent No. 3973987 (Application No. 21191120.1) filed on Oct. 10, 2024, on behalf of Boult Wade Tennant LLP.
PA—Text of EP 21191120.1—divisional application as originally filed, cited in Notice of Opposition against European Patent No. 3973987 (Application No. 21191120.1) filed on Oct. 10, 2024, on behalf of Boult Wade Tennant LLP.
WO229—WO 2015/127229, published Aug. 27, 2015—PCT publication of the parent application, cited in Notice of Opposition against European Patent No. 3973987 (Application No. 21191120.1) filed on Oct. 10, 2024, on behalf of Boult Wade Tennant LLP.
D1—Wenzel et al., "Dupilumab in Persistent Asthma with Elevated Eosinophil Levels" New England Journal of Medicine, vol. 368 No. 26: 2455-2466, Jun. 27, 2013, cited in Notice of Opposition against European Patent No. 3973987 (Application No. 21191120.1) filed on Oct. 10, 2024, on behalf of Boult Wade Tennant LLP.
D2—Supplementary Appendix of Wenzel, 2013 (D1) , cited in Notice of Opposition against European Patent No. 3973987 (Application No. 21191120.1) filed on Oct. 10, 2024, on behalf of Boult Wade Tennant LLP.
D3—NCT01854047 "An evaluation of dupilumab in subjects with moderate to severe uncontrolled asthma", Clinical trial study record, Version 23, Feb. 18, 2014, cited in Notice of Opposition against European Patent No. 3973987 (Application No. 21191120.1) filed on Oct. 10, 2024, on behalf of Boult Wade Tennant LLP.
D4—U.S. Pat. No. 8,075,887 B2, issued Dec. 13, 2011, cited in Notice of Opposition against European Patent No. 3973987 (Application No. 21191120.1) filed on Oct. 10, 2024, on behalf of Boult Wade Tennant LLP.
D5—GINA Guidelines, 2009, cited in Notice of Opposition against European Patent No. 3973987 (Application No. 21191120.1) filed on Oct. 10, 2024, on behalf of Boult Wade Tennant LLP.
D6—WHO Drug Information, vol. 26, No. 4, pp. 401-402 and 412, extract from "Proposed INN: List 108", published on Dec. 9, 2012, cited in Notice of Opposition against European Patent No. 3973987 (Application No. 21191120.1) filed on Oct. 10, 2024, on behalf of Boult Wade Tennant LLP.
D7—Radin, et al., Abstract 558, J Clin Immunol., Feb. 2013, cited in Notice of Opposition against European Patent No. 3973987 (Application No. 21191120.1) filed on Oct. 10, 2024, on behalf of Boult Wade Tennant LLP.
D8—Hashimoto and Bel, "Current treatment of severe asthma", Clinical & Experimental Allergy, vol. 42, pp. 693-705, 2012, cited in Notice of Opposition against European Patent No. 3973987 (Application No. 21191120.1) filed on Oct. 10, 2024, on behalf of Boult Wade Tennant LLP.
D9—Regeneron Press Release, May 21, 2013, cited in Notice of Opposition against European Patent No. 3973987 (Application No. 21191120.1) filed on Oct. 10, 2024, on behalf of Boult Wade Tennant LLP.
D10—Eurekalert! Press Release, "Monoclonal antibody appears effective and safe in asthma Phase IIa trial", May 21, 2013, cited in Notice of Opposition against European Patent No. 3973987 (Application No. 21191120.1) filed on Oct. 10, 2024, on behalf of Boult Wade Tennant LLP.
D11—Mould and Green, "Pharmacokinetics and Pharmacodynamics of Monoclonal Antibodies", Biodrugs, vol. 24(1), pp. 23-39, 2010, cited in Notice of Opposition against European Patent No. 3973987 (Application No. 21191120.1) filed on Oct. 10, 2024, on behalf of Boult Wade Tennant LLP.
D12—Galli et al., "Atopic Dermatitis and Asthma", Allergy Asthma Proc., vol. 28, pp. 540-543, 2007, cited in Notice of Opposition against European Patent No. 3973987 (Application No. 21191120.1) filed on Oct. 10, 2024, on behalf of Boult Wade Tennant LLP.
D13—NCT01312961 clinical trial study record, Version 36, Jan. 13, 2014, cited in Notice of Opposition against European Patent No. 3973987 (Application No. 21191120.1) filed on Oct. 10, 2024, on behalf of Boult Wade Tennant LLP.
D14—NCT01015027 clinical trial study record, Version 7, Jun. 13, 2013, cited in Notice of Opposition against European Patent No. 3973987 (Application No. 21191120.1) filed on Oct. 10, 2024, on behalf of Boult Wade Tennant LLP.
D15—NCT01484600 clinical trial study record, Version 2, Mar. 12, 2012, cited in Notice of Opposition against European Patent No. 3973987 (Application No. 21191120.1) filed on Oct. 10, 2024, on behalf of Boult Wade Tennant LLP.

(56) References Cited

OTHER PUBLICATIONS

D16—NCT01537653 clinical trial study record, Version 7, Dec. 5, 2013, cited in Notice of Opposition against European Patent No. 3973987 (Application No. 21191120.1) filed on Oct. 10, 2024, on behalf of Boult Wade Tennant LLP.
D17—NCT01537640 clinical trial study record, Version 6, Dec. 5, 2013, cited in Notice of Opposition against European Patent No. 3973987 (Application No. 21191120.1) filed on Oct. 10, 2024, on behalf of Boult Wade Tennant LLP.
D18—NCT01259323 clinical trial study record, Version 6, Oct. 2, 2012, cited in Notice of Opposition against European Patent No. 3973987 (Application No. 21191120.1) filed on Oct. 10, 2024, on behalf of Boult Wade Tennant LLP.
D19—NCT01385657 clinical trial study record, Version 4, Sep. 27, 2013, cited in Notice of Opposition against European Patent No. 3973987 (Application No. 21191120.1) filed on Oct. 10, 2024, on behalf of Boult Wade Tennant LLP.
P1—U.S. Appl. No. 61/943,019 (Provisional), filed on Feb. 21, 2014, cited in Notice of Opposition against European Patent No. 3973987 (Application No. 21191120.1) filed on Oct. 10, 2024, on behalf of Boult Wade Tennant LLP.
P2—EP 14306413.7, filed on Sep. 15, 2014, cited in Notice of Opposition against European Patent No. 3973987 (Application No. 21191120.1) filed on Oct. 10, 2024, on behalf of Boult Wade Tennant LLP.
P3—U.S. Appl. No. 62/077,669 (Provisional), filed on Nov. 10, 2014, cited in Notice of Opposition against European Patent No. 3973987 (Application No. 21191120.1) filed on Oct. 10, 2024, on behalf of Boult Wade Tennant LLP.
Notice of Opposition against European Patent No. 3973987 (Application No. 21191120.1) filed on Oct. 10, 2024, on behalf of Michaelski Hüttermann & Partner Patentanwalte mbD.
D1—Wenzel et al., 2013, cited in Notice of Opposition against European Patent No. 3973987 (Application No. 21191120.1) filed on Oct. 10, 2024, on behalf of Michaelski Hüttermann & Partner Patentanwalte mbD.
D2—Steinke et Borish, 2002, cited in Notice of Opposition against European Patent No. 3973987 (Application No. 21191120.1) filed on Oct. 10, 2024, on behalf of Michaelski Hüttermann & Partner Patentanwalte mbD.
D3—Wenzel et al., 2007, cited in Notice of Opposition against European Patent No. 3973987 (Application No. 21191120.1) filed on Oct. 10, 2024, on behalf of Michaelski Hüttermann & Partner Patentanwalte mbD.
D4—Corren et al., 2010, cited in Notice of Opposition against European Patent No. 3973987 (Application No. 21191120.1) filed on Oct. 10, 2024, on behalf of Michaelski Hüttermann & Partner Patentanwalte mbD.
D5—U.S. Pat. No. 2003185821, cited in Notice of Opposition against European Patent No. 3973987 (Application No. 21191120.1) filed on Oct. 10, 2024, on behalf of Michaelski Hüttermann & Partner Patentanwalte mbD.
D6—Pollart et al., 2009, cited in Notice of Opposition against European Patent No. 3973987 (Application No. 21191120.1) filed on Oct. 10, 2024, on behalf of Michaelski Hüttermann & Partner Patentanwalte mbD.
D7—Wenzel et al., 2005, cited in Notice of Opposition against European Patent No. 3973987 (Application No. 21191120.1) filed on Oct. 10, 2024, on behalf of Michaelski Huttermann & Partner Patentanwalte mbD.
D8—Study Record Version 22 of clinical trial NCT01854047, Feb. 3, 2014, cited in Notice of Opposition against European Patent No. 3973987 (Application No. 21191120.1) filed on Oct. 10, 2024, on behalf of Michaelski Hüttermann & Partner Patentanwalte mbD.
D9—Ramli et al., 2008, cited in Notice of Opposition against European Patent No. 3973987 (Application No. 21191120.1) filed on Oct. 10, 2024, on behalf of Michaelski Hüttermann & Partner Patentanwalte mbD.
D10—EP 3470432 A1, published Mar. 30, 2022, cited in Notice of Opposition against European Patent No. 3973987 (Application No. 21191120.1) filed on Oct. 10, 2024, on behalf of Michaelski Huttermann & Partner Patentanwalte mbD.
D11—Chames et al. 2009, cited in Notice of Opposition against European Patent No. 3973987 (Application No. 21191120.1) filed on Oct. 10, 2024, on behalf of Michaelski Hüttermann & Partner Patentanwalte mbD.
D12—Bumbacea et al., 2004, cited in Notice of Opposition against European Patent No. 3973987 (Application No. 21191120.1) filed on Oct. 10, 2024, on behalf of Michaelski Hüttermann & Partner Patentanwalte mbD.
D13—Jenkins et al., 2003, cited in Notice of Opposition against European Patent No. 3973987 (Application No. 21191120.1) filed on Oct. 10, 2024, on behalf of Michaelski Hüttermann & Partner Patentanwalte mbD.
D14—Reasons for the decision in the parent patent (EP 15708991.3); dated Mar. 7, 2024, cited in Notice of Opposition against European Patent No. 3973987 (Application No. 21191120.1) filed on Oct. 10, 2024, on behalf of Michaelski Hüttermann & Partner Patentanwalte mbD.
D15—Greulich et al., 2010, cited in Notice of Opposition against European Patent No. 3973987 (Application No. 21191120.1) filed on Oct. 10, 2024, on behalf of Michaelski Hüttermann & Partner Patentanwalte mbD.
D16—Birkett et al., 1996, cited in Notice of Opposition against European Patent No. 3973987 (Application No. 21191120.1) filed on Oct. 10, 2024, on behalf of Michaelski Hüttermann & Partner Patentanwalte mbD.
D17—Pavord et al., 2012, cited in Notice of Opposition against European Patent No. 3973987 (Application No. 21191120.1) filed on Oct. 10, 2024, on behalf of Michaelski Hüttermann & Partner Patentanwalte mbD.
D18—Bousquet et al., 1990, cited in Notice of Opposition against European Patent No. 3973987 (Application No. 21191120.1) filed on Oct. 10, 2024, on behalf of Michaelski Huttermann & Partner Patentanwalte mbD.
D19—Haldar et al., 2009, cited in Notice of Opposition against European Patent No. 3973987 (Application No. 21191120.1) filed on Oct. 10, 2024, on behalf of Michaelski Hüttermann & Partner Patentanwalte mbD.
D20—List of approved antibodies until 2014, cited in Notice of Opposition against European Patent No. 3973987 (Application No. 21191120.1) filed on Oct. 10, 2024, on behalf of Michaelski Hüttermann & Partner Patentanwalte mbD.
D21—Convolutum of clinical trial protolcols completed before the priority date, cited in Notice of Opposition against European Patent No. 3973987 (Application No. 21191120.1) filed on Oct. 10, 2024, on behalf of Michaelski Hüttermann & Partner Patentanwalte mbD.
D22—Tan et al., 2006, cited in Notice of Opposition against European Patent No. 3973987 (Application No. 21191120.1) filed on Oct. 10, 2024, on behalf of Michaelski Hüttermann & Partner Patentanwalte mbD.
D23—Onrust et al., 1999, cited in Notice of Opposition against European Patent No. 3973987 (Application No. 21191120.1) filed on Oct. 10, 2024, on behalf of Michaelski Hüttermann & Partner Patentanwalte mbD.
D24—Spratlin et al., 2010, cited in Notice of Opposition against European Patent No. 3973987 (Application No. 21191120.1) filed on Oct. 10, 2024, on behalf of Michaelski Huttermann & Partner Patentanwalte mbD.
D25—Chmielowski, 2013, cited in Notice of Opposition against European Patent No. 3973987 (Application No. 21191120.1) filed on Oct. 10, 2024, on behalf of Michaelski Hüttermann & Partner Patentanwalte mbD.
D26—Cohenuram and Saif, 2007, cited in Notice of Opposition against European Patent No. 3973987 (Application No. 21191120.1) filed on Oct. 10, 2024, on behalf of Michaelski Hüttermann & Partner Patentanwalte mbD.
D27—Rau, 2002, cited in Notice of Opposition against European Patent No. 3973987 (Application No. 21191120.1) filed on Oct. 10, 2024, on behalf of Michaelski Hüttermann & Partner Patentanwalte mbD.

(56) References Cited

OTHER PUBLICATIONS

D28—Metzger-Filho, 2013, cited in Notice of Opposition against European Patent No. 3973987 (Application No. 21191120.1) filed on Oct. 10, 2024, on behalf of Michaelski Hüttermann & Partner Patentanwalte mbD.
D29—Frampton, 2013, cited in Notice of Opposition against European Patent No. 3973987 (Application No. 21191120.1) filed on Oct. 10, 2024, on behalf of Michaelski Hüttermann & Partner Patentanwalte mbD.
D30—Leyland-Jones, 2003, cited in Notice of Opposition against European Patent No. 3973987 (Application No. 21191120.1) filed on Oct. 10, 2024, on behalf of Michaelski Hüttermann & Partner Patentanwalte mbD.
D31—Washburn et al., 2006, cited in Notice of Opposition against European Patent No. 3973987 (Application No. 21191120.1) filed on Oct. 10, 2024, on behalf of Michaelski Hüttermann & Partner Patentanwalte mbD.
D32—WO 2014/031610 A1, published on Feb. 27, 2014, cited in Notice of Opposition against European Patent No. 3973987 (Application No. 21191120.1) filed on Oct. 10, 2024, on behalf of Michaelski Hüttermann & Partner Patentanwalte mbD.
D33—Wang et al., 2008, cited in Notice of Opposition against European Patent No. 3973987 (Application No. 21191120.1) filed on Oct. 10, 2024, on behalf of Michaelski Huttermann & Partner Patentanwalte mbD.
D34—Mould and Sweeney 2007, cited in Notice of Opposition against European Patent No. 3973987 (Application No. 21191120.1) filed on Oct. 10, 2024, on behalf of Michaelski Huttermann & Partner Patentanwalte mbD.
Notice of Opposition against European Patent No. 3973987 (Application No. 21191120.1) filed on Oct. 10, 2024, on behalf of Hampton Knowles Limited.
D1—Wenzel et al., N. Engl. J. Med., 2013, 368(26):2455-2466, cited in Notice of Opposition against European Patent No. 3973987 (Application No. 21191120.1) filed on Oct. 10, 2024, on behalf of Hampton Knowles Limited.
D5—WO 2014/031610 A1, published Feb. 27, 2014, cited in Notice of Opposition against European Patent No. 3973987 (Application No. 21191120.1) filed on Oct. 10, 2024, on behalf of Hampton Knowles Limited.
D7—pp. 401, 402 and 412 of WHO Drug Information, 2012, 26(4):401- 471, cited in Notice of Opposition against European Patent No. 3973987 (Application No. 21191120.1) filed on Oct. 10, 2024, on behalf of Hampton Knowles Limited.
D8—EurekAlert! press release "Monoclonal antibody appears effective and safe in asthma Phase lla trial", May 21, 2013, cited in Notice of Opposition against European Patent No. 3973987 (Application No. 21191120.1) filed on Oct. 10, 2024, on behalf of Hampton Knowles Limited.
D9—Chapter 19, "Dosage regimens", of Aulton's Pharmaceutics: The Science of Dosage Form Design, 2nd Edition, 2001, cited in Notice of Opposition against European Patent No. 3973987 (Application No. 21191120.1) filed on Oct. 10, 2024, on behalf of Hampton Knowles Limited.
D10—Panaccione and Ghosh, Ther. Adv. Gastroenterol., 2010, 3(3):179- 189, which is a review article relating to the optimal use of biologics in the inflammatory disorder, Crohn's disease, cited in Notice of Opposition against European Patent No. 3973987 (Application No. 21191120.1) filed on Oct. 10, 2024, on behalf of Hampton Knowles Limited.
D11—Regeneron press release "Sanofi and Regeneron report positive proof- of- concept data for dupilumab, an Il- 4R alpha antibody, in atopic dermatitis", dated Mar. 2, 2013, cited in Notice of Opposition against European Patent No. 3973987 (Application No. 21191120.1) filed on Oct. 10, 2024, on behalf of Hampton Knowles Limited.
DYC01—pp. 159 to 162 of Rispens and Vidarsson, Antibody Fc: Linking Adaptive and Innate Immunity, Chapter 9, "Human IgG Subclasses", pp. 159 to 162, 2013; and evidence of its publication date, cited in Notice of Opposition against European Patent No. 3973987 (Application No. 21191120.1) filed on Oct. 10, 2024, on behalf of Hampton Knowles Limited.
DYC02—Interlocutory decision in Opposition proceedings for EP3107575B, dated Mar. 7, 2024, cited in Notice of Opposition against European Patent No. 3973987 (Application No. 21191120.1) filed on Oct. 10, 2024, on behalf of Hampton Knowles Limited.
DYC03—NCT01854047 clinical trial protocol version 22 (Feb. 3, 2014) , cited in Notice of Opposition against European Patent No. 3973987 (Application No. 21191120.1) filed on Oct. 10, 2024, on behalf of Hampton Knowles Limited.
DYC04—Regeneron press release "Sanofi and Regeneron announce publication of positive Phase 2A results of dupilumab in asthma in the New England Journal of Medicine", May 21, 2013, cited in Notice of Opposition against European Patent No. 3973987 (Application No. 21191120.1) filed on Oct. 10, 2024, on behalf of Hampton Knowles Limited.
DYC05—Swanson et al., World Allergy Organization Journal, 2014, 7(Suppl 1):P13, poster abstract 1023, cited in Notice of Opposition against European Patent No. 3973987 (Application No. 21191120.1) filed on Oct. 10, 2024, on behalf of Hampton Knowles Limited.
DYC06—Radin et al., J Allergy Clin Immunol, 2013, 131(2_ Suppl):AB158, abstract 558, cited in Notice of Opposition against European Patent No. 3973987 (Application No. 21191120.1) filed on Oct. 10, 2024, on behalf of Hampton Knowles Limited.
DYC07—Mould and Sweeney, Current Opinion in Drug Discovery & Development, 2007, 10(1):84- 96, cited in Notice of Opposition against European Patent No. 3973987 (Application No. 21191120.1) filed on Oct. 10, 2024, on behalf of Hampton Knowles Limited.
DYC08—Wang et al., Clinical Pharmacology & Therapeutics, 2008, 84(5):548- 558, cited in Notice of Opposition against European Patent No. 3973987 (Application No. 21191120.1) filed on Oct. 10, 2024, on behalf of Hampton Knowles Limited.
DYC09—Fracasso et al., Clin Cancer Res, 2007, 13(3):986- 993, cited in Notice of Opposition against European Patent No. 3973987 (Application No. 21191120.1) filed on Oct. 10, 2024, on behalf of Hampton Knowles Limited.
DYC10—Mould et al., Br J Clin Pharmacol, 2007, 64(3):278- 291, cited in Notice of Opposition against European Patent No. 3973987 (Application No. 21191120.1) filed on Oct. 10, 2024, on behalf of Hampton Knowles Limited.
DYC11—Sohn et al., Br J Clin Pharmacol, 2014, 78(3):477- 487, cited in Notice of Opposition against European Patent No. 3973987 (Application No. 21191120.1) filed on Oct. 10, 2024, on behalf of Hampton Knowles Limited.
DYC12—Dostalek et al., Clin Pharmacokinet, 2013, 52:83- 124, cited in Notice of Opposition against European Patent No. 3973987 (Application No. 21191120.1) filed on Oct. 10, 2024, on behalf of Hampton Knowles Limited.
DYC13—Corren et al., Am. J. Respir. Crit. Care Med., 2010, 181:788- 796, cited in Notice of Opposition against European Patent No. 3973987 (Application No. 21191120.1) filed on Oct. 10, 2024, on behalf of Hampton Knowles Limited.
DYC14—Borish, Am. J. Respir. Crit. Care Med., 2010, 181:769-772, cited in Notice of Opposition against European Patent No. 3973987 (Application No. 21191120.1) filed on Oct. 10, 2024, on behalf of Hampton Knowles Limited.
DYC15—Wenzel, Clinical & Experimental Allergy, 2012, 42:650-658, cited in Notice of Opposition against European Patent No. 3973987 (Application No. 21191120.1) filed on Oct. 10, 2024, on behalf of Hampton Knowles Limited.
DYC16—Hashimoto, The Lancet, 2012, 380:626- 627, cited in Notice of Opposition against European Patent No. 3973987 (Application No. 21191120.1) filed on Oct. 10, 2024, on behalf of Hampton Knowles Limited.
DYC17—Szefler et al., J Allergy Clin Immunol, 2012, 129:S9- 23, cited in Notice of Opposition against European Patent No. 3973987 (Application No. 21191120.1) filed on Oct. 10, 2024, on behalf of Hampton Knowles Limited.
Patentee's Response to opponents' submissions under Rule 116 EPC regarding European Patent No. 3703818 (EP Application No. 18799655.8), filed on behalf of Sanofi Biotechnology, dated Feb. 9, 2026.

(56) References Cited

OTHER PUBLICATIONS

D84—Second Declaration of Prof. Ian Pavord, Feb. 9, 2026.
D85—Chung et al., 2014; International ERS/ATS Guidelines on Defintion, Evaluation and Treatment of Severe Asthma, Eur. Respir. J.; 43; pp. 343-373.
D86—Broerson et al., "Adrenal insufficiency in corticosteroids use: systematic review and meta-analysis", The Journal of Clinical Endocrinology & Metabolism, Jun. 1, 2015, 100(6): 2171-2180.
D87—Daley-Yates, "Inhaled corticosteroids: potency, dose equivalence and therapeutic index", British Journal of Pharmacology, Mar. 14, 2015, 80(3): 372-380.
D88—Joseph et al., "Systemic glucocorticoid therapy and adrenal insufficiency in adults: a systematic review", Seminars in Arthritis and Rheumatism, Aug. 2016, 46(1): 133-141.
D23a—Protocol for: Wenzel et al., Dupilumab in persistent asthma with elevated eosinophil levels, N Engl J Med., May 21, 2013, 368(26): 2455-2466.
Response to Patentee's submission under Rule 116 EPC dated Dec. 23, 2025, regarding European Patent No. 3703818 (EP Application No. 18799655.8), filed on behalf of Dr. Luigi Rumi, dated Feb. 13, 2026.
D89—Second Declaration and CV of Prof. M.D. Ph.D. Dsc Felix JF Herth, dated Feb. 19, 2026.
List of Consolidated References for Written Submissions and Patentee's Submission regarding European Patent No. 4011915 (EP Application No. 21199451.2), dated Mar. 2, 2026.
D89—Excerpt from ClinicalTrials.gov Study NCT01312961 (v30), Efficacy, Safety, and Tolerability of SAR231893 (REGN668) in Patients with Persistent Moderate to Severe Eosinophilic Asthma, Jul. 25, 2012.
Aldington, S. et al., "Asthma exacerbations .5: Assessment and management of severe asthma in adults in hospital", Thorax, May 1, 2007, 62(5): 447-458.
Alotaibi et al., "Dupilumab as a treatment for allergic fungal rhinosinusitis: a case series", Rhinology Online, Aug. 11, 2023, 6(18): 18-24.
Center for Drug Evaluation and Research, (Jun. 26, 2019) "Approval Package for Dupixent Solution for Injection", Application No. 761055Orig1s014, Generic Name: dupilumab, Sponsored by Regeneron Pharmaceuticals, Inc.
Chong et al., "Biologics for chronic rhinosinusitis", Cochrane Database Syst. Rev., Feb. 27, 2020, 2(2): CD013513.
Clinicaltrials.gov, (Aug. 31, 2022) "A Study to Investigate the Pharmacokinetics and Safety of Dupilumab in Participants >2 Years to <12 Years of Age With Uncontrolled Chronic Spontaneous Urticaria (CSU) (LIBERTY-CSU CUPIDKids)", Study History, ClinicalTrials.gov Identifier: NCT05526521, https://clinicaltrials.gov/study/NCT05526521?term=nct05526521&rank=1&tab=history.
Diamant et al., "Biomarkers in asthma and allergic rhinitis", Pulmonary Pharmacology & Therapeutics, Dec. 2010, 23(6): 468-481, Epublished Jun. 30, 2010.
Ferrucci et al., "Rapid disappearance of both severe atopic dermatitis and cold urticaria following dupilumab treatment", Clin. Exp. Dermatol., Apr. 2020, 45(3):345-346. Epub Sep. 12, 2019.
Hox et al., "Benefits and harm of systemic steroids for short- and long-term use in rhinitis and rhinosinusitis: an EAACI position paper", Clin. Transl. Allergy, Sep. 28, 2020, 10: 38.
International Search Report and Written Opinion of PCT International Patent Application No. PCT/EP2023/073630, mailed Feb. 15, 2024.
International Search Report and Written Opinion of PCT International Patent Application No. PCT/EP2025/024486, mailed Jul. 24, 2025.
Kolkhir et al., "New Treatments for Chronic Urticaria", Ann. Allergy Asthma Immunol., Jan. 2020, 124(1): 2-12. Epub Aug. 23, 2019.
Le Floch et al., "Dual blockade of IL-4 and IL-13 with dupilumab, an IL-4Rα antibody, is required to broadly inhibit type 2 inflammation", Allergy, May 2020, 75(5)(: 1188-1204, Epublished Jan. 3, 2020.
Lee et al., "237: A Study of Dupilumab in Adults with CRSsNP: Results from the Liberty ORION study", J. Allergy and Clin. Immunol., Feb. 2025, 155(2 Suppl.): AB76.
Maltseva et al., "Cold urticaria—What we know and what we do not know", Allergy, Apr. 2021, 76(4): 1077-1094. Epub Dec. 24, 2020.
Matsumoto, "Serum periostin: a novel biomarker for asthma management", Allergol Int., Jun. 2014, 63(2): 153-160, Epub Apr. 25, 2014. doi: 10.2332/allergolint. 13-RAI-0678.
Oka et al., "A case of intractable chronic rhinosinusitis without nasal polyps leading remission after treatment switching from anti-IL-5 to anti-IL-4Rα monoclonal antibody", Otolaryngology Case Reports, Jun. 2023, 27: 100512.
Notice of Opposition against European Patent No. 4011915 (Application No. 21199451.2) dated Oct. 16, 2023, filed on behalf of Dr. Luigi Rumi.
Letter from the Opponent regarding the Opposition against European Patent No. 4011915 (Application No. 21199451.2), dated Jul. 14, 2025, filed on behalf of Dr. Luigi Rumi.
TM1—WO 2014/031610, grandparent application as filed, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM9—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108), cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM11—Pollart SM, et al. Am Fam Physician. May 1, 2009;79(9):761-7. 2009, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM12—Wenzel S., Clinical and Experimental Allergy, 42(5): 650-8, published on Jan. 18, 2012 (as evidenced by the Annex appended to the document), cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM13—Wenzel S.E., Nature Medicine, 18(5): 716-25, May 4, 2012, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM14—Wenzel S. Am J Respir Crit Care Med. Jul. 15, 2005;172(2):149-60. 2005, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM15—Global Initiative for Asthma (GINA) Guidelines 2012; updated until Jun. 30, 2012, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM16—Taylor D.R. et al., "A new perspective on concepts of asthma severity and control", Eur Respir J. Sep. 2008;32(3):545-54, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM17—Woodruff P.G. et al., "T-helper type 2-driven inflammation defines major subphenotypes of asthma", Am J Respir Crit Care Med. Sep. 1, 2009;180(5):388-95, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.
TM18—Liang Z. et al., "Moderate accuracy of peripheral eosinophil count for predicting eosinophilic phenotype in steroid-nai've

(56) References Cited

OTHER PUBLICATIONS non-atopic adult asthmatics", Intern Med. 2012;51(7):717-22, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM19—Haldar P. et al., "Cluster analysis and clinical asthma phenotypes", Am J Respir Crit Care Med. Aug. 1, 2008;178(3):218-224, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM20—Miskoff J.A. et al., "Fractional Exhaled Nitric Oxide Testing: Diagnostic Utility in Asthma, Chronic Obstructive Pulmonary Disease, or Asthma-chronic Obstructive Pulmonary Disease Overlap Syndrome", Cureus. Jun. 1, 20190;11(6):e4864, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM21—Dweik Read A. et al., Official clinical practice guideline of the American Thoracic Society; May 2011, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM22—Wenzel S. et al., The New England Journal of Medicine, 368(26): 2455-66, published online on May 21, 2013, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM22a—Supplementary Appendix of D2, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM23—Corren J, et al. Am J Respir Crit Care Med. Apr. 15, 2010;181(8):788- 96. 2010, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM24—WO 2010/053751 A1, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

TM25—Study record for NCT01312961 accessed from ClinicalTrials.gov, Version 31 dated Aug. 20, 2012, cited in Letter from the Opponent dated Jul. 14, 2025, regarding the Notice of Opposition against European Patent No. 4011915 (Application No. 21199451.2) filed Oct. 16, 2023, on behalf of Dr. Luigi Rumi.

Notice of Opposition against European Patent No. 4011915 (Application No. 21199451.2) dated Jul. 8, 2024, filed on behalf of Dr. Hans Ulrich Dorries.

WO—WO 2014/031610, grandparent application as filed, cited in Notice of Opposition against European Patent No. 4011915 (Application No. 21199451.2) filed on Jul. 8, 2024, on behalf of Dr. Hans Ulrich Dorries.

D1—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108), cited in Notice of Opposition against European Patent No. 4011915 (Application No. 21199451.2) filed on Jul. 8, 2024, on behalf of Dr. Hans Ulrich Dorries.

D2—Wenzel S. et al., The New England Journal of Medicine, 368(26): 2455-66, published online on May 21, 2013, cited in Notice of Opposition against European Patent No. 4011915 (Application No. 21199451.2) filed on Jul. 8, 2024, on behalf of Dr. Hans Ulrich Dorries.

D3—WO 2010/053751 A1, cited in Notice of Opposition against European Patent No. 4011915 (Application No. 21199451.2) filed on Jul. 8, 2024, on behalf of Dr. Hans Ulrich Dorries.

D4—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 8, 2024, on behalf of Dr. Hans Ulrich Dorries.

D5—Wenzel S.E., Nature Medicine, 18(5): 716-25, May 4, 2012, cited in Notice of Opposition against European Patent No. 4011915 (Application No. 21199451.2) filed on Jul. 8, 2024, on behalf of Dr. Hans Ulrich Dorries.

D6—Global Initiative for Asthma (GINA) Guidelines 2012; updated until Jun. 30, 2012, cited in Notice of Opposition against European Patent No. 4011915 (Application No. 21199451.2) filed on Jul. 8, 2024, on behalf of Dr. Hans Ulrich Dorries.

D7—WO 2011/156000 A2, cited in Notice of Opposition against European Patent No. 4011915 (Application No. 21199451.2) filed on Jul. 8, 2024, on behalf of Dr. Hans Ulrich Dorries.

D8—News provided by Aerovance Inc., "Phase 2b Clinical Trial Results Show Aerovance's AerovantTM is Effective in Patients with Eosinophilic Asthma", Jun. 8, 2010, cited in Notice of Opposition against European Patent No. 4011915 (Application No. 21199451.2) filed on Jul. 8, 2024, on behalf of Dr. Hans Ulrich Dorries.

D9—Wenzel S.E. et al., Late Breaking Abstract: Inhaled pitrakinra, an IL-antagonist, reduced exacerbations in patients with eosinophilic asthma; European Respiratory Journal 2010; 36: Suppl. 54, P3980, Sep. 21, 2010, cited in Notice of Opposition against European Patent No. 4011915 (Application No. 21199451.2) filed on Jul. 8, 2024, on behalf of Dr. Hans Ulrich Dorries.

D10—Wenzel S., Clinical and Experimental Allergy, 42(5): 650-8, published on Jan. 18, 2012 (as evidenced by the Annex appended to the document), cited in Notice of Opposition against European Patent No. 4011915 (Application No. 21199451.2) filed on Jul. 8, 2024, on behalf of Dr. Hans Ulrich Dorries.

D11—Dweik Read A et al., Official clinical practice guideline of the American Thoracic Society; May 2011, cited in Notice of Opposition against European Patent No. 4011915 (Application No. 21199451.2) filed on Jul. 8, 2024, on behalf of Dr. Hans Ulrich Dorries.

D12—Stewart L., Katial R.K., Immunology and allergy clinics of North America, 32(3): 347-62, available online on Jul. 5, 2012 (as evidenced by the Annex appended to the document), cited in Notice of Opposition against European Patent No. 4011915 (Application No. 21199451.2) filed on Jul. 8, 2024, on behalf of Dr. Hans Ulrich Dorries.

D13—Press release from Regeneron, "Regeneron Reports Fourth Quarter and Full Year 2011 Financial and Operating Results", Feb. 13, 2012, cited in Notice of Opposition against European Patent No. 4011915 (Application No. 21199451.2) filed on Jul. 8, 2024, on behalf of Dr. Hans Ulrich Dorries.

Notice of Opposition against European Patent No. 4011915 (Application No. 21199451.2) dated Jul. 12, 2024, filed on behalf of Michalski Hüttermann & Partner.

D1—Wenzel S.E., Nature Medicine, 18(5): 716-725, May 4, 2012, cited in Notice of Opposition against European Patent No. 4011915 (Application No. 21199451.2) filed on Jul. 12, 2024, on behalf of Michalski Huttermann & Partner.

D2—Bumbacea D et al. Eur Respir J. Jul. 2004;24(1):122-128, cited in Notice of Opposition against European Patent No. 4011915 (Application No. 21199451.2) filed on Jul. 12, 2024, on behalf of Michalski Hüttermann & Partner.

D3—Jenkins HA, et al. Chest. Oct. 2003; 124(4):1318-1324, cited in Notice of Opposition against European Patent No. 4011915 (Application No. 21199451.2) filed on Jul. 12, 2024, on behalf of Michalski Hüttermann & Partner.

D4—ten Brinke A, et al. Am J Respir Crit Care Med. Sep. 1, 2001;164(5):744-748, cited in Notice of Opposition against European Patent No. 4011915 (Application No. 21199451.2) filed on Jul. 12, 2024, on behalf of Michalski Hüttermann & Partner.

D5—Steinke JW, Borish L.. Respir Res. 2001;2(2):66-70, cited in Notice of Opposition against European Patent No. 4011915 (Application No. 21199451.2) filed on Jul. 12, 2024, on behalf of Michalski Hüttermann & Partner.

(56) References Cited

OTHER PUBLICATIONS

D6—WO 2010/053751 A1, cited in Notice of Opposition against European Patent No. 4011915 (Application No. 21199451.2) filed on Jul. 12, 2024, on behalf of Michalski Hüttermann & Partner.
D7—T. Greulich, et al Eur Respir J 2010; 36: Suppl. 54, 5492, cited in Notice of Opposition against European Patent No. 4011915 (Application No. 21199451.2) filed on Jul. 12, 2024, on behalf of Michalski Hüttermann & Partner.
D8—Bartoli ML et al Respir Med. Feb. 2004;98(2):184-93, cited in Notice of Opposition against European Patent No. 4011915 (Application No. 21199451.2) filed on Jul. 12, 2024, on behalf of Michalski Hüttermann & Partner.
D9—Fleming L, et al. Thorax. Mar. 2012;67(3): 193-8, cited in Notice of Opposition against European Patent No. 4011915 (Application No. 21199451.2) filed on Jul. 12, 2024, on behalf of Michalski Hüttermann & Partner.
D10—Bousquet J, et al. N Engl J Med. Oct. 1, 19901;323(15):1033-1039, cited in Notice of Opposition against European Patent No. 4011915 (Application No. 21199451.2) filed on Jul. 12, 2024, on behalf of Michalski Hüttermann & Partner.
D11—Wardlaw AJ, et al. Br Med Bull. 2000;56(4):985-1003, cited in Notice of Opposition against European Patent No. 4011915 (Application No. 21199451.2) filed on Jul. 12, 2024, on behalf of Michalski Huttermann & Partner.
D12—Haldar P, et al. N Engl J Med. Mar. 5, 2009;360(10):973-84, cited in Notice of Opposition against European Patent No. 4011915 (Application No. 21199451.2) filed on Jul. 12, 2024, on behalf of Michalski Hüttermann & Partner.
D13—Pavord ID, et al., Lancet. Aug. 1, 20128;380(9842):651-659, cited in Notice of Opposition against European Patent No. 4011915 (Application No. 21199451.2) filed on Jul. 12, 2024, on behalf of Michalski Hüttermann & Partner.
D14—excerpt from clinicaltrials.gov NCT01312961, cited in Notice of Opposition against European Patent No. 4011915 (Application No. 21199451.2) filed on Jul. 12, 2024, on behalf of Michalski Hüttermann & Partner.
D15—Wenzel S. et al., The New England Journal of Medicine, 368(26): 2455-66, published online on May 21, 2013, cited in Notice of Opposition against European Patent No. 4011915 (Application No. 21199451.2) filed on Jul. 12, 2024, on behalf of Michalski Hüttermann & Partner.
D16—Sandeep T et al., Lung India. Jul. 2010;27(3):138-40, cited in Notice of Opposition against European Patent No. 4011915 (Application No. 21199451.2) filed on Jul. 12, 2024, on behalf of Michalski Hüttermann & Partner.
D17—European Search Opinion in parent case EP3470432, cited in Notice of Opposition against European Patent No. 4011915 (Application No. 21199451.2) filed on Jul. 12, 2024, on behalf of Michalski Hüttermann & Partner.
D18—European Search Opinion of the present case, cited in Notice of Opposition against European Patent No. 4011915 (Application No. 21199451.2) filed on Jul. 12, 2024, on behalf of Michalski Hüttermann & Partner.
D19—Kharitonov S, et al., The European Respiratory Society Task Force. Eur Respir J. Jul. 1997;10(7):1683-1693, cited in Notice of Opposition against European Patent No. 4011915 (Application No. 21199451.2) filed on Jul. 12, 2024, on behalf of Michalski Hüttermann & Partner.
D20—Wenzel S, et al.. Lancet. Oct. 2, 20070;370(9596):1422-1431, cited in Notice of Opposition against European Patent No. 4011915 (Application No. 21199451.2) filed on Jul. 12, 2024, on behalf of Michalski Hüttermann & Partner.
D21—Corren J, et al. Am J Respir Crit Care Med. Apr. 15, 2010;181(8):788-796, cited in Notice of Opposition against European Patent No. 4011915 (Application No. 21199451.2) filed on Jul. 12, 2024, on behalf of Michalski Hüttermann & Partner.
D22—US 2003/0185821 A1, cited in Notice of Opposition against European Patent No. 4011915 (Application No. 21199451.2) filed on Jul. 12, 2024, on behalf of Michalski Hüttermann & Partner.
D23—Annex 1: Sequence alignments, cited in Notice of Opposition against European Patent No. 4011915 (Application No. 21199451.2) filed on Jul. 12, 2024, on behalf of Michalski Hüttermann & Partner.
D24—Annex 2: excerpts from the patent with all passages mentioning the term “FEV1”, cited in Notice of Opposition against European Patent No. 4011915 (Application No. 21199451.2) filed on Jul. 12, 2024, on behalf of Michalski Hüttermann & Partner.
D25—GINA Report 2009, cited in Notice of Opposition against European Patent No. 4011915 (Application No. 21199451.2) filed on Jul. 12, 2024, on behalf of Michalski Hüttermann & Partner.
D26—Pollart SM, et al. Am Fam Physician. May 1, 2009;79(9):761-767, cited in Notice of Opposition against European Patent No. 4011915 (Application No. 21199451.2) filed on Jul. 12, 2024, on behalf of Michalski Hüttermann & Partner.
D27—Wenzel S. Am J Respir Crit Care Med. Jul. 1, 20055;172(2):149-160, cited in Notice of Opposition against European Patent No. 4011915 (Application No. 21199451.2) filed on Jul. 12, 2024, on behalf of Michalski Hüttermann & Partner.
D28—Al-Ramli W et al.J Asthma. 2008;45 Suppl 1:41-44, cited in Notice of Opposition against European Patent No. 4011915 (Application No. 21199451.2) filed on Jul. 12, 2024, on behalf of Michalski Hüttermann & Partner.
D29—Annex 3: Disclosure of the string “severe asthma” in the application as filed on Aug. 20, 2013, and P1-P6, cited in Notice of Opposition against European Patent No. 4011915 (Application No. 21199451.2) filed on Jul. 12, 2024, on behalf of Michalski Hüttermann & Partner.
Notice of Opposition against European Patent No. 4011915 (Application No. 21199451.2) dated Jul. 16, 2024, filed on behalf of Boult Wade Tennant LLP.
D1—Text of EP21199451.2—divisional application as originally filed on Aug. 20, 2013, cited in Notice of Opposition against European Patent No. 4011915 (Application No. 21199451.2) filed on Jul. 16, 2024, on behalf of Boult Wade Tennant LLP.
D2—WO 2014/031610, grandparent application as filed on Aug. 20, 2013, cited in Notice of Opposition against European Patent No. 4011915 (Application No. 21199451.2) filed on Jul. 16, 2024, on behalf of Boult Wade Tennant LLP.
D3—U.S. Pat. No. 8,075,887 B2, cited in Notice of Opposition against European Patent No. 4011915 (Application No. 21199451.2) filed on Jul. 16, 2024, on behalf of Boult Wade Tennant LLP.
D4—Munakata, Exhaled Nitric Oxide (FeNO) as a Non-invasive Marker of Airway Inflammation, Allergology International, vol. 61: 365-372, 2012, cited in Notice of Opposition against European Patent No. 4011915 (Application No. 21199451.2) filed on Jul. 16, 2024, on behalf of Boult Wade Tennant LLP.
D5—GINA Report 2009, cited in Notice of Opposition against European Patent No. 4011915 (Application No. 21199451.2) filed on Jul. 16, 2024, on behalf of Boult Wade Tennant LLP.
D6—Pavord ID, et al., Lancet. Aug. 1, 20128;380(9842):651-9, cited in Notice of Opposition against European Patent No. 4011915 (Application No. 21199451.2) filed on Jul. 16, 2024, on behalf of Boult Wade Tennant LLP.
D7—Study record for NCT01312961 accessed from ClinicalTrials.gov, Version 31 dated Aug. 20, 2012, cited in Notice of Opposition against European Patent No. 4011915 (Application No. 21199451.2) filed on Jul. 16, 2024, on behalf of Boult Wade Tennant LLP.
D8—Press release from Regeneron, “Regeneron Reports Fourth Quarter and Full Year 2011 Financial and Operating Results”, Feb. 13, 2012, cited in Notice of Opposition against European Patent No. 4011915 (Application No. 21199451.2) filed on Jul. 16, 2024, on behalf of Boult Wade Tennant LLP.
D9—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 16, 2024, on behalf of Boult Wade Tennant LLP.
D10—Hashimoto and Bel., Current treatment of severe asthma, Clin. Exp. Allergy., vol. 42(5): 693-705, May 2012, cited in Notice

(56) References Cited

OTHER PUBLICATIONS of Opposition against European Patent No. 4011915 (Application No. 21199451.2) filed on Jul. 16, 2024, on behalf of Boult Wade Tennant LLP.
D11—Alving et al., Increased amount of nitric oxide in exhaled air of asthmatics, Eur Respir J., vol. 6: 1366-1370, 1993, cited in Notice of Opposition against European Patent No. 4011915 (Application No. 21199451.2) filed on Jul. 16, 2024, on behalf of Boult Wade Tennant LLP.
D12—Wenzel S. et al., The New England Journal of Medicine, 368(26): 2455-66, published online on May 21, 2013, cited in Notice of Opposition against European Patent No. 4011915 (Application No. 21199451.2) filed on Jul. 16, 2024, on behalf of Boult Wade Tennant LLP.
D13—Supplementary Appendix of Wenzel, 2013, cited in Notice of Opposition against European Patent No. 4011915 (Application No. 21199451.2) filed on Jul. 16, 2024, on behalf of Boult Wade Tennant LLP.
D14—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108), cited in Notice of Opposition against European Patent No. 4011915 (Application No. 21199451.2) filed on Jul. 16, 2024, on behalf of Boult Wade Tennant LLP.
D15—Proprietors letter of Oct. 17, 2019 on EP3470432, cited in Notice of Opposition against European Patent No. 4011915 (Application No. 21199451.2) filed on Jul. 16, 2024, on behalf of Boult Wade Tennant LLP.
D16—Brusselle and Bracke, Targeting Immune Pathways for Therapy in Asthma and Chronic Obstructive Pulmonary Disease, Ann Am Throrac Soc, vol. 11, Supplement 5, S322-S328, Dec. 2014, cited in Notice of Opposition against European Patent No. 4011915 (Application No. 21199451.2) filed on Jul. 16, 2024, on behalf of Boult Wade Tennant LLP.
D17—Wechsler, Inhibiting Interleukin-4 and Interleukin-13 in Difficult-to-Control Asthma, New England Journal of Medicine, vol. 368;26: 2511- 2513, Jun. 27, 2013, cited in Notice of Opposition against European Patent No. 4011915 (Application No. 21199451.2) filed on Jul. 16, 2024, on behalf of Boult Wade Tennant LLP.
Notice of Opposition against European Patent No. 4011915 (Application No. 21199451.2) dated Jul. 17, 2024, filed on behalf of Secerna LLP.
D1—Wenzel S., Clinical and Experimental Allergy, 42(5): 650-8, published on Jan. 18, 2012 (as evidenced by the Annex appended to the document), cited in Notice of Opposition against European Patent No. 4011915 (Application No. 21199451.2) filed on Jul. 17, 2024, on behalf of Secerna LLP.
D2—Firszt & Kraft, Pharmacotherapy of Severe Asthma. Curr Opin Pharmacol. (2010); 10(3): 266-271, cited in Notice of Opposition against European Patent No. 4011915 (Application No. 21199451.2) filed on Jul. 17, 2024, on behalf of Secerna LLP.
D3—Pollart SM, et al. Am Fam Physician. May 1, 2009;79(9):761-7, cited in Notice of Opposition against European Patent No. 4011915 (Application No. 21199451.2) filed on Jul. 17, 2024, on behalf of Secerna LLP.
D4—Wenzel S. et al., The New England Journal of Medicine, 368(26): 2455-66, published online on May 21, 2013, cited in Notice of Opposition against European Patent No. 4011915 (Application No. 21199451.2) filed on Jul. 17, 2024, on behalf of Secerna LLP.
D5—Protocol for: Wenzel et al. Dupilumab in persistent asthma with elevated eosinophil levels. N Engl J Med 2013; 368:2455-66, cited in Notice of Opposition against European Patent No. 4011915 (Application No. 21199451.2) filed on Jul. 17, 2024, on behalf of Secerna LLP.
D6—Wechsler, Inhibiting Interleukin-4 and Interleukin-13 in Difficult-to-Control Asthma, New England Journal of Medicine, vol. 368;26: 2511- 2513, Jun. 27, 2013, cited in Notice of Opposition against European Patent No. 4011915 (Application No. 21199451.2) filed on Jul. 17, 2024, on behalf of Secerna LLP.
D7—U.S. Pat. No. 8,075,887 B2, cited in Notice of Opposition against European Patent No. 4011915 (Application No. 21199451.2) filed on Jul. 17, 2024, on behalf of Secerna LLP.
D8—WO 2010/053751 A1, cited in Notice of Opposition against European Patent No. 4011915 (Application No. 21199451.2) filed on Jul. 17, 2024, on behalf of Secerna LLP.
D9—Study record for NCT01312961 accessed from ClinicalTrials.gov, Version 31 dated Aug. 20, 2012, cited in Notice of Opposition against European Patent No. 4011915 (Application No. 21199451.2) filed on Jul. 17, 2024, on behalf of Secerna LLP.
D10—Regeneron Science to Medicine, J.P. Morgan Healthcare Conference, Jan. 2013, cited in Notice of Opposition against European Patent No. 4011915 (Application No. 21199451.2) filed on Jul. 17, 2024, on behalf of Secerna LLP.
D11—Press release from Regeneron, "Regeneron Reports Fourth Quarter and Full Year 2011 Financial and Operating Results", Feb. 13, 2012, cited in Notice of Opposition against European Patent No. 4011915 (Application No. 21199451.2) filed on Jul. 17, 2024, on behalf of Secerna LLP.
D12—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 17, 2024, on behalf of Secerna LLP.
D13—Wenzel S.E. et al., Late Breaking Abstract: Inhaled pitrakinra, an IL-antagonist, reduced exacerbations in patients with eosinophilic asthma; European Respiratory Journal 2010; 36: Suppl. 54, P3980, Sep. 21, 2010, cited in Notice of Opposition against European Patent No. 4011915 (Application No. 21199451.2) filed on Jul. 17, 2024, on behalf of Secerna LLP.
D14—Corren J, et al. Am J Respir Crit Care Med. Apr. 15, 2010;181(8):788-96, cited in Notice of Opposition against European Patent No. 4011915 (Application No. 21199451.2) filed on Jul. 17, 2024, on behalf of Secerna LLP.
D15—Editorial commentary on Corren et al. Borish—Am J Respir Crit Care Med; 181(8):769-772. Jan. 7, 2010, cited in Notice of Opposition against European Patent No. 4011915 (Application No. 21199451.2) filed on Jul. 17, 2024, on behalf of Secerna LLP.
D16—Hashimoto and Bel., Current treatment of severe asthma, Clin. Exp. Allergy., vol. 42(5): 693-705, May 2012, cited in Notice of Opposition against European Patent No. 4011915 (Application No. 21199451.2) filed on Jul. 17, 2024, on behalf of Secerna LLP.
D17—Pavord ID, et al., Lancet. Aug. 18, 2012;380(9842):651-659, cited in Notice of Opposition against European Patent No. 4011915 (Application No. 21199451.2) filed on Jul. 17, 2024, on behalf of Secerna LLP.
D18—Nancy M. Abdelaty, Patient characteristics that can predict response to omalizumab an (Anti-IgE Antibody) for achieving better control of asthmatic patients, Egyptian Journal of Chest Diseases and Tuberculosis, vol. 61, Issue 3, pp. 15-22, Jul. 2012, cited in Notice of Opposition against European Patent No. 4011915 (Application No. 21199451.2) filed on Jul. 17, 2024, on behalf of Secerna LLP.
D19—Szefler et al. Asthma Outcomes: Biomarkers. J Allergy Clin Immunol. 2012 129: S9-23. Mar. 1, 2012, cited in Notice of Opposition against European Patent No. 4011915 (Application No. 21199451.2) filed on Jul. 17, 2024, on behalf of Secerna LLP.
D20—Spector & Tan. Is a single blood eosinophil count a reliable marker for "eosinophilic asthma?". Journal of Asthma 49.8 (2012): Early Online: 1-4. Aug. 20, 2012, cited in Notice of Opposition against European Patent No. 4011915 (Application No. 21199451.2) filed on Jul. 17, 2024, on behalf of Secerna LLP.
D21—WHO Drug Information, vol. 26, No. 4, pp. 401-471, "Proposed INN: List 108", published on Dec. 9, 2012 (as evidenced by the Annex appended to the document retrieved from https://www.who.int/publications/m/item/inn-pl-108) , cited in Notice of Opposition against European Patent No. 4011915 (Application No. 21199451.2) filed on Jul. 17, 2024, on behalf of Secerna LLP.
D22—Darveaux & Busse. Biologics in asthma—the next step to personalised treatment. J Allergy Clin Immunol Pract. Mar.-Apr. 2015; 3(2): 152-161. Mar. 2015, cited in Notice of Opposition

(56) References Cited

OTHER PUBLICATIONS against European Patent No. 4011915 (Application No. 21199451.2) filed on Jul. 17, 2024, on behalf of Secerna LLP.
D23—Eisenstein. Something new under the skin. Nature Biotechnology 29(2), 107-109 (2011). Feb. 7, 2011, cited in Notice of Opposition against European Patent No. 4011915 (Application No. 21199451.2) filed on Jul. 17, 2024, on behalf of Secerna LLP.
D24—Chapter 19, "Dosage regimens" of Aulton's Pharmaceutics: The Science of Dosage Form Design, 2nd Edition, 2001, cited in Notice of Opposition against European Patent No. 4011915 (Application No. 21199451.2) filed on Jul. 17, 2024, on behalf of Secerna LLP.
D25—Djukanovic et al.2002, Eur. Respire. J. 37: 1S-2S), cited in Notice of Opposition against European Patent No. 4011915 (Application No. 21199451.2) filed on Jul. 17, 2024, on behalf of Secerna LLP.
D26—Alving et al., Increased amount of nitric oxide in exhaled air of asthmatics, Eur Respir J., vol. 6: 1366-1370, 1993, cited in Notice of Opposition against European Patent No. 4011915 (Application No. 21199451.2) filed on Jul. 17, 2024, on behalf of Secerna LLP.
D27—Appeal Brief filed by Proprietor during prosecution of U.S. Pat. No. 13,971,334. Mar. 24, 2016, cited in Notice of Opposition against European Patent No. 4011915 (Application No. 21199451.2) filed on Jul. 17, 2024, on behalf of Secerna LLP.
D28—Handlogten et al "Prevention of Fab-arm exchange and antibody reduction via stabilization of the IgG4 hinge region" MAbs. 12(1): 1779974. 2020, cited in Notice of Opposition against European Patent No. 4011915 (Application No. 21199451.2) filed on Jul. 17, 2024, on behalf of Secerna LLP.
D29—Silva et al The S228P Mutation Prevents in Vivo and in Vitro IgG4 Fab-arm Exchange as demonstrated using a Combination of Novel Quantitative Immunoassays and Physiological Matrix Preparation, J Biol Chem. Jan. 8, 2015;290(9):5462-5469, cited in Notice of Opposition against European Patent No. 4011915 (Application No. 21199451.2) filed on Jul. 17, 2024, on behalf of Secerna LLP.
D30—Dumet et al "Insights into the IgG heavy chain engineering patent landscape as applied to IgG4 antibody development" MABS. 11(8) 1341-1350, 2019, cited in Notice of Opposition against European Patent No. 4011915 (Application No. 21199451.2) filed on Jul. 17, 2024, on behalf of Secerna LLP.
D31—Center for Drug Evaluation and Research "Clinical Review, Brenda Carr, MD, BLA 761055, Dupixent (dupilumab)" Application Number: 761055Orig1s000 Reference ID: 4075125, Apr. 9, 2015, cited in Notice of Opposition against European Patent No. 4011915 (Application No. 21199451.2) filed on Jul. 17, 2024, on behalf of Secerna LLP.
D32—Shannon et al."Differences in airway cytokine profile in severe asthma compared to moderate asthma" Chest. 133(2):420-6. Feb. 2008, cited in Notice of Opposition against European Patent No. 4011915 (Application No. 21199451.2) filed on Jul. 17, 2024, on behalf of Secerna LLP.
D33—Bossley et al."Pediatric severe asthma is characterized by eosinophilia and remodeling without TH2 cytokines" J Allergy Clin Immunol. 129(4): 974-82.e13. Apr. 2012, cited in Notice of Opposition against European Patent No. 4011915 (Application No. 21199451.2) filed on Jul. 17, 2024, on behalf of Secerna LLP.
D34—Wenzel "Severe Asthma in Adults" Am J Respir Crit Care Med. 172(2) 149-160, 2005, cited in Notice of Opposition against European Patent No. 4011915 (Application No. 21199451.2) filed on Jul. 17, 2024, on behalf of Secerna LLP.
D35—Al-Ramli W et al.J Asthma. 2008;45 Suppl 1:41-4, cited in Notice of Opposition against European Patent No. 4011915 (Application No. 21199451.2) filed on Jul. 17, 2024, on behalf of Secerna LLP.
D36—Lommatzsch et al."Severe Asthma: Definition, Diagnosis and Treatment", Dtsch Arztebl Int., 111(50): 847-855. Dec. 2014, cited in Notice of Opposition against European Patent No. 4011915 (Application No. 21199451.2) filed on Jul. 17, 2024, on behalf of Secerna LLP.
D37—Costantino et al."Intranasal delivery: Physicochemical and therapeutic aspects" International Journal of Pharmaceutics. 337(1-2), 1-24, 2007, cited in Notice of Opposition against European Patent No. 4011915 (Application No. 21199451.2) filed on Jul. 17, 2024, on behalf of Secerna LLP.
D38—Thomson et al "Omalizumab: Clinical Use for the Management of Asthma" Clin Med Insights Circ Respir Pulm Med. 6: 27-40, 2012, cited in Notice of Opposition against European Patent No. 4011915 (Application No. 21199451.2) filed on Jul. 17, 2024, on behalf of Secerna LLP.
D39—Kelly et al."Nedocromil sodium versus sodium cromoglycate for preventing exercise-induced bronchoconstriction" Cochrane Database Syst Rev. 2000(3): CD002731. Jul. 24, 2000, cited in Notice of Opposition against European Patent No. 4011915 (Application No. 21199451.2) filed on Jul. 17, 2024, on behalf of Secerna LLP.
D40—Gore "The utility of antifungal agents for asthma" Curr Opin Pulm Med. 16(1):36-41. Jan. 2010, cited in Notice of Opposition against European Patent No. 4011915 (Application No. 21199451.2) filed on Jul. 17, 2024, on behalf of Secerna LLP.
Notice of Opposition against European Patent No. 4011915 (Application No. 21199451.2) dated Jul. 17, 2024, filed on behalf of Hampton Knowles Limited.
D2—Wenzel S. et al., The New England Journal of Medicine, 368(26): 2455-66, published online on May 21, 2013, cited in Notice of Opposition against European Patent No. 4011915 (Application No. 21199451.2) filed on Jul. 17, 2024, on behalf of Hampton Knowles Limited.
D4—Otulana et al., American Journal of Respiratory and Critical Care Medicine, 183: A6179, American Thoracic Society 2011 International Conference Abstract, May 18, 2011, cited in Notice of Opposition against European Patent No. 4011915 (Application No. 21199451.2) filed on Jul. 17, 2024, on behalf of Hampton Knowles Limited.
D7—WO 2011/156000 A2, cited in Notice of Opposition against European Patent No. 4011915 (Application No. 21199451.2) filed on Jul. 17, 2024, on behalf of Hampton Knowles Limited.
D9—Wenzel S.E. et al., Late Breaking Abstract: Inhaled pitrakinra, an IL-antagonist, reduced exacerbations in patients with eosinophilic asthma; European Respiratory Journal 2010; 36: Suppl. 54, P3980, Sep. 21, 2010, cited in Notice of Opposition against European Patent No. 4011915 (Application No. 21199451.2) filed on Jul. 17, 2024, on behalf of Hampton Knowles Limited.
D10—Wenzel S., Clinical and Experimental Allergy, 42(5): 650-8, published on Jan. 18, 2012 (as evidenced by the Annex appended to the document), cited in Notice of Opposition against European Patent No. 4011915 (Application No. 21199451.2) filed on Jul. 17, 2024, on behalf of Hampton Knowles Limited.
D31—Corren J, et al. Am J Respir Crit Care Med. Apr. 1, 20105;181(8):788- 96, cited in Notice of Opposition against European Patent No. 4011915 (Application No. 21199451.2) filed on Jul. 17, 2024, on behalf of Hampton Knowles Limited.
DYC01—Woodruff P.G. et al., "T-helper type 2-driven inflammation defines major subphenotypes of asthma", Am J Respir Crit Care Med. Sep. 1, 2009;180(5):388-95, cited in Notice of Opposition against European Patent No. 4011915 (Application No. 21199451.2) filed on Jul. 17, 2024, on behalf of Hampton Knowles Limited.
DYC02—Szefler et al. Asthma Outcomes: Biomarkers. J Allergy Clin Immunol., 129: S9-23. Mar. 1, 2012, cited in Notice of Opposition against European Patent No. 4011915 (Application No. 21199451.2) filed on Jul. 17, 2024, on behalf of Hampton Knowles Limited.
DYC03—Shannon et al."Differences in airway cytokine profile in severe asthma compared to moderate asthma" Chest. 133(2):420-6. Feb. 2008, cited in Notice of Opposition against European Patent No. 4011915 (Application No. 21199451.2) filed on Jul. 17, 2024, on behalf of Hampton Knowles Limited.
DYC04—Editorial commentary on Corren et al. Borish—Am J Respir Crit Care Med; 181(8):769-772; Jul. 1, 2010, cited in Notice of Opposition against European Patent No. 4011915 (Application No. 21199451.2) filed on Jul. 17, 2024, on behalf of Hampton Knowles Limited.
DYC05—Hashimoto and Bel., Current treatment of severe asthma, Clin. Exp. Allergy., vol. 42(5): 693-705, May 2012, cited in Notice

(56) References Cited

OTHER PUBLICATIONS of Opposition against European Patent No. 4011915 (Application No. 21199451.2) filed on Jul. 17, 2024, on behalf of Hampton Knowles Limited.
DYC06—U.S. Pat. No. 8,075,887 B2, cited in Notice of Opposition against European Patent No. 4011915 (Application No. 21199451.2) filed on Jul. 17, 2024, on behalf of Hampton Knowles Limited.
DYC07—Kostic et al., Clinical Immunology, 2010, 135:S105-S106, cited in Notice of Opposition against European Patent No. 4011915 (Application No. 21199451.2) filed on Jul. 17, 2024, on behalf of Hampton Knowles Limited.
DYC08—excerpt from clinicaltrials.gov NCT01312961, cited in Notice of Opposition against European Patent No. 4011915 (Application No. 21199451.2) filed on Jul. 17, 2024, on behalf of Hampton Knowles Limited.
DYC09—Global Initiative for Asthma, "Global Strategy for Asthma Management and Prevention", 2011, chapters 2 and 3, cited in Notice of Opposition against European Patent No. 4011915 (Application No. 21199451.2) filed on Jul. 17, 2024, on behalf of Hampton Knowles Limited.
Reply of the Patent Proprietor to the Notice of Opposition against European Patent No. 4011915 (Application No. 21199451.2) dated Jan. 27, 2025, filed on behalf of Sanofi Biotechnology.
D80—Wenzel et al. (2016), Lancet, 388: 31-14, cited in Reply of the Patent Proprietor dated Jan. 27, 2005, filed on behalf of Sanofi Biotechnology, in response to the Notices of Opposition against European Patent No. 4011915 (Application No. 21199451.2).
D81—Wang et al. (2007), N Engl J Med, 357; 21:2189-2194, cited in Reply of the Patent Proprietor dated Jan. 27, 2005, filed on behalf of Sanofi Biotechnology, in response to the Notices of Opposition against European Patent No. 4011915 (Application No. 21199451.2).
D82—Lagakos et al. (2006), N Engl J Med 354; 16:1667-1669, cited in Reply of the Patent Proprietor dated Jan. 27, 2005, filed on behalf of Sanofi Biotechnology, in response to the Notices of Opposition against European Patent No. 4011915 (Application No. 21199451.2).
Reply of the Patent Proprietor to the Communication of Notices of Opposition against European Patent No. 3470432 (Application No. 18194745.8), dated Jul. 20, 2022, on behalf of Sanofi Biotechnology.
European Patent Office Decision Revoking European Patent No. 3470432 (Application No. 18194745.8), dated Feb. 2, 2023.
Reply of the Patent Proprietor to the Notice of Opposition against European Patent No. 3973987 (Application No. 21191120.1), filed Apr. 24, 2025, on behalf of Sanofi Biotechnology.
D87—Wenzel et al., Dupilumab efficacy and safety in adults with uncontrolled persistent asthma despite use of medium-to-high-dose inhaled corticosteroids plus a long-acting β2 agonist: a randomised double-blind placebo-controlled pivotal phase 2b dose-ranging trial, Lancet, Apr. 27, 2016, 388:31-44, cited in Reply of the Patent Proprietor to the Notice of Opposition against European Patent No. 3973987 (Application No. 21191120.1), filed Apr. 24, 2025, on behalf of Sanofi Biotechnology.
D88—Castro et al., "Dupilumab Efficacy and Safety in Moderate-to-Severe Uncontrolled Asthma", NEJM, Jun. 28, 2018, vol. 378, No. 26, pp. 2486-2496, cited in Reply of the Patent Proprietor to the Notice of Opposition against European Patent No. 3973987 (Application No. 21191120.1), filed Apr. 24, 2025, on behalf of Sanofi Biotechnology.
D89—EMA Guidance on FIH Trials, Committee for Medicinal Products for Human Use (CHMP), Jul. 19, 2007, cited in Reply of the Patent Proprietor to the Notice of Opposition against European Patent No. 3973987 (Application No. 21191120.1), filed Apr. 24, 2025, on behalf of Sanofi Biotechnology.
D90—Kips et al., New anti-asthma therapies: suppression of the effect of interleukin (IL)-4 and IL-5, European Respiratory Journal, 2001, 17(3): 499-506, cited in Reply of the Patent Proprietor to the Notice of Opposition against European Patent No. 3973987 (Application No. 21191120.1), filed Apr. 24, 2025, on behalf of Sanofi Biotechnology.
D91—Oldhoff et al., Anti-IL-5 recombinant humanized monoclonal antibody (mepolizumab) for the treatment of atopic dermatitis, Allergy, May 2005, 60(5): 693-696, cited in Reply of the Patent Proprietor to the Notice of Opposition against European Patent No. 3973987 (Application No. 21191120.1), filed Apr. 24, 2025, on behalf of Sanofi Biotechnology.
D92—Schujis et al., Cytokine targets in airway inflammation, Curr Opin Pharmacol, Jun. 2013, 13(3): 351-361, cited in Reply of the Patent Proprietor to the Notice of Opposition against European Patent No. 3973987 (Application No. 21191120.1), filed Apr. 24, 2025, on behalf of Sanofi Biotechnology.
D93—Bice et al., "Biologic targeted therapy in allergic asthma", Annals of Allergy, Asthma & Immunology, 2014, 112(2): 108-115, cited in Reply of the Patent Proprietor to the Notice of Opposition against European Patent No. 3973987 (Application No. 21191120.1), filed Apr. 24, 2025, on behalf of Sanofi Biotechnology.
D94—Hay et al., Clinical development success rates for investigational drugs, Nature Biotechnology, Jan. 9, 2014, 32: 40-51, cited in Reply of the Patent Proprietor to the Notice of Opposition against European Patent No. 3973987 (Application No. 21191120.1), filed Apr. 24, 2025, on behalf of Sanofi Biotechnology.
D95—Rabe et al., Efficacy and Safety of Dupilumab in Glucocorticoid-Dependent Severe Asthma, NEJM, May 21, 2018, 378: 2475-2485, cited in Reply of the Patent Proprietor to the Notice of Opposition against European Patent No. 3973987 (Application No. 21191120.1), filed Apr. 24, 2025, on behalf of Sanofi Biotechnology.
D96—Declaration of Prof. lan Pavord dated Apr. 24, 2025, cited in Reply of the Patent Proprietor to the Notice of Opposition against European Patent No. 3973987 (Application No. 21191120.1), filed Apr. 24, 2025, on behalf of Sanofi Biotechnology.
D96a—List of Publications by Prof. Ian Pavord, cited in Reply of the Patent Proprietor to the Notice of Opposition against European Patent No. 3973987 (Application No. 21191120.1), filed Apr. 24, 2025, on behalf of Sanofi Biotechnology.
Reply of the Patent Proprietor to the Communication of Notices of Opposition against European Patent No. 3107575 (Application No. 15708991.3), dated Jan. 2, 2023, on behalf of Sanofi Biotechnology.
D41—Gina Report Dec. 2012, Global Strategy for Asthma Management and Prevention, GINA ©2012 & Global Initiative for Asthma, reprinted with permission, Available from www.ginasthma.org, cited in Reply of the Patent Proprietor to the Communication of Notices of Opposition against European Patent No. 3107575 (Application No. 15708991.3), dated Jan. 2, 2023, on behalf of Sanofi Biotechnology.
D42—Rabe et al., Efficacy and Safety of Dupilumab in Glucocorticoid-Dependent Severe Asthma, NEJM, May 21, 2018, 378: 2475-2485, cited in Reply of the Patent Proprietor to the Communication of Notices of Opposition against European Patent No. 3107575 (Application No. 15708991.3), dated Jan. 2, 2023, on behalf of Sanofi Biotechnology.
D43—EMA Guidance, Committee for Medicinal Products for HUman Use (CHMP), Jul. 19, 2007, cited in Reply of the Patent Proprietor to the Communication of Notices of Opposition against European Patent No. 3107575 (Application No. 15708991.3), dated Jan. 2, 2023, on behalf of Sanofi Biotechnology.
D44—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Reply of the Patent Proprietor to the Communication of Notices of Opposition against European Patent No. 3107575 (Application No. 15708991.3), dated Jan. 2, 2023, on behalf of Sanofi Biotechnology.
D45—Schujis et al., Cytokine targets in airway inflammation, Curr Opin Pharmacol, Jun. 2013, 13(3): 351-361, Epulished May 2, 2013, cited in Reply of the Patent Proprietor to the Communication of Notices of Opposition against European Patent No. 3107575 (Application No. 15708991.3), dated Jan. 2, 2023, on behalf of Sanofi Biotechnology.
D46—Hay et al., Clinical development success rates for investigational drugs, Nature Biotechnology, Jan. 9, 2014, 32: 40-51, cited in Reply of the Patent Proprietor to the Communication of Notices of

(56) References Cited

OTHER PUBLICATIONS

Opposition against European Patent No. 3107575 (Application No. 15708991.3), dated Jan. 2, 2023, on behalf of Sanofi Biotechnology.
D47—Wang et al., Monoclonal antibody pharmacokinetics and pharmacodynamics, Clinical Pharmacology & Therapeutics, 2008, 84(5):548- 558, cited in Reply of the Patent Proprietor to the Communication of Notices of Opposition against European Patent No. 3107575 (Application No. 15708991.3), dated Jan. 2, 2023, on behalf of Sanofi Biotechnology.
D48—Mould et al., Current Opinion in Drug Discovery & Development, 2007, 10(1): 84-96, cited in Reply of the Patent Proprietor to the Communication of Notices of Opposition against European Patent No. 3107575 (Application No. 15708991.3), dated Jan. 2, 2023, on behalf of Sanofi Biotechnology.
D49—Kips et al., New anti-asthma therapies: suppression of the effect of interleukin (IL)-4 and IL-5, European Respiratory Journal, 2001, 17(3): 499-506, cited in Reply of the Patent Proprietor to the Communication of Notices of Opposition against European Patent No. 3107575 (Application No. 15708991.3), dated Jan. 2, 2023, on behalf of Sanofi Biotechnology.
D50—Pavord et al., Mepolizumab for severe eosinophilic asthma (DREAM): a multicentre, double-blind, placebo-controlled trial, Lancet, Aug. 18, 2012; 380: 651- 659, cited in Reply of the Patent Proprietor to the Communication of Notices of Opposition against European Patent No. 3107575 (Application No. 15708991.3), dated Jan. 2, 2023, on behalf of Sanofi Biotechnology.
D51—Oldhoff et al., Anti-IL-5 recombinant humanized monoclonal antibody (mepolizumab) for the treatment of atopic dermatitis, Allergy, May 2005, 60(5): 693-696, cited in Reply of the Patent Proprietor to the Communication of Notices of Opposition against European Patent No. 3107575 (Application No. 15708991.3), dated Jan. 2, 2023, on behalf of Sanofi Biotechnology.
D52—REC Standard Operating Procedures, cited in Reply of the Patent Proprietor to the Communication of Notices of Opposition against European Patent No. 3107575 (Application No. 15708991.3), dated Jan. 2, 2023, on behalf of Sanofi Biotechnology.
D53—REC Annual Report, cited in Reply of the Patent Proprietor to the Communication of Notices of Opposition against European Patent No. 3107575 (Application No. 15708991.3), dated Jan. 2, 2023, on behalf of Sanofi Biotechnology.
D57—NHS Health Research Authority, "Dupilumab for adult patients with moderate to severe atopic dermatitis", REC Opinion, May 30, 2014, cited in Reply to Patent Proprietor's Response to Notices of Opposition against European Patent No. 3107575 (EP Application No. 15708991.3) filed on behalf of Regina Neuefeind, dated Apr. 20, 2023.
Reply to Patent Proprietor's Response to Notices of Opposition against European Patent No. 3107575 (EP Application No. 15708991.3) filed on behalf of Dr. Regina Neuefeind, dated Apr. 20, 2023.
D54—Chain A, Dupilumab Fab heavy chain, Accession No. 6WGB_A, Dec. 1, 2020, cited in Reply to Patent Proprietor's Response to Notices of Opposition against European Patent No. 3107575 (EP Application No. 15708991.3) filed on behalf of Regina Neuefeind, dated Apr. 20, 2023.
D55—Chain B, Dupilumab Fab light chain, Accession No. 6WGB_B, Dec. 1, 2020, cited in Reply to Patent Proprietor's Response to Notices of Opposition against European Patent No. 3107575 (EP Application No. 15708991.3) filed on behalf of Regina Neuefeind, dated Apr. 20, 2023.
D56—Preliminary Opinion T0829/19, cited in Reply to Patent Proprietor's Response to Notices of Opposition against European Patent No. 3107575 (EP Application No. 15708991.3) filed on behalf of Regina Neuefeind, dated Apr. 20, 2023.
Response to Summons to Attend Oral Proceedings regarding Opposition against European Patent No. 3107575 (EP Application No. 15708991.3), filed on behalf of Dr. Regina Neuefeind, dated Nov. 15, 2023.
Response to Summons to Attend Oral Proceedings regarding Opposition against European Patent No. 3107575 (EP Application No. 15708991.3), filed on behalf of Dr. Hans Ulrich Dorries, dated Nov. 15, 2023.
Response to Summons to Attend Oral Proceedings regarding Opposition against European Patent No. 3107575 (EP Application No. 15708991.3), filed on behalf of D. Young & Co., dated Nov. 15, 2023.
Submission Under Rule 116 EPC by Patent Proprietor regarding Opposition against European Patent No. 3107575 (EP Application No. 15708991.3), filed on behalf of Sanofi Biotechnology, dated Nov. 15, 2023.
Norwegian Publicaiton No. NO983141L dated Jan. 10, 2000, cited in Submission Under Rule 116 EPC by Patent Proprietor regarding Opposition against European Patent No. 3107575 (EP Application No. 15708991.3), filed on behalf of Sanofi Biotechnology, dated Nov. 15, 2023.
Appeal Number T0563/24-3.3.04 Following Opposition against European Patent No. 3107575 (EP Application No. 15708991.3) filed on behalf of D Young & Co. LLP, dated May 7, 2024.
Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Fracasso et al., A Phase 1 Escalating Single-Dose and Weekly Fixed-Dose Study of Cetuximab: Pharmacokinetic and Pharmacodynamic Rationale for Dosing, Clin Cancer Res, 2007, 13(3):986- 993, cited in Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Mould et al., Population pharmacokinetics—pharmacodynamics of alemtuzumab (Campath®) in patients with chronic lymphocytic leukaemia and its link to treatment response, Br J Clin Pharmacol, 2007, 64(3):278- 291, cited in Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Sohn et al., The pharmacokinetics and pharmacodynamics of denosumab in patients with advanced solid tumours and bone metastases: a systematic review, Br J Clin Pharmacol, 2014, 78(3):477- 487, cited in Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Dostalek et al., Pharmacokinetics, pharmacodynamics and physiologically-based pharmacokinetic modelling of monoclonal antibodies, Clin Pharmacokinet, 2013, 52: 83-124, cited in Grounds for Appeal regarding Appeal Number T0563/24-3.3.04 Following Opposition against European Patent No. 3107575 (EP Application No. 15708991.3) filed on behalf of D Young & Co. LLP, dated Jul. 8, 2024.
Patentee's Reply to Grounds for Appeal regarding Appeal Number T0563/24-3.3.04 Following Opposition against European Patent No. 3107575 (EP Application No. 15708991.3), filed on behalf of Sanofi Biotechnology, dated Nov. 11, 2024.
Comments in Preparation of the Oral Proceedings regarding Pantentee's Reply to Grounds for Appeal regarding Appeal Number T0563/24-3.3.04 Following Opposition against European Patent No. 3107575 (EP Application No. 15708991.3), filed on behalf of Sanofi Biotechnology, dated Jun. 12, 2025.
Letter of the Patent Proprietor regarding Appeal Number T0563/24-3.3.04 Following Opposition against European Patent No. 3107575 (EP Application No. 15708991.3), filed on behalf of Sanofi Biotechnology, dated Nov. 12, 2025.
Written Submission Under Rule 116EPC regarding European Patent No. 3703818 (EP Application No. 18799655.8), filed on behalf of Hampton Knowles Limited, dated Dec. 18, 2025.
Written Submission Under Rule 116EPC regarding European Patent No. 3703818 (EP Application No. 18799655.8), filed on behalf of Dr. Hans Ulrich Dorries, dated Dec. 19, 2025.

(56) References Cited

OTHER PUBLICATIONS

Written Submission Under Rule 116EPC regarding European Patent No. 3703818 (EP Application No. 18799655.8), filed by Boehmert & Boehmert, dated Dec. 22, 2025.
Written Submission Under Rule 116EPC regarding European Patent No. 3703818 (EP Application No. 18799655.8), filed on behalf of Lanyon Oppositions Limited (O2), dated Dec. 22, 2025.
Written Submission Under Rule 116EPC regarding European Patent No. 3703818 (EP Application No. 18799655.8), filed on behalf of Dr. Luigi Rumi, dated Dec. 23, 2025.
Written Submission Under Rule 116EPC regarding European Patent No. 3703818 (EP Application No. 18799655.8), filed on behalf of Boult Wade Tennant LLP, dated Dec. 23, 2025.
Written Submission Under Rule 116EPC regarding European Patent No. 3703818 (EP Application No. 18799655.8), filed on behalf of Michaelski Hüttermann & Partner Patentanwalte mbD, dated Dec. 23, 2025.
Patentee's Submission Under Rule 116EPC regarding European Patent No. 3703818 (EP Application No. 18799655.8), filed on behalf of Sanofi Biotechnology, dated Dec. 23, 2025.
List of Consolidated References for Written Submissions and Patentee's Submission regarding European Patent No. 3703818 (EP Application No. 18799655.8), dated Jan. 27, 2026.
D1—Clinicaltrials.gov, "Evaluation of Dupilumab in Patients With Severe Steroid Dependent Asthma (VENTURE)," online archive of <https://clinicaltrials.gov/study/NCT02528214?intr=REGN668&cond=Asthma&rank=9 > ("NCT02528214") Version 38, Oct. 24, 2017.
D2—Wenzel S et al., "Dupilumab efficacy and safety in adults with uncontrolled persistent asthma despite use of medium-to-high dose inhaled corticosteroids plus a long-acting [32 agonist; a randomised double-blind placebo-controlled pivotal phase 2b dose-ranging trial," The Lancet (2016) 388(10039):31-44.
D2a—Supplementary Appendix to D2.
D3—Regeneron Press Release dated Oct. 31, 2017.
D4—Clinical trials.gov, "Evaluation of Dupilumab in Patients With Persistent Asthma (Liberty Asthma Quest)," online archive of <https://clinicaltrials.gov/study/NCT02414854> ("NCT02414854") Sep. 11, 2017.
D5—Regeneron Press Release, "Regeneron and Sanofi announce positive Dupilumab topline results from phase 3 trial in uncontrolled persistent asthma" Available from < https://investor.regeneron.com/news-releases/news-release-details/regeneron-andsanofi-announce-positive-dupilumab-topline-0> Sep. 11, 2017.
D6—Clinical trials.gov, "Dupilumab Compassionate Use Study" online archive of https://clinicaltrials.gov/study/NCT03020810 ("NCT03020810") Jan. 13, 2017.
D7—Chung KF., "Dupilumab: a potential new treatment for severe asthma", Lancet (2016) 2;388(10039):3-4.
D8 / D55—Bel EH et al., "Oral glucocorticoid-sparing effect of mepolizumab in eosinophilic asthma," N Engl J Med (2014) 371(13):1189-97.
D8a—Supplementary Appendix to D8.
D9—Nair P et al., "Oral Glucocorticoid-Sparing Effect of Benralizumab in Severe Asthma," N Engl J Med (2017) 376(25):2448-2458.
D9a—Supplementary Appendix to D9.
D10—Global Initiative for Asthma, "Global Strategy for Asthma Management and Prevention," Vancouver, GINA 2014. Available from.
D11—Fahy JV. "Type 2 inflammation in asthma—present in most, absent in many," Nat Rev Immunol (2015) (1):57-65.
D12—Donohue JF and Jain N, "Exhaled nitric oxide to predict corticosteroid responsiveness and reduce asthma exacerbation rates," Respir Med. (2012) D13-107(7):943-52.
D13—Hashimoto S and Bel EH, "Current treatment of severe asthma," Clin Exp Allergy (2012) 42(5):693-705.
D14—Clinicaltrials.gov, "Evaluation of Dupilumab in Patients With Severe Steroid Dependent Asthma (VENTURE)," Clinical Trial Protocol for NCT02528214.
D15—Brusselle G and Bracke K, "Targeting immune pathways for therapy in asthma and chronic obstructive pulmonary disease," Ann Am Thorac Soc. (2014) 11 Suppl 5:S322-8.
D16 / D67—WO 2015/127229 (Sanofi and Regeneron).
D17—Barranco et al., "Dupilumab in the management of moderate-to-severe asthma: the data so far", Therapeutics and Clinical Risk Management, Sep. 1, 2017, 13, 1139-1149.
D18—Brodlie et al., "The oral corticosteroid-sparing effect of omalizumab in children with severe asthma", Archives of Disease in Childhood, Jun. 9, 2012, 97, 604-609.
D19—Molimard et al., "Omalizumab reduces oral corticosteroid use in patients with severe allergic asthma: Real-life data", Jul. 5, 2010, 104, 1381-1385.
D20—EP 3 703 818 B1 (granted patent/"patent in suit").
D21—WO 2019/089473 (application as originally filed).
D22—Braunstahl et al. "Reduction in oral corticosteroid use in patients receiving omalizumab for allergic asthma in the real-world setting";BioMed Central, Allergy, Asthma & Clinical Immunology 2013, 9:47; http://www.aacijoumal.com/content/9/1/47.
D23—Wenzel et al.; "Dupilumab in Persistent Asthma with Elevated Eosinophil Levels"; The New England Journal of Medicine 2013; 368; 26.
D24—WO 2014/031610 AI.
D25—GINA "Pocket Guide for Asthma Management and Prevention"; Global Initiative for Asthma, 2016.
D26—Mash et al., 2001 "Inhaled versus oral steroids for adults with chronic asthma"; Cochrane Database of Systematic Reviews 2001, Issue 1. Art. No. CD002160. DOI: 10.1002/14651858.CD002160.
D27—Schellenberg et al., 2007 "Oral corticosteroids in asthma: A review of benefits and risks"; Can Respir J 2007;14 (Suppl C):1C-7C.
D28—Luskin et al., 2016; "Health care resource use and costs associated with possible side effects of high oral corticosteroid use in asthma: a claims-based analysis"; ClinicoEconomics and Outcomes Research 2016:8 641-648.
D29—Lin et al., 2016; "A review of omalizumab for the management of severe asthma"; Drug Design, Development and Therapy 2016:10 2369-2378.
D30—Barnes et al., 2003; "How do corticosteroids work in asthma?", Ann. Intern. Med ; 2003 ; 139 : 359-37.
D31—Dupixent Label 2017.
D32—Austin D et al. European Respiratory Journal 2016 48 PA1100.
D33—Ray A et al. J Clin Invest. 2016;126(7):2394-2403.
D34—pp. 401, 402 and 412 of WHO Drug Information, 2012, 26(4):401-471.
D35—Shirley M Drugs (2017) 77:1115-1121.
D36 / D65—Santini G et al. Expert Opinion on Investigational Drugs, 26(3):357-366, published online on Feb. 7, 2017.
D37—Pollart et al., 2009.
D38—Wenzel 2005.
D39—Al-Ramli et al., 2008.
D40—ESR EP3470432 2018.
D41—Gina Report 2016.
D42—Pavord et al., 2012.
D43—Bum bacea et al., 2004.
D44—Kharitonov et al., 1997.
D45—Normansell et al., 2016.
D46—trial protocol of Sep. 28, 2017 of clinical trial NCT01000506.
D47—U.S. Appl. No. 62/579,120, filed Oct. 30, 2017 (also referred to as "Prio 1").
D48—U.S. Appl. No. 62/710,381, filed Feb. 16, 2018 (also referred to as "Prio 2").
D49—U.S. Appl. No. 62/647,368, filed Mar. 23, 2018 (also referred to as "Prio 3").
D50—EP 18305566.4, filed on May 4, 2018 (also referred to as "Prio 4").
D51—U.S. Appl. No. 62/742,736, filed Oct. 8, 2018 (also referred to as "Prio 5").
D52—Rabe K.F. et al., "Efficacy and Safety of Dupilumab in Glucocorticoid- Dependent Severe Asthma", N Engl J Med. Jun. 28, 2018; 378(26):2475-2485. doi: 10.1056/NEJMoal804093. Epub May 21, 2018.

(56) References Cited

OTHER PUBLICATIONS

D52a—Supplementary Appendix of TM7 (Rabe et al.).
D52b—Clinical trial protocol of the study of D1, published together with D1 on May 21, 2018.
D53—WHO Drug Information vol. 26(4), 412, Dec. 9, 2012.
D54—Nguyen V.Q. and Ulrik C.S., "Measures to reduce maintenance therapy with oral corticosteroid in adults with severe asthma", Allergy Asthma Proc. Nov. 2016; 37(6): 125-139.
D56—Siergiejko Z. et al., "Oral corticosteroid sparing with omalizumab in severe allergic IgE-mediated) asthma patients", Curr Med Res Opin. Nov. 2011;27(11):2223-8. doi: 10.1185/03007995.201 1.620950. Epub Sep. 2, 20111.
D57—Woodruff P.G et al., "T-helper type 2-driven inflammation defines major subphenotypes of asthma", Am J Respir Crit Care Med. Sep. 1, 2009;180(5):388-95. doi: 10.1164/rccm.200903-0392OC. Epub May 29, 2009. Erratum in: Am J Respir Crit Care Med. Oct. 15, 2009;180(8):796. PMID: 19483109; PMCID: PMC2742757.
D58—Wenzel SE, "Asthma phenotypes: the evolution from clinical to molecular approaches", Nat Med. May 4, 2012;18(5):716-25. doi: 10.1038/nm.2678. PMID: 22561835 (also referred to as "Wenzel, 2012").
D59—Haldar P et al., "Cluster analysis and clinical asthma phenotypes", Am J Respir Crit Care Med. Aug. 1, 2008,178(3):218-224. doi: 10.1164/rccm.200711-1754OC. Epub May 1, 20084. PMID: 18480428; PMCID: PMC3992366.
D60—Miskoff J.A. et al., "Fractional Exhaled Nitric Oxide Testing: Diagnostic Utility in Asthma, Chronic Obstructive Pulmonary Disease, or Asthma-chronic Obstructive Pulmonary Disease Overlap Syndrome", Cureus. Jun. 1, 2019 O; 11(6):e4864. doi: 10.7759/cureus.4864. PMID: 31417809; PM CID: PMC6690504.
D61—Dweik R.A. et al., "An official ATS clinical practice guideline: interpretation of exhaled nitric oxide levels (FENO) for clinical applications", Am J Respir Crit Care Med. 2011, 184:602-15. 10.1164/rccm.9120-IIST.
D62—"Global Strategy for Asthma Management and Prevention", Global Initiative for Asthma (GINA), 2009.
D63—Bleecker E.R. et al. Efficacy and safety of benralizumab for patients with severe asthma uncontrolled with high-dosage inhaled corticosteroids and long-acting E2-agonists (SIROCCO): a randomised, multicentre, placebo-controlled phase 3 trial. Lancet. Oct. 29, 2016,388(10056):2115-2127. doi: 10.1016/S0140-6736(16)31324-1. Epub Sep. 5, 2016. PMID: 27609408.
D64—Ortega I-LG et al. Mepolizumab treatment in patients with severe eosinophilic asthma. N Engl J Med. Sep. 25, 2014;371(13):1198-207. doi: 10.1056/NEJMoa1403290. Epub Sep. 8, 2014. Erratum in: N Engl J Med. Apr. 30, 2015;372(18):1777. doi: 10.1056/NEJMxl 50017. PMID: 25199059.
D66—Pelaia C. et al., Expert Opinion on Biological Therapy, 17(12):1565-1572, published online on Oct. 8, 2017.
D67 / D16—WO 2015/127229 A1, published Aug. 27, 2015.
D68—Bernstein et al., (2020) Lancet Respir Med.: 8; 461-474.
D69—Wechsler et al., (2022) Lancet Respir Med.: 10; 650-660.
D70—Busse et al., (2019) Eur Respir J 2018: 53: 1800948.
D71—Agache et al., Allergy, 2020; 75:1023-1042.
Annex I—Declaration and CV of Prof. M.D. Ph.D. Dsc Felix JF Herth, dated Dec. 11, 2025.
Taylor et al., 2008; "A new perspective on concepts of asthma severity and control", European Respiratory Journal, vol. 32, pp. 545-554.
Reddel et al., 2009; "An official American Thoracic Society/European Respiratory Society statement: asthma control and exacerbations: standardizing endpoints for clinical asthma trials and clinical practice", Am. J. Respir. Crit. Care Med; 180; pp. 59-99;.
Chung et al., 2014; International ERS/ATS Guidelines on Defintion, Evaluation and Treatment of Severe Asthma, Eur. Respir. J.; 43; pp. 343-373.
Shaw et al., 2015, "Clinical and inflammatory characteristics of the European U-Biopred adult severe asthma cohort", Eur. Respir. J.; 46; pp. 1308-1321.
Hekking et al., 2015; "The prevalence of severe refractory asthma", Journal of Allergy and Clinical Immunology, 135(4), pp. 896-902.
Han et al., 2017; "Efficacy and safety of dupilumab for the treatment of adult atopic dermatitis: A meta-analysis of randomized clinical trials", J. Allergy Clin. Immunol. 888-891.
D32—Austin et al. "Blood Eosinophil dose response to oral corticosteroids in a population of patients with severe asthma", European Respiratory Journal, 2016, 48: PA1100.
D35—Shirley, Dupilumab: First Global Approval, Drugs, 2017, 77: 1115-1121.
D38—Wenzel, "Severe Asthma in Adults", Am J Respir Crit Care Med., 2005, 172: 149-160.
D44—Kharitonov et al., Exhaled and Nasal Nitric Oxide Measurements: Reccomendations, Eur. Respir J., 1997, 10: 1683-1693.
D46—ClinicalTrials.gov, Trial protocol of Sep. 28, 2017 for ClinicalTrials.gov ID NCT01000506.
D56—Siergiejko Z. et al., "Oral corticosteroid sparing with omalizumab in severe allergic IgE-mediated) asthma patients", Curr Med Res Opin. Nov. 2011; 27(11):2223-8. doi: 10.1185/03007995.201 1.620950. Epub Sep. 21, 2011.
D66—Pelaia C. et al., "Dupilumab for the treatment of asthma", Expert Opinion on Biological Therapy, Dec. 2017, 17(12): 1565-1572, Epublished Oct. 8, 2017.
D72—Sweeney et al., "Comorbidity in severe asthma requiring systemic corticosteroid therapy: cross-sectional data from the Optimum Patient Care Research Database and the British Thoracic Difficult Asthma Registry", Thorax, Apr. 2016, 71(4): 339-346, Epublished Jan. 27, 2016.
D73—Choo et al., "Morbidity associated with oral corticosteroids in opatients with severe asthma", Thorax, Apr. 2016, 71(4): 302-304, Epublished Feb. 22, 2016.
D74—Pollart et al., "Overview of changes to asthma guidelines: diagnosis and screening", American Family Physician, May 1, 2009, 79(9): 761-767.
D75—Altman et al., "Absence of evidence is not evidence of absence", BMLJ, Aug. 19, 1995, 311: 485.
D76—Declaration of Prof. Ian Pavord, Dec. 17, 2025.
D76a—List of Publications by Prof. Ian Pavord.
D77—Hanania et al., "Omazumilab in Severe Allergic Asthma ladequately Controlled with Standard Therapy", Annals of Internal Medicine, May 3, 2011, 154(9): 573-582 & W-200-W-202.
D78—Normansell et al., Omazumilab for asthma in adults and children (review), Cochrane Library, 2014.
D79—Shiner et al., "Randomised, double-blind, placebo-controlled trial of Methotrexate in steroid-dependent asthma", The Lancet, 1990, 336: 137-140.
D80—Fajt et al., "Development of New Therapies for Severe Asthma", Allergy Asthma Immunol Res., Jan. 2017, 9(1): 3-14.
D81—Holgate et al., "Effects of omalizumab on markers of inflammation in patients with allergic asthma", Allergy, Dec. 2009, 64(12): 1728-1736.
D82—Busse et al., "Omalizumab, anti-IgE recombinant humanized monoclonal antibody, for the treatment of severe allergic asthma", J. Allergy Clin Immunol., 108(2): 184-190.

* cited by examiner

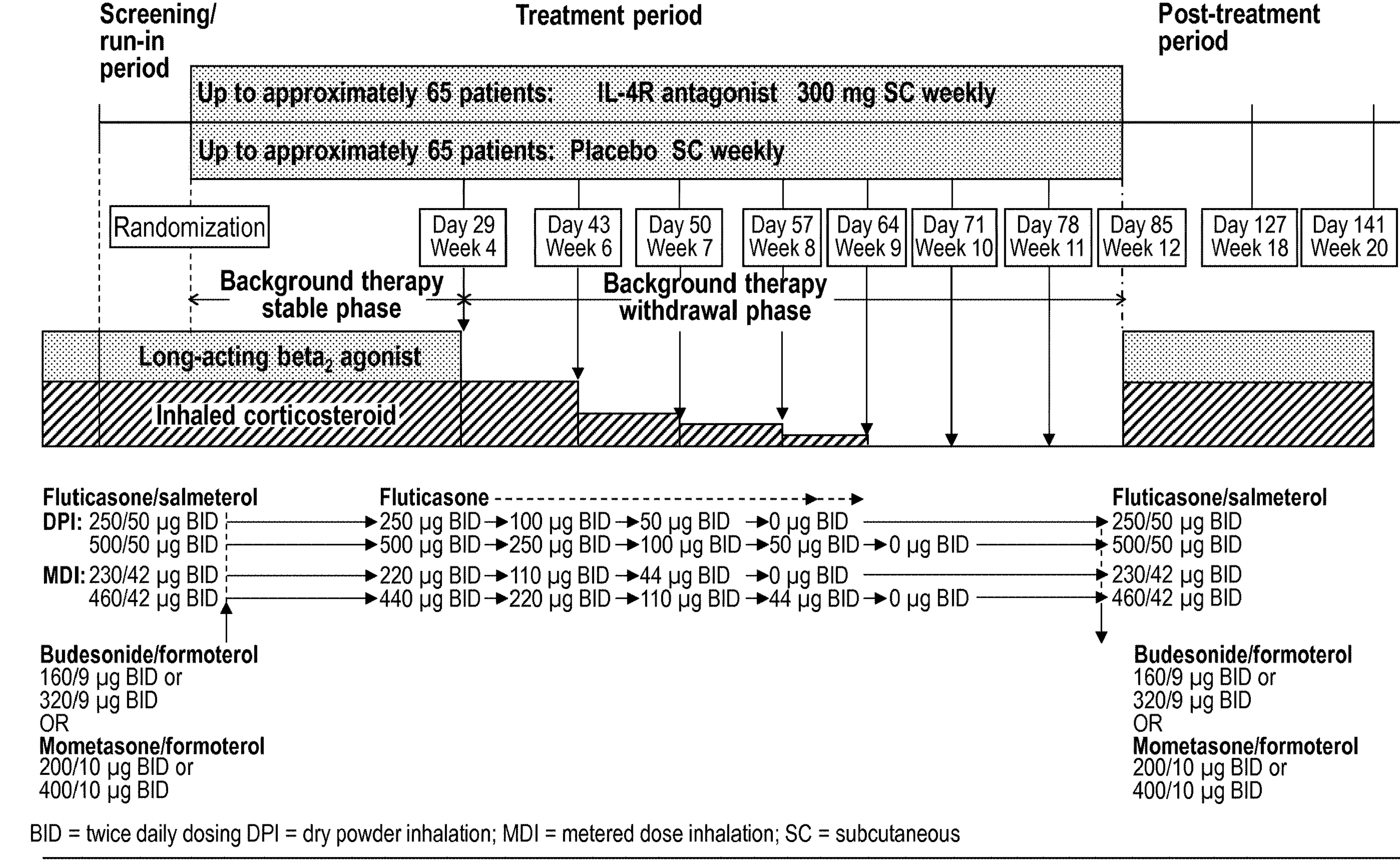

Screening/ run-in period
Treatment period
Post-treatment period
Up to approximately 65 patients: IL-4R antagonist 300 mg SC weekly
Up to approximately 65 patients: Placebo SC weekly
Randomization
Day 29 Week 4
Day 43 Week 6
Day 50 Week 7
Day 57 Week 8
Day 64 Week 9
Day 71 Week 10
Day 78 Week 11
Day 85 Week 12
Day 127 Week 18
Day 141 Week 20
Background therapy stable phase
Background therapy withdrawal phase
Long-acting beta$_2$ agonist
Inhaled corticosteroid
Fluticasone/salmeterol
DPI: 250/50 µg BID
500/50 µg BID
MDI: 230/42 µg BID
460/42 µg BID
Fluticasone
250 µg BID → 100 µg BID → 50 µg BID → 0 µg BID
500 µg BID → 250 µg BID → 100 µg BID → 50 µg BID → 0 µg BID
220 µg BID → 110 µg BID → 44 µg BID → 0 µg BID
440 µg BID → 220 µg BID → 110 µg BID → 44 µg BID → 0 µg BID
Fluticasone/salmeterol
250/50 µg BID
500/50 µg BID
230/42 µg BID
460/42 µg BID
Budesonide/formoterol
160/9 µg BID or
320/9 µg BID
OR
Mometasone/formoterol
200/10 µg BID or
400/10 µg BID
Budesonide/formoterol
160/9 µg BID or
320/9 µg BID
OR
Mometasone/formoterol
200/10 µg BID or
400/10 µg BID
BID = twice daily dosing DPI = dry powder inhalation; MDI = metered dose inhalation; SC = subcutaneous

SEQUENCE LISTING

```
<160> NUMBER OF SEQ ID NOS: 8

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      HCVR polypeptide

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120


<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      LCVR polypeptide

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30
```

```
Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110


<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR1 peptide

<400> SEQUENCE: 3

Gly Phe Thr Phe Arg Asp Tyr Ala
1               5


<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR2 peptide

<400> SEQUENCE: 4

Ile Ser Gly Ser Gly Gly Asn Thr
1               5


<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      HCDR3 peptide

<400> SEQUENCE: 5

Ala Lys Asp Arg Leu Ser Ile Thr Ile Arg Pro Arg Tyr Tyr Gly Leu
1               5                   10                  15

Asp Val


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR1 peptide

<400> SEQUENCE: 6

Gln Ser Leu Leu Tyr Ser Ile Gly Tyr Asn Tyr
1               5                   10


<210> SEQ ID NO 7
<211> LENGTH: 3
<212> TYPE: PRT
<213> ORGANISM: Artificial Sequence
```

-continued

```
<220> FEATURE:
<223> OTHER INFORMATION: Description of Artificial Sequence: Synthetic
      LCDR2 peptide

<400> SEQUENCE: 7

Leu Gly Ser
1


<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      LCDR3 peptide

<400> SEQUENCE: 8

Met Gln Ala Leu Gln Thr Pro Tyr Thr
1               5
```

METHODS FOR TREATING NASAL POLYPOSIS BY ADMINISTERING AN IL-4R ANTAGONIST

RELATED APPLICATIONS

This application is a continuation of U.S. patent application Ser. No. 14/310,419, filed Jun. 20, 2014, now U.S. Pat. No. 10,059,771, which claims the benefit of U.S. Provisional Application Ser. No. 61/837,912, filed Jun. 21, 2013, and European Patent Application No. 14305670.3, filed May 7, 2014, each of which are incorporated herein by reference in their entirety.

FIELD OF THE INVENTION

The present invention relates to the field of therapeutic treatments of inflammatory conditions. More specifically, the invention relates to the administration of interleukin-4 receptor (IL-4R) antagonists to treat nasal polyposis.

BACKGROUND

Nasal polyposis (NP) is a clinical condition characterized by the presence of multiple polyps in the upper nasal cavity, originating from the ostiomeatal complex. NP is a T helper cell-2 (Th-2) driven inflammatory process affecting the mucosa of the nose and paranasal sinuses. Eosinophils and their products are thought to be a hallmark of nasal polyp-associated inflammation as elevated levels of interleukin-5 (IL-5; promotes eosinophil survival and differentiation), eosinophil cationic protein (ECP), and eotaxin (eosinophil chemoattractant), factors that attract and activate eosinophils, are typically found in nasal polyps. Eosinophils are the predominant inflammatory cell found in the sinuses and nasal polyps, and nasal polyps are also associated with elevated levels of IgE. NP is characterized by long-term symptoms of nasal obstruction and congestion, reduction in or loss of sense of smell, anterior and posterior rhinorrhea, and facial pain. Current treatment options range from local or systemic corticosteroids to functional endoscopic sinus surgery.

BRIEF SUMMARY OF THE INVENTION

In one aspect, the invention provides a method for treating nasal polyposis, where the method includes administering to a subject in need thereof a pharmaceutical composition containing an interleukin-4 receptor (IL-4R) antagonist, such as an anti-IL-4R antibody or antigen-binding fragment thereof. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

A subject suitable for treatment with an IL-4R antagonist may have one or more of sinusitis, rhinitis, asthma, aspirin hypersensitivity, non-steroidal anti-inflammatory drug (NSAID) hypersensitivity, or have previously undergone surgery to treat nasal polyposis. In some embodiments, the subject has chronic sinusitis or chronic rhinosinusitis. For example, the subject may have nasal polyposis with severe symptoms of sinusitis.

In some embodiments, the IL-4R antagonist is administered at a dose of 0.1 mg to 600 mg (e.g., 100 mg to 400 mg, such as 150 mg, 200 mg, 250 mg, 300 mg or 350 mg). In certain embodiments, the pharmaceutical composition is administered to the subject systemically or locally. For example, the pharmaceutical composition may be administered subcutaneously, intravenously, or intranasally.

In one embodiment, the pharmaceutical composition is administered to the subject subcutaneously at a dose of 300 mg.

In certain embodiments, one or more additional therapeutic agents are administered to the subject before, after or concurrent with the pharmaceutical composition comprising the IL-4R antagonist, such as the IL-4R antibody or antigen-binding fragment thereof. For example, in one embodiment, the one or more additional agents, such as a second therapeutic agent can be a TNF inhibitor, an IL-1 inhibitor, an IL-5 inhibitor, an IL-8 inhibitor, an IgE inhibitor, an NSAID (non-steroidal anti-inflammatory drug), an antibiotic, an anti-fungal agent, an intranasal corticosteroid, an inhaled corticosteroid, a systemic corticosteroid, a long-acting $beta_2$ agonist, a decongestant, or any combination thereof. In one embodiment, the second therapeutic agent is an inhaled corticosteroid, such as fluticasone or budesonide, or an intranasal corticosteroid, such as mometasone furoate nasal spray (MFNS). In another embodiment, the second therapeutic agent further includes a long-acting $beta_2$ agonist, such as salmeterol or formoterol.

In certain embodiments, administration of the IL-4R antagonist is followed by an improvement in one or more symptoms of nasal polyposis. For example, the administration of the antagonist can be followed by an improvement in one or more nasal polyposis-associated parameters, such as an improvement in a 22-item Sinonasal Outcome Test (SNOT-22) score; a nasal symptom score; number of nocturnal awakenings; a Visual Analog Score (VAS), such as for rhinosinusitis symptom severity; a five-item Asthma Control Questionnaire (ACQS) score; nasal peak inspiratory flow (NPIF); the University of Pennsylvania Smell Identification Test (UPSIT); Lund-McKay Score; and three dimensional volumetric measurement of the maxillary sinus. In certain embodiments, administration of the antibody or antigen binding fragment thereof is followed by one or more of an increase in one or both of NPIF and UPSIT, and a decrease in one or more of SNOT-22 score, nasal symptom score, VAS, Lund-McKay Score and 3D-Volumetric Score. In some embodiments, administration of the IL-4R antagonist is followed by a decrease in nasal polyp score in the patient.

In one aspect, the invention provides a method for treating nasal polyposis, by sequentially administering to a subject in need thereof a single initial dose of an interleukin-4 receptor (IL-4R) antagonist, such as an IL-4R antibody or an antigen-binding fragment thereof, followed by one or more secondary doses of the IL-4R antagonist. In some embodiments, each secondary dose is administered 1 to 15 weeks after the immediately preceding dose. In other embodiments, at least three secondary doses of the IL-4R antagonist are administered to the subject, and each secondary dose is administered days or weeks (e.g., 1 week or 2 weeks or more) after the immediately preceding dose. In another embodiment, the initial dose and the one or more secondary doses each include 50 mg to 500 mg of the IL-4R antagonist, e.g., 100 mg to 400 mg of the IL-4R antagonist, e.g., 150 mg, 200 mg, 250 mg, 300 mg, or 350 mg of the IL-4R antagonist. In some embodiments, the initial dose and the one or more secondary doses each contain the same amount of the IL-4R antagonist. In other embodiments, the initial dose comprises a first amount of the IL-4R antagonist, and the one or more secondary doses each comprise a second amount of the IL-4R antagonist. For example, the first amount of the IL-4R antagonist can be 1.5×, 2×, 2.5×, 3×, 3.5×, 4× or 5× or more than the second amount of IL-4R antagonist.

In one embodiment, the subject (e.g., a patient) has one or more of sinusitis, rhinitis, asthma, aspirin hypersensitivity, non-steroidal anti-inflammatory drug (NSAID) hypersensitivity, or has undergone surgery for nasal polyps. In some embodiments, the subject has chronic sinusitis or chronic rhinosinusitis. For example, the subject may have nasal polyposis with severe symptoms of sinusitis.

The initial dose and the secondary doses of the IL-4R antagonist can be administered by the same or different routes of administration. For example, the initial dose and the secondary doses can be administered subcutaneously, intravenously, or intranasally.

In certain embodiments, administration of the initial dose and the one or more secondary doses is followed by an improvement in one or more nasal polyposis associated parameters, such as an improvement in a 22-item Sinonasal Outcome Test (SNOT-22) score; a nasal symptom score; number of nocturnal awakenings; a Visual Analog Score (VAS), such as for rhinosinusitis symptom severity; a five-item Asthma Control Questionnaire (ACQS) score; nasal peak inspiratory flow (NPIF); the University of Pennsylvania Smell Identification Test (UPSIT); Lund-McKay Score; and three dimensional volumetric measurement of the maxillary sinus. In certain embodiments, administration of the antibody or antigen binding fragment thereof is followed by one or more of an increase in one or both of NPIF and UPSIT, and a decrease in one or more of SNOT-22 score, nasal symptom score, VAS, Lund-McKay Score and 3D-Volumetric Score. In some embodiments, administration of the IL-4R antagonist is followed by a decrease in nasal polyp score in the patient.

In certain embodiments, one or more additional therapeutic agents are administered to the subject before, after or concurrent with the pharmaceutical composition comprising the IL-4R antagonist, such as the IL-4R antibody or antigen-binding fragment thereof. For example, in one embodiment, the one or more additional agents, such as a second therapeutic agent can be a TNF inhibitor, an IL-1 inhibitor, an IL-5 inhibitor, an IL-8 inhibitor, an IgE inhibitor, an NSAID, an antibiotic, an anti-fungal agent, an intranasal corticosteroid, an inhaled corticosteroid, a systemic corticosteroid, a long-acting beta$_2$ agonist, a decongestant, or any combination thereof. In one embodiment, the second therapeutic agent is an inhaled corticosteroid, such as fluticasone or budesonide, or an intranasal corticosteroid, such as mometasone furoate nasal spray (MFNS). In another embodiment, the second therapeutic agent further includes a long-acting beta$_2$ agonist, such as salmeterol or formoterol.

In one aspect, the invention provides a method for treating nasal polyposis, by selecting a patient with a minimum bilateral nasal polyp score of 5, or at least two or more of the chronic symptoms of sinusitis selected from the group consisting of: nasal blockade/obstruction/congestion, anterior or posterior nasal drip, facial pain or pressure, and reduction or loss of smell; and administering to the selected patient a pharmaceutical composition comprising an interleukin-4 receptor (IL-4R) antagonist, such as antibody or antigen-binding fragment thereof that specifically binds an interleukin-4 receptor (IL-4R), such that the patient's nasal polyp score is reduced or the two or more chronic symptoms of sinusitis are improved. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

In one aspect, the invention provides a method for treating nasal polyposis, by selecting a patient with a minimum bilateral nasal polyp score of 5, or at least two or more of the chronic symptoms of sinusitis selected from the group consisting of: nasal blockade/obstruction/congestion, anterior or posterior nasal drip, facial pain or pressure, and reduction or loss of smell; and sequentially administering to the patient a single initial dose of a pharmaceutical composition an interleukin-4 receptor (IL-4R) antagonist, such as antibody or antigen-binding fragment thereof that specifically binds an interleukin-4 receptor (IL-4R), followed by one or more secondary doses of the antibody or antigen binding fragment thereof, such that the patient's nasal polyp score is reduced or the two or more chronic symptoms of sinusitis are improved. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

In one aspect, the invention provides a method for treating nasal polyposis, by determining in a subject the expression level of one or more genes selected from the group consisting of thymus and activation-regulated chemokine (TARC), eotaxin-3, periostin, carcinoembryonic antigen (CEA), and YKL-40; selecting the subject as a candidate for treatment with an interleukin-4 receptor (IL-4R) antagonist, such as antibody or antigen-binding fragment thereof that specifically binds an interleukin-4 receptor (IL-4R), if the subject has an elevated expression level of the one or more genes; and administering to the selected subject a pharmaceutical composition comprising an antibody or antigen binding fragment thereof that specifically binds an interleukin-4 receptor (IL-4R), such that the level of the one or more genes is reduced. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

In one aspect, the invention provides a method for treating nasal polyposis, by determining in a subject the expression level of one or more genes selected from the group consisting of thymus and activation-regulated chemokine (TARC), eotaxin-3, periostin, carcinoembryonic antigen (CEA), and YKL-40; selecting the subject as a candidate for treatment with an interleukin-4 receptor (IL-4R) antagonist, such as antibody or antigen-binding fragment thereof that specifically binds an interleukin-4 receptor (IL-4R), if the subject has an elevated expression level of the one or more genes; and sequentially administering to the selected subject a single initial dose of a pharmaceutical composition comprising an interleukin-4 receptor (IL-4R) antagonist, such as antibody or antigen-binding fragment thereof that specifically binds an interleukin-4 receptor (IL-4R), followed by one or more secondary doses of the antibody or antigen binding fragment thereof, such that the level of the one or more genes is reduced. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

In one aspect, the invention provides a method for treating nasal polyposis, by determining in a subject the level of blood eosinophils or sputum eosinophils; selecting the subject as a candidate for treatment with an interleukin-4 receptor (IL-4R) antagonist, such as antibody or antigen-binding fragment thereof that specifically binds an interleukin-4 receptor (IL-4R), if the subject has an elevated level of blood eosinophils or sputum eosinophils; and administering to the selected subject a pharmaceutical composition comprising an interleukin-4 receptor (IL-4R) antagonist, such as antibody or antigen-binding fragment thereof that specifically binds an interleukin-4 receptor (IL-4R), such that the level of blood eosinophils or sputum eosinophils is reduced. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

In one aspect, the invention provides a method for treating nasal polyposis, by determining in a subject the level of blood eosinophils or sputum eosinophils; selecting the subject as a candidate for treatment with an interleukin-4 receptor (IL-4R) antagonist, such as antibody or antigen-binding fragment thereof that specifically binds an interleukin-4 receptor (IL-4R), if the subject has an elevated level of blood eosinophils or sputum eosinophils; and sequentially administering to the selected subject a single initial dose of a pharmaceutical composition comprising an interleukin-4 receptor (IL-4R) antagonist, such as antibody or antigen-binding fragment thereof that specifically binds an interleukin-4 receptor (IL-4R), followed by one or more secondary doses of the antibody or antigen binding fragment thereof, such that the level of blood eosinophils or sputum eosinophils is reduced. In one embodiment, the IL-4R antagonist is an antibody or antigen-binding fragment thereof that specifically binds IL-4Rα, such as an antibody or antigen binding fragment that comprises heavy and light chain CDR sequences from a heavy chain variable region (HCVR) of SEQ ID NO:1, and a light chain variable region (LCVR) of SEQ ID NO:2. For example, in one embodiment, the antibody or antigen binding fragment thereof comprises heavy chain CDR sequences of SEQ ID NOs:3, 4, and 5, and light chain CDR sequences of SEQ ID NOs:6, 7 and 8. For example, in one embodiment, the antibody or antigen-binding fragment thereof comprises an HCVR having the amino acid sequence of SEQ ID NO:1 and an LCVR having the amino acid sequence of SEQ ID NO:2. In one embodiment, the IL-4R antagonist is dupilumab or an antigen-binding fragment thereof. Other exemplary anti-IL-4R antibodies or antigen-binding fragments thereof are described, for example, in U.S. Pat. Nos. 7,605,237 and 7,608,693.

Other embodiments will become apparent from the below FIGURE and the Detailed Description.

BRIEF DESCRIPTION OF THE FIGURES

FIG. 1 shows the schematic representation of an example of background therapy withdrawal time period in the treatment of an asthma patient.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

All publications mentioned herein are incorporated herein by reference in their entirety.

Methods for Treating Nasal Polyposis

The present invention provides methods for treating nasal polyposis. As used herein, a "nasal polyp" is an overgrowth of tissue in one or more of the nasal cavities. The condition of nasal polyps is called "nasal polyposis." About 80% of nasal polyps are highly edematous and filled with eosinophils. Nasal polyps can also present as fibrous, glandular or cystic.

Nasal polyposis (NP) is a clinical condition characterized by the presence of multiple polyps in the upper nasal cavity, originating from the ostiomeatal complex. NP is a T helper cell-2 (Th-2) driven inflammatory process affecting the mucosa of the nose and paranasal sinuses. Eosinophils and their products are thought to be a hallmark of nasal polyp-associated inflammation as elevated levels of interleukin-5 (IL-5; promotes eosinophil survival and differentiation), eosinophil cationic protein (ECP), and eotaxin (eosinophil chemoattractant), factors that attract and activate eosinophils, are typically found in nasal polyps. Eosinophils are the predominant inflammatory cell found in the sinuses and nasal polyps, and nasal polyps are also associated with elevated levels of IgE.

NP is characterized by long-term symptoms of nasal obstruction and congestion, reduction in or loss of sense of smell, anterior and posterior rhinorrhea, and facial pain. The presence or absence of nasal polyps can be confirmed for example by performing endoscopy, and the presence and extent of sinus and polyp involvement can be confirmed by methods such as coronal computed tomography (CT) scans.

An IL-4R antagonist can be used to treat nasal polyposis associated with a variety of conditions. For example, nasal polyposis is associated with sinusitis, rhinitis (e.g., allergic and non-allergic rhinitis), asthma (e.g., moderate-to-severe asthma), NSAID sensitivity (e.g., aspirin sensitivity), and infection, such as bacterial and fungal infection. Bacterial infections include, for example, *staphylococcus* infections. A subject with nasal polyposis can have a chronic infection, such as a chronic bacterial infection, e.g., a chronic *staphylococcus aureus* infection. In some embodiments, the subject has recurring nasal polyposis, such as may be associated with recurring sinusitis. In other embodiments, the subject as cystic fibrosis or NARES (Non-Allergic Rhinitis with Eosinophilia Syndrome). In other embodiments, the subject has a relapse of nasal polyposis after receiving surgery to treat the polyps. Risk factors for nasal polyposis include genetic susceptibility, anatomic abnormality, mucociliary impairment, infection, and local immunologic imbalance.

An IL-4R antagonist can also be used to treat nasal polyposis in patients who have never previously received a treatment or surgery for NP. An IL-4R antagonist can also be used to treat nasal polyposis in patients who have previously undergone surgery, such as a nasal surgery, such as for treatment of nasal polyps. In certain embodiments, an IL-4R antagonist is administered to a subject whose nasal polyposis has relapsed after the subject received prior treatment for the polyps, such as a prior nasal surgery.

As used herein, the term "sinusitis" refers to any inflammatory condition characterized by inflammation of the paranasal sinuses, including inflammation of the maxillary, frontal, ethmoid and/or sphenoid paranasal sinuses. An IL-4R antagonist is suitable for treatment of nasal polyposis is associated with acute sinusitis, subacute sinusitis, chronic sinusitis and recurrent sinusitis. Acute sinusitis is characterized by a sudden onset of cold-like symptoms such as runny, stuffy nose and facial pain that does not go away after 10 to 14 days. Acute sinusitis typically lasts less than four weeks. Subacute sinusitis lasts four to eight weeks. Chronic sinusitis lasts eight weeks or longer, and recurrent sinusitis is characterized by sinusitis episodes that occur three or more times in one year. More than 80% of patients with chronic sinusitis with nasal polyps have eosinophilic upper airway inflammation.

Many patients with chronic sinusitis have "chronic hyperplastic eosinophilic sinusitis," which is characterized by marked inflammation of the sinuses, increased eosinophils and mixed mononuclear cells, and a relative paucity of neutrophils. Some of these patients have one or more of associated nasal polyps, asthma, and aspirin or NSAID sensitivity. In certain embodiments, an IL-4R antagonist can be used to treat nasal polyposis in a subject who has chronic hyperplastic eosinophilic sinusitis.

The term "rhinitis" refers to an allergic response, such as to a common allergen ("allergic rhinitis," e.g., perennial allergic rhinitis) or to an environmental irritant ("non-allergic rhinitis"). Symptoms of allergic rhinitis include sneezing; stuffy or runny nose; sinus pressure, and pain or throbbing in the cheeks or nose; and itching in the nose, throat, eyes and ears.

Symptoms of non-allergic rhinitis include constriction or inflammation in the nasal passages which leads to many of the same symptoms of allergic rhinitis. Non-allergic rhinitis can be caused, for example, by strong chemical or smoky environments, or by long-term use of certain medications or dependency on nasal sprays.

As used herein, the term "rhinosinusitis" refers to a condition that has symptoms of both rhinitis and sinusitis. Rhinosinusitis includes acute rhinosinusitis and chronic rhinosinusitis. Acute rhinosinusitis can be caused by an infection, such as a bacterial, viral or fungal infection, or by a chemical irritation. Cigarette-smoke-induced acute rhinosinusitis and chlorine fume-induced chronic rhinosinusitis are examples of acute rhinosinusitis. NP is most commonly associated with chronic rhinosinusitis (CRS), which is characterized by mucosal inflammation of the nasal cavity and paranasal sinuses with symptoms lasting more than 8 weeks. Chronic eosinophilic rhinosinusitis with nasal polyps is a condition that lasts longer than 8 weeks.

Chronic sinusitis (CS) and chronic rhinosinusitis (CRS) are conditions that last longer than eight weeks. The underlying causes of acute sinusitis and acute rhinosinusitis may lead to chronic sinusitis or chronic rhinosinusitis if the resulting inflammation persists for more than 8 weeks. Chronic rhinosinusitis includes for example, eosinophilic chronic hyperplastic rhinosinusitis.

Additional subcategories of chronic sinusitis (and chronic rhinosinusitis) include, e.g., superantigen-induced eosinophilic chronic sinusitis (e.g., sinusitis induced by exo- and endo-toxins produced by bacteria such as *Staphylococcus aureus*); allergic fungal sinusitis (e.g., sinusitis induced by fungi such as *Aspergillus* or *Alternaria*); non-allergic fungal eosinophilic chronic sinusitis; and aspirin-exacerbated eosinophilic chronic sinusitis.

An IL-4R antagonist can be used to treat nasal polyposis in subjects having any of the disorders described above.

Methods for Improving Nasal Polyp-Associated Parameters

The present invention includes methods for improving one or more nasal polyp-associated parameters in a subject in need thereof, wherein the methods include administering a pharmaceutical composition comprising an interleukin-4 receptor (IL-4R) antagonist to the subject. For example, an IL-4R receptor antagonist can reduce endoscopic nasal polyp score in a patient. A nasal polyp score of 0 indicates the presence of no polyps. A nasal polyp score of 1 indicates the presence of small polyps in the middle meatus not reaching below the inferior border of the middle turbinate. A nasal polyp score of 3 indicates large polyps reaching the lower border of the inferior turbinate or polyps medial to the middle turbinate. A nasal polyp score of 4 indicates large polyps causing complete obstruction of the inferior nasal cavity (see Table 15 below). The maximum score is 8 (4 points per nasal cavity). Treatment with an IL-4R antagonist can decrease nasal polyp score by about 1 to about 8 points. For example, treatment with an IL-4R antagonist can decrease nasal polyp score by about 1 point or more, by about 2 points or more, or by about 3 points or more. In some embodiments, treatment with an IL-4R antagonist can decrease nasal polyp score by about 1 point, or a fraction thereof; by 2 points, or a fraction thereof; by 3 points, or a fraction thereof; by 4 points, or a fraction thereof; by 5 points, or a fraction thereof; by 6 points, or a fraction thereof; by 7 points, or a fraction thereof; or by 8 points or a fraction thereof. A reduction in nasal polyp score may correlate with an improvement in one or more other nasal polyp-associated parameters. Such a correlation, however, is not necessarily observed in all cases.

Other examples of "nasal polyp-associated parameters" include: (a) 22-item SinoNasal Outcome Test (SNOT-22) score; (b) subject-assessed nasal congestion/obstruction, anterior rhinorrhea (runny nose), posterior rhinorrhea (post nasal drip) and loss of sense of smell; (c) number of nocturnal awakenings; (d) Visual Analog Score (VAS) to assess patient-rated rhinosinusitis symptom severity; (e) five-item Asthma Control Questionnaire (ACQS) score, such as in patients with asthma; (f) Nasal Peak Inspiratory Flow (NPIF); (g) smell test (University of Pennsylvania Smell Identification Test (UPSIT)); (h) physiological parameters, such as measured by nasal endoscopy and CT scan; (i) Lund-Mackay Score; and (j) Three Dimensional volumetric measurement of the maxillary sinus.

22-Item Sinonasal Outcome Test (SNOT-22) Score.

According to certain embodiments, administration of an IL-4R antagonist to a patient results in a decrease from baseline of 22-item Sinonasal Outcome Test (SNOT-22). The SNOT-22 is a questionnaire to assess the impact of chronic rhinosinusitis (CRS) on quality of life. The questionnaire measures items related to sinonasal conditions and surgical treatments. The score ranges from 0 to 110, and higher scores imply greater impact of CRS on Health Related Quality of Life (HRQoL) (Hopkins et al 2009, Clin. Otolaryngol. 34: 447-454).

The present invention includes therapeutic methods that result in a decrease in SNOT-22 score from baseline of at least 1 point at week 4 to week 16 following administration of the IL-4R antagonist. For example, administration of an IL-4R antagonist will result in a decrease in SNOT-22 score at week 4, week 6, week 8, week 12, or week 16 following initiation of treatment. In some embodiments, administration of an IL-4R antagonist to a subject in need thereof causes a decrease in SNOT-22 score from baseline of about 1, 2, 3, 4, 5, 6, 7, 8, 9, 10, 11, 12, 13 points, or more at week 4, week 6, week 8 or week 12.

Individual and Total Nasal Symptom Score.

Subject-assessed symptoms are assayed by responding to morning and evening individual rhinosinusitis symptom questions using a 0-3 categorical scale (where 0=no symptoms, 1=mild symptoms, 2=moderate symptoms and 3=severe symptoms), and including the symptoms of congestion and/or obstruction, anterior rhinorrhea, posterior rhinorrhea, and loss of sense of smell. A measure of night-time awakenings can also be tracked. For example, a measure of night-time awakenings can be assessed according to the following scores based on subject self-assessment: 0=no symptoms, slept through the night; 1=slept well, but some complaints in the morning; 2=woke up once because of rhinosinusitis symptoms (including early awakening); 3=woke up several times because of symptoms (including early awakening); 4=bad night, awake most of the night because of symptoms. Administration of an IL-4R antagonist can result, for example, in a decrease in average number of nighttime awakenings per night from baseline of at least about 0.10 times per night at week 4 to week 16 following initiation of treatment with a pharmaceutical composition comprising an anti-IL-4R antagonist. For example, a decrease in frequency of nighttime awakenings per night from baseline of at least about 0.10 times per night can be detected at week 4, week 6, week 8, week 12, or week 16 following initiation of treatment. Administration of an IL-4R antagonist to a subject in need thereof can cause a decrease in average number of nighttime awakenings per night from baseline by about 0.10 times per night, 0.15 times per night, 0.20 times per night, 0.25 times per night, 0.30 times per night, 0.35 times per night, 0.40 times per night, 0.45 times per night, 0.50 times per night, 0.55 times per night, 0.60 times per night, 0.65 times per night, 0.70 times per night, 0.75 times per night, 0.80 times per night, 0.85 times per night, 0.90 times per night, 0.95 times per night, 1.0 time per night, 2.0 times per night, or more at week 4, week 8, week 12, or week 16, for example.

Visual Analog Score (VAS).

The VAS is a measure to assess patient-related rhinosinusitis symptom severity on a scale of 1 to 10. Mild symptoms are indicated by a score of 0 to 3, moderate symptoms are indicated by a VAS score of >3 to 7, and severe symptoms are indicated by a VAS score of >7 to 10. Administration of an IL-4R antagonist to a subject in need thereof causes a decrease in VAS score from baseline of about 0.5 point, 1 point, 1.5 points, 2 points, 2.5 points, 3 points, 3.5 points, 4 points, or more at week 4, week 6 or week 12. The decrease in VAS score can be detected as early as week 4, and as late as week 12 or later following administration of the IL-4R antagonist.

5-Item Asthma Control Questionnaire (ACQ) Score.

The ACQS measures both the adequacy of asthma control and change in asthma control, which occurs either spontaneously or as a result of treatment. The five questions on the ACQS reflect the top-scoring five asthma symptoms: woken at night by symptoms, wake in the mornings with symptoms, limitation of daily activities, shortness of breath and wheeze. Patients respond to the symptom questions on a 7-point scale (0=no impairment, totally controlled; 6=maximum impairment, severely uncontrolled).

The present invention includes therapeutic methods which result in a decrease in ACQS score from baseline of at least 0.10 point at week 12 following initiation of treatment with a pharmaceutical composition comprising an anti-IL-4R antagonist. For example, according to the present invention, administration of an IL-4R antagonist to a subject in need thereof causes a decrease in ACQ score from baseline of about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 4, week 6 or week 12. The decrease in ACQ score can be detected as early as week 4, and as late as week 12 or later following administration of the IL-4R antagonist.

Nasal Peak Inspiratory Flow (NPIF).

The Nasal Peak Inspiratory Flow (NPIF) represents a physiologic measure of air flow through both nasal cavities during forced inspiration and/or expiration expressed in liters per minute. Nasal inspiration correlates most with the subjective feeling of obstruction and is used to monitor nasal flow. Administration of an IL-4R antagonist to a subject in need thereof causes an increase in NPIF from baseline by about 0.10 liters per minute, 0.15 liters per minute, 0.20 liters per minute, 0.25 liters per minute, 0.30 liters per minute, 0.35 liters per minute, 0.40 liters per minute, 0.45 liters per minute, 0.50 liters per minute, 0.55 liters per minute, 0.60 liters per minute, 0.65 liters per minute, 0.70 liters per minute, 0.75 liters per minute, 0.80 liters per minute, 0.85 liters per minute, or more at week 4, week 6 or week 12. The increase in NPIF score can be detected as early as week 4, and as late as week 12 or later following administration of the IL-4R antagonist.

University of Pennsylvania Smell Identification Test (UPSIT).

The UPSIT is a method to quantitatively assess human olfactory function. The test consists of samples of odorants, and the subject has to describe the odor. The score is based on the number of correct answers. This test can distinguish patients with a normal sense of smell ("normosmia") from those with different levels of reduction ("mild, moderate and severe microsmia") or loss ("anosmia"). Administration of an IL-4R antagonist to a subject in need thereof causes an increase in UPSIT score from baseline by about 0.5 points, 1 point, 1.5 points, 2 points, 2.5 points, 3 points, 3.5 points or more at week 4, week 6 or week 12. The increase in UPSIT score can be detected as early as week 4, and as late as week 12 or later following administration of the IL-4R antagonist.

Physiological Parameters.

Efficacy of an IL-4R antagonist can be assayed by measuring the effect of physiological parameters, such as within the nasal cavities, such as by nasal endoscopy or computed tomography (CT) scan.

Lund-Mackay Score.

The Lund-Mackay scoring system is based on localization with points given for degree of opacification: 0=normal, 1=partial opacification, 2=total opacification. These points are then applied to the maxillary, anterior ethmoid, posterior ethmoid, sphenoid, and frontal sinus on each side. The osteomeatal complex is graded as 0=not occluded, or 2=occluded deriving a maximum score of 12 per side. For patients in whom the osteomeatal complex (OC) is missing (because of a previous surgery) the location of the former OC is considered and a score is provided, as if the OC was there. Administration of an IL-4R antagonist to a subject in need thereof causes a decrease in Lund-Mackay score from baseline by about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 4, week 6 or week 12. The decrease in Lund-Mackay score can be detected as early as week 4, and as late as week 12 or later following administration of the IL-4R antagonist.

Three-Dimensional Volumetric Measurement of Maxillary Sinus.

This value is used to calculate the volume of air (mL); the volume of mucosa (mL); the percent sinus occupied by disease; and the thickness of lateral wall in the maxillary sinus. Administration of an IL-4R antagonist to a subject in need thereof causes an increase in the Three-Dimensional volumetric measurement.

Quality of Life (QoL) Questionnaires.

Various QoL Questionnaires can be used to monitor efficacy of an IL-4R antagonist, including Short-Form-36 (SF-36) Questionnaire, the Euroqol-5D (EQ-5D), nasal polyp related resource use questionnaire, and the patient qualitative self-assessment.

The SF-36 is a 36 item questionnaire that measures eight multi-item dimensions of health: physical functioning (10 items) social functioning (2 items) role limitations due to physical problems (4 items), role limitations due to emotional problems (3 items), mental health (5 items), energy/vitality (4 items), pain (2 items), and general health perception (5 items). For each dimension, item scores are coded, summed, and transformed on a scale from 0 (worst possible health state measured by the questionnaire) to 100 (best possible health state). Two standardized summary scores can also be calculated from the SF-36; the physical component summary (PCS) and the mental health component summary (MCS).

The EQ-5D is a standardized health-related quality of life questionnaire developed by the EuroQol Group in order to provide a simple, generic measure of health for clinical and economic appraisal and inter-disease comparisons. EQ-5D, designed for self-completion by patients, consists of two parts, the EQ-5D descriptive system and the EQ VAS. The EQ-5D descriptive system comprises 5 dimensions: mobility, self-care, usual activities, pain/discomfort and anxiety/depression; and each dimension has 3 levels: no problem, some problems, severe problems. The EQ Visual Analogue Scale (VAS) records the respondent's self-rated health on a vertical visual analogue scale. The EQ VAS 'thermometer' has endpoints of 100 (Best imaginable health state) at the top and 0 (Worst imaginable health state) at the bottom.

The nasal polyp related resource use questionnaire is a questionnaire of health care resource utilization for nasal polyposis, including specialist visits, emergency care visits, sick leaves, days off etc.

Improvement of a nasal polyp-associated parameter, such as a nasal polyp-associated parameter described above, can be expressed as a percentage. For example, a score can be improved by 30% or more, by 40% or more, by 50% or more, by 60% or more, by 70% or more, or by 80% or more.

An "improvement in a nasal polyp-associated parameter" means an increase from baseline of one or more of NP IF, UPSIT, and/or a decrease from baseline of one or more of SNOT-22 score, subject-assessed nasal congestion/obstruction, anterior rhinorrhea (runny nose), posterior rhinorrhea (post nasal drip) and loss of sense of smell; number of nocturnal awakenings; VAS score; Lund-Mackay score; and 3D volumetric scores; and ACQS score in patients with asthma. As used herein, the term "baseline," with regard to a nasal polyp-associated parameter, means the numerical value of the nasal polyp-associated parameter for a patient prior to or at the time of administration of a pharmaceutical composition of the present invention.

To determine whether a nasal polyp-associated parameter has "improved," the parameter is quantified at baseline and at a time point after administration of the pharmaceutical composition of the present invention. For example, a nasal polyp-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with a pharmaceutical composition of the present invention. In some embodiments, the parameter is measured daily (e.g., once or twice per day), weekly, biweekly, or monthly. In other embodiments, the parameter is measured daily and the mean value determined over the course of a month is compared to baseline.

The difference between the value of the parameter at a particular time point following initiation of treatment and the value of the parameter at baseline is used to establish whether there has been an "improvement" in the nasal associated parameter (e.g., an increase or decrease, as the case may be, depending on the specific parameter being measured).

Interleukin-4 Receptor Antagonists

In one embodiment, a subject in need thereof is administered a therapeutic composition comprising an interleukin-4 receptor (IL-4R) antagonist. As used herein, an "IL-4R antagonist" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, peptide-based IL-4R antagonists (e.g., "peptibody" molecules), and antibodies or antigen-binding fragments of antibodies that specifically bind human IL-4R.

The term "human IL-4R" (hIL-4R), as used herein, is intended to refer to the IL-4Rα subunit, which is a component of the IL-4 receptors Type I and Type II, as well as the IL-13 receptor system. An IL-4R antagonist, such as an anti-IL-4Rα antibody or antigen-binding fragment thereof, blocks the function of both IL-4 and IL-13 signal transduction.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain (CO). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some embodiments, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an anti-IL-4R antibody using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies featured in the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R, as used herein, includes antibodies that bind IL-4R or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods featured herein may include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as “germline mutations”). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-IL-4R antibodies comprising variants of any of the HCVR, LCVR, and/or CDR amino acid sequences disclosed herein having one or more conservative substitutions. For example, the present invention includes the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term “surface plasmon resonance”, as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term “$K_D$”, as used herein, is intended to refer to the equilibrium dissociation constant of a particular antibody-antigen interaction.

The term “epitope” refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. Nos. 7,608,693 and 7,605,237. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8. In yet other embodiments, the anti-IL-4R antibody or antigen-binding fragment thereof comprises an HCVR comprising SEQ ID NO:1 and an LCVR comprising SEQ ID NO:2. According to certain exemplary embodiments, the methods of the present invention comprise the use of the anti-IL-4Rα antibody referred to and known in the art as dupilumab, or a bioequivalent thereof.

The term “bioequivalent” as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an IL-4R antagonist are bioequivalent if they are pharmaceutically equivalent, meaning they contain the same amount of active ingredient (e.g., IL-4R antagonist), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration ($C_{max}$) and area under the plasma drug concentration time curve (AUC).

Other anti-IL-4Rα antibodies that can be used in the context of the methods of the present invention include, e.g., the antibody referred to and known in the art as AMG317 (Corren et al., 2010, *Am J Respir Crit Care Med.,* 181(8): 788-796), or any of the anti-IL-4Rα antibodies as set forth in U.S. Pat. No. 7,186,809, or U.S. Pat. No. 8,092,804.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which include administering an IL-4R antagonist to a patient, where the IL-4R antagonist is contained within a pharmaceutical composition. The pharmaceutical compositions featured in the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, symptoms, conditions, route of administration, and the like. The preferred dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer a pharmaceutical composition containing an IL-4R antagonist, including encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition can be delivered subcutaneously or intravenously with a standard needle and syringe. In addition, with respect to subcutaneous delivery, a pen delivery device readily has applications in delivering a pharmaceutical composition. Such a pen delivery device, including an autoinjection pen delivery device, can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition include, but are not limited to the SOLOSTAR™ pen (sanofi-aventis), the FLEXPEN™ (Novo Nordisk), and the KW IKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park IL), to name only a few.

For direct administration to the sinuses, the pharmaceutical compositions containing IL-4R antagonists may be administered using, e.g., a microcatheter (e.g., an endoscope and microcatheter), an aerosolizer, a powder dispenser, a nebulizer or an inhaler.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of IL-4R antagonist (e.g., anti-IL-4R antibody, or antigen binding fragment thereof) administered to a subject according to the methods featured herein is generally a therapeutically effective amount. As used herein, the phrase "therapeutically effective amount" means a dose of IL-4R antagonist that results in a detectable improvement in one or more symptoms associated with nasal polyps, or a dose of IL-4R antagonist that inhibits, prevents, lessens, or delays the progression of nasal polyps or a condition associated with nasal polyps. In the case of an anti-IL-4R antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody or antigen binding fragment.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

Combination Therapies

The methods, according to certain embodiments, include administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-4R antagonist. Administration "concurrent" with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an IL-13 antagonist, a TNF antagonist, an IL-8 antagonist, an IL-9 antagonist, an IL-17 antagonist, an IL-5 antagonist, an IgE antagonist, a CD48 antagonist, an antibiotic (e.g., doxycycline), an anti-fungal agent, a leukotriene, an antihistamine, an α-adrenergic decongestant, a mucolytic, an NSAID, a long-acting $beta_2$ agonist (e.g., salmeterol or formoterol), a short-acting $beta_2$ agonist, a steroid (e.g., an oral steroid), a corticosteroid, such as an intranasal corticosteroid (e.g., mometasone furoate (MFNS; e.g., Nasonex®)), or an inhaled corticosteroid (e.g., fluticasone or budesonide), an allergen immunotherapy, or combinations thereof. For example, in certain embodiments, the pharmaceutical composition comprising an IL-4R antagonist is administered in combination with a combination comprising a long-acting $beta_2$ agonist and an inhaled corticosteroid (e.g., fluticasone+salmeterol [e.g., Advair® (GlaxoSmithKline)]; or budesonide+formoterol [e.g., Symbicort® (Astra Zeneca)]).

In some embodiments, the IL-4R antagonist is administered after a subject receives surgery to treat nasal polyposis.

Administration Regimens

According to certain embodiments, multiple doses of an IL-4R antagonist may be administered to a subject over a defined time course. The methods include, for example, sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks or months). The present invention includes methods which comprise sequentially administering to the patient a single initial dose of an IL-4R antagonist, followed by one or more secondary doses of the IL-4R antagonist, and optionally followed by one or more tertiary doses of the IL-4R antagonist.

The terms "initial dose," "secondary doses," and "tertiary doses," refer to the temporal sequence of administration of the IL-4R antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-4R antagonist, but will generally differ from one another in terms of frequency of administration. In certain embodiments, however, the amount of IL-4R antagonist contained in the initial, secondary and/or tertiary doses will vary from one another (e.g., adjusted up or down as appropriate) during the course of treatment.

In one exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-4R antagonist which is administered to a patient prior to the administration of the very next dose in the sequence with no intervening doses.

These methods may include administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In certain embodiments, the initial dose (e.g., a "loading dose") is higher than either or both of the secondary and tertiary doses. For example, the initial dose can be a loading dose, which is 1.5×, 2×, 2.5×, 3× or more greater than the secondary dose.

Treatment Populations

The methods featured in the present invention including administering to a subject in need thereof a therapeutic composition comprising an IL-4R antagonist. As used herein, the expression "a subject in need thereof" means a human or non-human animal that exhibits one or more symptoms or indication of nasal polyposis, or who has been diagnosed with nasal polyposis, or chronic symptoms of sinusitis. For example, a subject in need thereof has bilateral nasal polyps, and a nasal polyp score of at least 5 out of a maximum of 8 for both nostrils, with at least a score of 2 for each nostril. In certain embodiments, the polyps are in the middle meatus. In certain embodiments, the presence of nasal polyps is confirmed by endoscopy. In some embodiments, the subject also has bilateral mucosal disease, which is confirmed by a method such as CT scan. As used herein "bilateral mucosal disease" is an infection of the mucous lining of the sinus cavities, e.g., the maxillary sinus cavities. In some embodiments, nasal polyposis (e.g., a nasal polyp score of at least 5 out of a maximum of 8 for both nostrils, with at least a score of 2 for each nostril) persists even after a treatment regimen of inhaled corticosteroids (INCS), such as where the INCS was administered for at least 6 weeks, at least 7 weeks, at least 8 weeks, or longer.

In certain embodiments, a subject in need thereof has anterior and/or posterior mucopurulent drainage, nasal obstruction, and a decreased sense of smell. In certain embodiments, a subject in need thereof has had symptoms of nasal polyposis for 6 weeks, 7 weeks, 8 weeks, 9 weeks, 10 weeks, 11 weeks, 12 weeks or more. In yet other embodiments, the subject has received a previous treatment, such as with an intranasal corticosteroid (e.g., MFNS), for at least 4 weeks, at least 5 weeks, at least 6 weeks, at least 7 weeks, at least 8 weeks, at least 9 weeks, at least 10 weeks or longer, prior to receiving treatment with an IL-4R antagonist. In some embodiments the subject will continue to receive the INCS while receiving treatment with the IL-4R antagonist. In other embodiments, the subject stops receiving the INCS before receiving treatment with the IL-4R antagonist, or the subject stops receiving treatment with the INCS if administration with the IL-4R antagonist is effective to treat the nasal polyposis. In some embodiments, the subject tapers the dose of the INCS before stopping treatment completely.

A subject in need thereof may further have been diagnosed with nasal polyposis on the basis of one or more of the following: (a) 22-item SinoNasal Outcome Test (SNOT-22) score; (b) subject-assessed nasal congestion/obstruction, anterior rhinorrhea, posterior rhinorrhea and loss of sense of smell; (c) number of nocturnal awakenings; (d) Visual Analog Score (VAS) to assess patient-rated rhinosinusitis symptom severity; (e) five-item Asthma Control Questionnaire (ACQS) score in patients with asthma; (f) Nasal Peak Inspiratory Flow (NPIF); (g) smell test (University of Pennsylvania Smell Identification Test (UPSIT); (h) physiological parameters, such as measured by nasal endoscopy and CT scan; (i) Lund-Mackay Score; and (k) Three Dimensional volumetric measurement of the maxillary sinus.

For example, in certain embodiments, a "subject in need thereof" is a human patient with chronic symptoms of sinusitis, which are the presence of at least two of the following symptoms: nasal blockade/obstruction/congestion or nasal discharge (anterior/posterior nasal drip); facial pain/pressure; and reduction or loss of smell.

In certain embodiments, a "subject in need thereof" is a human patient with a SNOT-22 score of greater than about 7, greater than about 10, greater than about 15, greater than about 20, greater than about 25, greater than about 30, greater than about 35, greater than about 40, greater than about 45, or greater than about 50. A "subject in need thereof" may also be a human patient who exhibits a Lund-Mackay score of greater than about 4, greater than about 5, greater than about 6, greater than about 7, greater than about 8, greater than about 9, greater than about 10, greater than about 11, greater than about 12, or greater than about 13.

In a related embodiment, a "subject in need thereof" may be a subject who, prior to receiving an IL-4R antagonist, has been prescribed or is currently taking another medication, "a background therapy." The background therapy can be, for example, an intranasal corticosteroid (INCS, or ICS), such as Mometasone furoate nasal spray (MFNS; Nasonex®). In some embodiments, a "subject in need thereof" is an asthma patient who prior to receiving an IL-4R antagonist, has been prescribed or is currently taking an INCS in combination with a long-acting beta$_2$-adronergic antagonist (LABA). Examples of INCS/LABA therapies include fluticasone/salmeterol combination therapy and budesonide/formoterol combination therapy. In some embodiments, the background therapy is a nasal saline, a topical decongestant, a topical anesthetic, a leukotriene antagonist or a systemic antihistamine. In some embodiments, the "subject in need thereof" continues the background therapy after the subject receives the IL-4R antagonist, and in other embodiments, the subject in need thereof stops receiving the background therapy (e.g., at once or gradually) before receiving the IL-4R antagonist.

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Clinical Trial of Subcutaneously Administered Anti-IL-4R Antibody (mAb1) in Patients with Persistent Moderate-to-Severe Eosinophilic Asthma, Including Asthma Patients with Chronic Hyperplastic Eosinophilic Sinusitis

A. Study Objectives and Overview

A randomized, placebo-controlled, double-blind, parallel group study was conducted with once-a-week subcutaneous administration of either 300 mg dupilumab ("mAb1") or placebo for 12 weeks to patients with persistent moderate-to-severe eosinophilic asthma who were partially controlled/uncontrolled by inhaled corticosteroid (ICS) and long-acting beta2 agonist (LABA) therapy. Dupilumab is an anti-IL-4R antibody having a heavy chain variable region of SEQ ID NO:1, and a light chain variable region of SEQ ID NO:2. Dupilumab is described in U.S. Pat. No. 7,608,693.

The primary objective of the study was to investigate the effects of mAb1 administered subcutaneously once weekly for 12 weeks as compared to placebo on reducing the incidence of asthma exacerbations in patients with persistent moderate-to-severe eosinophilic asthma. The secondary objectives of the study were to assess the safety and tolerability of mAb1 administered subcutaneously once weekly for 12 weeks in patients with persistent moderate to severe eosinophilic asthma, and to assess mAb1 serum concentrations following once weekly subcutaneous dosing for 12 weeks in patients with persistent moderate to severe eosinophilic asthma.

Prior to screening, patients were required to be on a stable dose of any of the following doses and formulations of ICS/LABA combination therapy (also called "background therapy") for at least 1 month:

Fluticasone/salmeterol combination therapy

Advair® Diskus—dry powder inhaler (DPI): 250/50 ug BID or 500/50 ug BID; or

Advair® HFA—metered dose inhaler (MDI): 230/42 ug BID or 460/42 ug BID; or

Budesonide/formoterol combination therapy (Symbicort® 160/9 ug BID or 320/9 ug BID); or Mometasone/formoterol combination therapy (Dulera® 200/10 ug BID or 400/10 ug BID)

Patients who were on budesonide/formoterol or mometasone/formoterol were switched to an equivalent dose of fluticasone/salmeterol at randomization (Day 1) and patients who had been on fluticasone/salmeterol remained on the same as background therapy.

Patients who satisfied the inclusion and exclusion criteria (see below) were randomized to one of the following treatments: 300 mg of mAb1 administered subcutaneously once weekly for 12 weeks; or placebo administered subcutaneously once weekly for 12 weeks.

The study comprised a 2-week screening period, a 12-week treatment period comprising a 4-week background therapy stable phase and an 8-week background therapy withdrawal phase post-randomization, followed by an 8-week post-treatment follow-up period.

Algorithm for Background Therapy (ICS/LABA) Withdrawal:

Patients remained on BID fluticasone/salmeterol background therapy for 4 weeks after starting add-on therapy or treatment of 300 mg mAb1 (or placebo). At 4 weeks post-randomization, patients were switched from the BID fluticasone/salmeterol combination therapy to an equivalent ICS dose of fluticasone monotherapy (comprising either Flovent® Diskus—DPI formulation of 250 ug or 500 ug BID; or Flovent® HFA—MDI formulation of 220 ug or 440 ug BID). The LABA component (i.e., salmeterol) was discontinued. At subsequent visits, beginning with week 6, the fluticasone dose was reduced by approximately 50%, provided the patient did not meet any of the criteria for an asthma exacerbation (as defined below). If no asthma exacerbations occurred, the ICS withdrawal proceeded according to the following dosing schedule:

| Background therapy | Background therapy withdrawal phase | | | | |
|---|---|---|---|---|---|
| stable phase | Week 4 | Week 6 | Week 7 | Week 8 | Week 9 |
| Fluticasone/salmeterol (DPI): 250/50 μg BID | Fluticasone (DPI): 250 μg BID | 100 μg BID | 50 μg BID | 0 μg BID | 0 μg BID |
| Fluticasone/salmeterol (DPI): 500/50 μg BID | Fluticasone (DPI): 500 μg BID | 250 μg BID | 100 μg BID | 50 μg BID | 0 μg BID |
| Fluticasone/salmeterol (MDI): 230/42 μg BID | Fluticasone (MDI): 220 μg BID | 110 μg BID | 44 μg BID | 0 μg BID | 0 μg BID |
| Fluticasone/salmeterol (MDI): 460/42 μg BID | Fluticasone (MDI): 440 μg BID | 220 μg BID | 110 μg BID | 44 μg BID | 0 μg BID |

Upon completing 12 weeks of treatment with investigational product (or after early discontinuation), patients were placed on their original dose of fluticasone/salmeterol, budesonide/formoterol, or mometasone/formoterol (dose at study entry) and albuterol or levalbuterol as-needed to control their symptoms for an additional 8 weeks off study medication before a final safety evaluation.

A schematic of the study protocol is provided in FIG. 1.

Adult patients were included in the study based on the following criteria: (1) physician's diagnosis of persistent asthma for at least 12 months based on the Global Initiative for Asthma (GINA) 2009 Guidelines, whose airway inflammation is likely to be eosinophilic; and (2) whose asthma is partially controlled or uncontrolled in inhaled corticosteroids/long acting beta-agonists combination therapy according to the following criteria: (i) stable dose of either fluticasone/salmeterol combination therapy (DPI formulation: 250/50 μg BID or 500/50 μg BID or MDI formulation: 230/42 μg BID or 460/42 μg BID), or budesonide/formoterol combination therapy (160/9 μg BID or 320/9 μg BID), or mometasone/formoterol combination therapy (200/10 μg BID or 400/10 μg BID) for at least 1 month prior to screening; (ii) blood eosinophils ≥300 cells/pi or sputum eosinophils ≥3% during the screening phase; (iii) Juniper asthma control questionnaire (5-question version, ACQ) score of ≥1.5 and ≤3.0 at screening; (iv) FEV1 ≥50% predicted normal during the screening phase (3 attempts maximum) and on the randomization day prior to the first dose (3 attempts maximum); (v) has had within the 2 years prior to screening either treatment with one or more systemic (oral and/or parenteral) steroid bursts for worsening asthma or in-patient hospitalization or an emergency care visit for worsening asthma; and (vi) documented history of reversibility within 12 months of screening that meets the criterion—at least 12% and 200 mL in FEV1 after 200 μg to 400 μg (2 to 4 inhalations) of albuterol during the screening phase (3 attempts maximum), or documented history of a positive methacholine challenge (PD20 methacholine ≤8 mg) within 12 months prior to screening. Patients with moderate-to-severe asthma that is partially controlled or uncontrolled with moderate to high doses of combination therapy with inhaled corticosteroids and long-acting beta agonists (ADVAIR®, SYMBICORT® or DULERA®) and with blood eosinophils greater than or equal to 300 cells per microliter, or sputum eosinophils greater than or equal to 3% during the screening phase, were included in the study.

Patients who met all the inclusion criteria were screened for the following exclusion criteria: (1) patients less than 18 years of age or greater than 65 years of age; (2) clinically relevant abnormal laboratory values suggesting an unknown disease and requiring further evaluation; (3) chronic obstructive pulmonary disease (COPD) and/or other lung diseases impairing pulmonary function tests; (4) patients requiring beta-adrenergic receptor blockers for any reason; (5) current smoker or cessation of smoking within the 6 months prior to screening; (6) previous smoking with a smoking history >10 cigarette pack-years; (7) in-patient hospitalization or emergency care visit due to asthma exacerbation in the 2 months prior to screening; (8) plans to begin allergen immunotherapy within the study period; (9) exposure to another investigative antibody within a time period prior to screening that is less than 5 half-lives of the antibody but not less than 30 days, or if the half life of the antibody is not known, then a time period prior to screening that is at least 6 months; (10) previous enrollment into the current study; (11) patient was the investigator, his/her family member or an employee at the investigational site; (12) known or suspected non-compliance, alcohol or drug abuse; (13) inability to follow the procedures of the study (e.g., due to language problems or psychological disorders); (14) reversal of sleep pattern (e.g., night shift worker); (15) treatment with drugs known to prolong QTc interval; (16) concomitant severe disease(s) for which the use of ICS (e.g., active or inactive pulmonary tuberculosis) or LABA (e.g., diabetes, cardiovascular diseases, hypertension, hyperthyroidism, thyrotoxicosis, etc) are contra-indicated; (17) use of injectable glucocorticosteroids or oral systemic glucocorticosteroids within 2 months prior to screening or more than 3 courses within the 6 months prior to screening; (18) pre-treatment with variable doses of ICS, either alone or in combination with a non-steroidal controller (other than fluticasone/salmeterol combination therapy, budesonide/formoterol combination therapy, or mometasone/formoterol combination therapy); (19) patients receiving prohibited concomitant medications (listed below); (20) known allergy to doxycycline or related compounds; (21) pregnancy or intention to become pregnant during the course of the study, breast feeding or unwillingness to use an effective method of contraception; and (22) recent history of a parasitic infection or travel to a parasitic endemic area within 6 months prior to screening.

Patients remained on a constant dose of the background asthma therapy for the first four weeks of the study after which the dose of background therapy was reduced gradually. First, the long-acting beta agonist component of the background therapy was withdrawn at week 4, and then the inhaled corticosteroid dose was reduced by half every 2 weeks until week 12. Patients continued on study treatment until the end of the study or until they were withdrawn due to an asthma exacerbation or for any other reason.

B. Study Treatments

Investigational Product: Sterile mAb1 150 mg/mL solution for SC injection was provided in a 5 mL glass vial. Each vial contained a withdrawable volume of 2 mL. A 300 mg dose was administered subcutaneously at the study site once weekly in the morning for 12 weeks. Placebo: Sterile placebo for SC injection was provided in an identically matched 5 mL glass vial. Each vial contained a withdrawable volume of 2 mL. Placebo was administered subcutaneously at the study site once weekly in the morning for 12 weeks.

The following concomitant medications were not allowed during the duration of the study: any other inhaled steroid other than fluticasone/salmeterol combination therapy or fluticasone administered per the protocol (or budesonide/formoterol or mometasone/formoterol during the screening period); systemic or ocular steroids; LABAs other than the salmeterol component of the fluticasone/salmeterol combination therapy administered per the protocol; any other ICS/LABA combination products other than those given above; any inhaled anti-cholinergic agents (e.g., Ipratropium bromide or tiotropium); methylxanthines (theophylline, aminophyllines); cromones; anti-IgE therapy; lipoxygenase inhibitors; and leukotriene receptor antagonists or leukotriene synthesis inhibitors.

C. Efficacy of Treatment

The primary endpoint of this study was the occurrence of an exacerbation of asthma as defined by any of the following: (1) a 30% or greater reduction from baseline in morning peak expiratory flow (PEF) on two consecutive days; or (2) six or more additional reliever puffs of albuterol or levalbuterol in a 24 hour period (compared to baseline) on 2 consecutive days; or (3) deterioration of asthma, as determined by the Investigator, requiring: (a) systemic (oral and/or parenteral) steroid treatment, or (b) an increase in ICS times the last dose received prior to discontinuation from the study, or (c) hospitalization.

Secondary endpoints of the study included mean changes from baseline of the following parameters: (1) Forced expiratory volume in 1 second (FEV1) in liters measured at every visit; (2) Morning and evening peak expiratory flow rate (AM PEF and PM PEF) in liters/minute measured daily; (3) Daily Albuterol/Levalbuterol use in inhalations/day; (4) Five-item Asthma Control Questionnaire (ACQS) score at every visit; and (5) Nighttime awakenings (no. of times per night) measured daily and (6) a 22-item Sino-Nasal Outcome Test (SNOT-22), evaluated at baseline and end of treatment (at Week 12), to assess upper airway symptoms. Secondary endpoints also included proportion of patients with a composite asthma event defined by a 30% or greater reduction from baseline in morning PEF on two consecutive days together with ≥6 additional reliever puffs of albuterol or levalbuterol in a 24-hour period 9 compared to baseline) on 2 consecutive days. PEF, ACQ5, asthma symptoms scores, nocturnal awakenings, and reliever medication use were captured in an electronic daily diary. Mean daily nocturnal awakenings, ranging from 0-10, were averaged from the previous 7 days. Morning and evening asthma symptom scores consisted of a non-validated patient-reported outcome assessed on a 5-point Likert-type scale, with higher scores indicating worse outcomes (Table 2). Patients recorded overall symptom scores twice a day prior to measuring PEF. Data were described as the average for the 7 days prior to the specified time point.

TABLE 2

| Asthma Symptom Score Assessment |
|---|
| A) Morning symptom score: |
| 0 = No asthma symptoms, slept through the night |
| 1 = Slept well, but some complaints in the morning. No nighttime awakenings |
| 2 = Woke up once because of asthma (including early awakening) |
| 3 = Woke up several times because of asthma (including early awakening) |
| 4 = Bad night, awake most of the night because of asthma |
| B) Evening symptom score: |
| 0 = Very well, no asthma symptoms |
| 1 = One episode of wheezing, cough, or breathlessness |
| 2 = More than one episode of wheezing, cough, or breathlessness without interference of normal activities |
| 3 = Wheezing, cough, or breathlessness most of the day, which interfered to some extent with normal activities |
| 4 = Asthma very bad. Unable to carry out daily activities as usual |

D. Adverse Events Monitoring

Safety was assessed throughout the study by monitoring Adverse Events and Serious Adverse Events.

An Adverse Event (AE) is any untoward medical occurrence in a subject or clinical investigation subject administered a pharmaceutical product. An AE can, therefore, be any unfavorable and unintended sign (including abnormal laboratory finding), symptom, or disease temporally associated with the use of a medicinal product, whether or not considered related to the medicinal (investigational) product. AEs also include: any worsening (i.e., any clinically significant change in frequency and/or intensity) of a pre-existing condition that is temporally associated with the use of the study drug; abnormal laboratory findings considered by the Investigator to be clinically significant; and any untoward medical occurrence.

A Serious Adverse Event (SAE) is any untoward medical occurrence that at any dose results in death; is life-threatening; requires in-patient hospitalization or prolongation of existing hospitalization; results in persistent or significant disability/incapacity; is a congenital anomaly/birth defect; or is an important medical event.

E. Statistical Methods

For the primary analysis of proportion of patients experiencing an asthma exacerbation, a logistic regression model was used to compare SAR group with placebo. The model included terms for treatment and stratification factor (prior ICS/LABA combination therapy dose). The primary analysis was performed based on modified intent-to-treat (mITT) population which included all randomized patients who received at least one dose of mAb1. A stratified chi-square test was also used to corroborate the primary analysis.

For secondary efficacy endpoints except SNOT-22, the change from baseline was analyzed using a mixed-effect model with repeated measures (MMRM) approach. The model included change from baseline values up to week 12 as response variables, and factors (fixed effects) for treatment, stratification factor, visit, treatment-by-visit interaction, baseline value, and baseline-by-visit interaction. Statistical inferences on treatment comparisons for the change from baseline at week 12 were derived from the mixed-effect model. Change from baseline in SNOT-22 was analyzed using an analysis of covariance (ANCOVA), with end of treatment measurements used to impute missing data. Phar macodynamic effects were evaluated using MMRM models in a post hoc fashion. No adjustments were made for multiplicity, since there was only one primary endpoint and analysis. Safety variables including AEs, laboratory parameter, vital signs, ECG, clinical laboratory observations and physical examinations were summarized using descriptive statistics.

(Table 3). As noted above, patients were treated either with 300 mg subcutaneous mAb1 once a week, or with placebo. The study treatment period was completed by 86.5% and 67.3% of the mAb1 and placebo patients, respectively. The most common cause of discontinuation was lack of efficacy, which was more frequent with placebo (21.2%) than mAb1 (1.9%).

TABLE 3

Baseline Demographic and Clinical Characteristics of Treatment Groups.*

| Variable | Placebo (N = 52) | mAb1 300 mg (N = 52) |
|---|---|---|
| Age (yr) | 41.6 ± 13.1 | 37.8 ± 13.2 |
| Male sex, no. (%) | 26 (50.0) | 26 (50.0) |
| Race or ethnic group, no. (%) | | |
| White | 38 (73.1) | 45 (86.5) |
| Black or African American | 9 (17.3) | 5 (9.6) |
| Asian | 3 (5.8) | 1 (1.9) |
| Other | 2 (3.8) | 1 (1.9) |
| Body mass index | | |
| Mean (kg/m$^2$) | 31.6 ± 7.0 | 31.3 ± 8.0 |
| ≥30, no. (%) | 25 (48.1) | 24 (46.2) |
| Duration of asthma (yr) | 26.9 ± 14.8 | 24.2 ± 12.6 |
| Number of asthma exacerbations in prior 2 years | 1.4 ± 1.3 | 1.4 ± 1.0 |
| Prior ICS/LABA combination therapy dose, no. (%) | | |
| High Dose | 41 (78.8) | 42 (80.8) |
| Low Dose | 11 (21.2) | 10 (19.2) |
| Blood eosinophils (×10$^{-9}$/l) | 0.47 ± 0.21 | 0.55 ± 0.19 |
| FEV$_1$ (I) | 2.54 ± 0.66 | 2.47 ± 0.65 |
| FEV$_1$ (% of predicted value) | 72.0 ± 12.7 | 72.0 ± 12.6 |
| PEF (l/min) | | |
| Morning | 406.9 ± 110.7 | 393.0 ± 101.1 |
| Evening | 416.6 ± 116.8 | 414.6 ± 102.3 |
| ACQ5 score | 2.1 ± 0.5 | 2.1 ± 0.5 |
| Asthma symptom score | | |
| Morning | 0.73 ± 0.63 | 0.75 ± 0.81 |
| Evening | 1.12 ± 0.73 | 0.92 ± 0.71 |
| Nocturnal awakenings per day | 0.21 ± 0.50 | 0.44 ± 0.80 |
| SNOT-22 | 26.2 ± 15.6 | 30.9 ± 14.8 |
| Inhalations of albuterol or levalbuterol/24-hour period | 2.0 ± 1.8 | 2.2 ± 2.4 |
| FeNO (ppb) | 35.0 ± 27.1 | 37.6 ± 28.1 |
| TARC (pg/ml) | 470.5 ± 204.7 | 496.1 ± 342.4 |
| Eotaxin-3 (pg/ml) | 117.3 ± 349.2 | 75.4 ± 44.0 |
| IgE (IU/ml) | 694.7 ± 1837.8 | 657.7 ± 1482.3 |

*Plus-minus values are means ± SD, except as otherwise noted. ACQ5 denotes the Asthma Control Questionnaire (5 question version), FeNO fraction of exhaled nitric oxide, FEV$_1$ forced expiratory volume in 1 second, IgE immunoglobulin E, PEF peak expiratory volume, SNOT-22 the 22-item Sinonasal Outcome Test, and TARC thymus and activation regulated chemokine.

Demographic and clinical characteristics were summarized using descriptive characteristics. Plots of secondary and pharmacodynamic variables are presented as mean change from baseline over time with standard error. Comparison of treatment effects from the MMRM analyses are based on least square mean change (95% confidence intervals [CI]) from baseline at Week 12.

F. Results

The results observed with all 104 randomized patients (from 491 screened) who either completed or discontinued the treatment phase of the study are summarized below. All randomized patients were exposed to study treatment and included in the mITT population. Baseline characteristics were similar between groups. The demographic and clinical characteristics were also similar between the two groups (i) Primary Efficacy Endpoint The incidence of asthma exacerbations in the placebo and mAb1 treatment groups is presented in Table 4.

TABLE 4

Incidence of Asthma Exacerbations in mITT population

| | Placebo (N = 52) | mAb1 (N = 52) |
|---|---|---|
| Patients With No Asthma Exacerbations | 29 (55.8%) | 49 (94.2%) |
| Patients With Asthma Exacerbations | 23 (44.2%) | 3 (5.8%) |
| Odds Ratio vs Placebo (95% CI) | — | 0.077 (0.021, 0.279) |

There were a total of 26 asthma exacerbations during the treatment period, and no patients were hospitalized for asthma exacerbations. There were 23 patients (44.2%) who experienced an asthma exacerbation in the placebo group, whereas only 3 patients (5.8%) experienced an asthma exacerbation in the mAb1 treatment group. The odds ratio is 0.077 (p <0.0001) and the relative risk reduction is approximately 87%.

Out of the 26 asthma exacerbations experienced during this study, 9 were considered severe as demonstrated by a need for immediate intervention in the form of treatment with either systemic corticosteroids or with inhaled corticosteroids at 4 or more times the dose taken prior to the event. A summary of the incidence of severe asthma exacerbations is presented in Table 5.

TABLE 5

| Incidence of Severe Asthma Exacerbations in mITT population | | |
|---|---|---|
| | Placebo (N = 52) | mAb1 (N = 52) |
| Patients With No Asthma Exacerbations | 29 (55.8%) | 49 (94.2%) |
| Patients With Severe Asthma Exacerbations | 8 (15.4%) | 1 (1.9%) |
| Patients With Non-Severe Asthma Exacerbations | 15 (28.8%) | 2 (3.8%) |

As shown in Table 5, eight severe asthma exacerbations were observed in the placebo group, and only 1 severe asthma exacerbation was observed in the mAb1 treatment group. The remaining 15 asthma exacerbations in the placebo group and 2 in the mAb1 group met the protocol definition of exacerbation based on decreased morning PEF and/or increased albuterol/levalbuterol use. Within the active treatment group, a sustained improvement versus baseline was observed during the course of the study for all parameters, despite steroid withdrawal.

TABLE 6

| Exacerbation Events | | |
|---|---|---|
| Outcome | Placebo (N = 52) | mAb1 (N = 52) |
| ≥30% reduction from baseline in morning PEF in a 24-hr period on 2 consecutive days | 10* (19.2) | 1 (1.9) |
| ≥6 additional inhalations of albuterol/levalbuterol in a 24-hr period on 2 consecutive days | 10 (19.2) | 1 (1.9) |
| Systemic steroid treatment | 5 (9.6) | 1 (1.9) |
| ≥4-fold increase in ICS from the previous dose | 3 (5.8) | 0 |
| Hospitalization | 0 | 0 |

*4 Placebo patients met both PEF and systemic steroid treatment criteria, and 1 placebo patient met both PEF and additional albuterol/levalbuterol use.

With mAb1, the time to exacerbation was longer, and the risk of exacerbation was reduced relative to placebo (hazard ration 0.10; 95% CI 0.03, 0.34; P<0.001). An analysis of the time to asthma exacerbation by Kaplan-Meier Plot revealed that the effect of treatment with mAb1 is sustained over time, including after 8 weeks when patients are at higher risk of developing exacerbations due to steroid withdrawal.

Only 1 patient from the placebo group had a composite asthma event. A composite asthma event is defined as a 30% or greater reduction from baseline in morning PEF on 2 consecutive days together with 6 additional reliever puffs of albuterol or levalbuterol in a 24-hour period (compared to baseline) on 2 consecutive days.

(ii) Other Efficacy Endpoints

Lung function parameters (FEV1, AM PEF and PM PEF), asthma symptom-based endpoints (ACQ score, nighttime awakenings) and albuterol use were assessed for each patient at each visit. In addition, the SNOT-22 score was assessed at baseline and at the end of treatment. For all parameters, the baseline and Week 12 (LOCF) mean values along with the mean difference between treatment groups (ANOVA model for SNOT-22) are summarized in Table 7. In Table 7, the column labeled “Difference vs. Placebo” reflects the placebo-corrected value from baseline which takes into account changes that are observed in the value of the parameter as compared to the changes that were observed for that parameter in the placebo-treated group.

TABLE 7

| Secondary Parameters of Lung Function and Symptom Scores | | | | | |
|---|---|---|---|---|---|
| | N | Baseline Mean (SD) | Least-Squared Mean Change (SD) | Difference vs. Placebo | p value |
| FEV1 (L) | | | | | |
| Placebo | 52 | 2.54 (0.66) | −0.22 (0.06) | — | |
| mAb1 | 52 | 2.47 (0.65) | 0.05 (0.06) | 0.27 (0.11, 0.42) | 0.0009 |
| AM PEF (L/min) | | | | | |
| Placebo | 52 | 406.9 (110.7) | −20.7 (9.1) | — | |
| mAb1 | 51 | 393.0 (101.1) | 13.9 (8.8)† | 34.6 (10.6, 58.5) | 0.0051 |
| PM PEF (L/min) | | | | | |
| Placebo | 51 | 416.6 (116.8) | −18.4 (8.9)† | — | |
| mAb1 | 52 | 414.6 (102.3) | 4.3 (8.5) | 22.7 (−0.7, 46.0) | 0.0567 |
| Albuterol Use (Puffs/Day) | | | | | |
| Placebo | 52 | 2.0 (1.8) | 0.7 (0.3) | — | |
| mAb1 | 50 | 2.2 (2.4) | −1.3 (0.3)‡ | −2.0 (−2.9, −1.2) | <0.0001 |

TABLE 7-continued

Secondary Parameters of Lung Function and Symptom Scores

| | N | Baseline Mean (SD) | Least-Squared Mean Change (SD) | Difference vs. Placebo | p value |
|---|---|---|---|---|---|
| ACQ Score | | | | | |
| Placebo | 52 | 2.08 (0.52) | −0.27 (0.16) | — | |
| mAb1 | 52 | 2.09 (0.46) | −1.00 (0.16) | −0.73 (−1.15, −0.30) | 0.0011 |
| Night-time Awakenings (No. of times/night) | | | | | |
| Placebo | 52 | 0.2 (0.5) | 0.1 (0.1) | — | |
| mAb1 | 52 | 0.4 (0.8) | −0.2 (0.1) | −0.2 (−0.5, −0.0) | 0.0518 |
| SNOT22 Average Score | | | | | |
| Placebo | 51 | 26.24 (15.62) | 0.23 (2.15)† | — | |
| mAb1 | 50 | 30.92 (14.77) | −8.26 (2.20)‡ | −8.49 (−13.96, −3.03) | 0.0027 |

†51 patients with at least 1 post-baseline assessment.

‡50 patients with at least 1 post-baseline assessment.

Treatment with mAb1 resulted in a significant change from baseline in FEV1 at Week 1, which was maintained through Week 12 despite LABA and ICS withdrawal, with a small decrease in FEV1 at Week 5 coinciding with LABA withdrawal. Similar improvements were observed in morning PEF, but less so in evening PEF. The least-squared (LS) mean change from baseline to week 12 in FEV1 was −0.22 L for placebo and 0.05 L for the mAb1 group. (p=0.0009).

ACQ5 score improved in both treatment groups at Week 1. However, while ACQ5 improved further with mAb1 between Weeks 1 and 4, the placebo effect stabilized, maintaining the difference through Week 12.

Morning symptom scores increased from baseline to Week 12 with placebo. With mAb1, there was an initial decrease which remained below baseline through Week 12. A similar pattern (with greater variability) was observed for evening asthma symptom scores.

Nocturnal awakenings were stable from the placebo group through Week 6, then increased from Weeks 6 to 12. In contrast, nocturnal awakenings decreased in the mAb1 group by Week 1 and remained improved versus baseline through Week 12.

Changes in albuterol/levalbuterol use were similar to other secondary endpoints: an initial decrease followed by a return towards baseline with placebo. With mAb1, the initial decrease was maintained over time.

There was a non-significant difference at baseline between the SNOT-22 values with the mean placebo score at 26.24 and the mean mAb1 score at 39.02. At week 12, the LS mean change was a slight increase of 0.23 points for the placebo group and a mean decrease (improvement) of 8.26 points for the mAb1 group. This represented a magnitude of improvement of 8.49 points for the mAb1 group (p=0.0027).

TABLE 8

Secondary Endpoints

| Outcome | Placebo (N = 52) | mAb1 (N = 52) | Difference vs Placebo (95% CI)** | P Value |
|---|---|---|---|---|
| Kaplan-Meier estimate at 12 weeks | 46.0 (31.8, 60.2) | 5.8 (0.0, 2.1) | 0.10 (0.03 to 0.34) | <0.001 |
| Change in morning asthma symptom scores, baseline to week 12 | 0.3 ± 0.1 | −0.4 ± 0.1 | −0.7 (−0.9 to −0.4) | <0.001 |
| Change in evening asthma symptom scores, baseline to week 12 | 0.1 ± 0.1 | −0.6 ± 0.1 | −0.7 (−0.9 to −0.4) | <0.001 |

TABLE 9

Change From Baseline at Week 12 in SNOT-22 Items Relevant to Upper Airway Disease.

| SNOT-22 Subscale | Least-Squares Mean Change ± Standard Error: Placebo (N = 52) | mAb1 (N = 52) | Difference vs Placebo (95% CI) | P Value |
|---|---|---|---|---|
| Need to blow nose | −0.25 ± 0.17* | 0.95 ± 0.17† | −0.70 (−1.13, −0.26) | 0.002 |
| Nasal blockage | −0.20 ± 0.19* | −0.94 ± 0.19† | 0.75 (−1.22, −0.28) | 0.002 |

TABLE 9-continued

Change From Baseline at Week 12 in SNOT-22 Items Relevant to Upper Airway Disease.

| SNOT-22 Subscale | Least-Squares Mean Change ± Standard Error Placebo (N = 52) | mAb1 (N = 52) | Difference vs Placebo (95% CI) | P Value |
|---|---|---|---|---|
| Decreased sense of smell/taste | 0.04 ± 0.18* | −1.13 ± 0.18† | −1.16 (−1.62, −0.71) | <0.001 |

*51 and †50 patients with at least 1 post-baseline assessment respectively

For all secondary endpoints, Week 12 measurements favored mAb1 treatment and were significant except for evening PEF and nocturnal awakenings (Table 7 and 8). Significant improvements with mAb1 were also observed for the three SNOT-22 items relevant to upper airway disease (Table 9)

(iii) Safety mAb1 was generally safe and well tolerated. Treatment-emergent adverse events (TEAEs) were reported similarly by 40 (76.9%) of placebo-treated patients and by 42 (80.8%) of mAb1-treated patients (Table 10). TEAEs were non-specific, generally mild to moderate in intensity and the majority recovered by the end of the study. An increased reporting of the following TEAEs was observed for mAb1 in comparison with placebo: injection site reactions were reported by 15 (28.8%) mAb1 patients and by 5 (9.6%) placebo patients; nasopharyngitis was reported by 7 (13.5%) mAb1 patients and 2 (3.8%) placebo patients; headache was reported by 6 (11.5%) mAb1 patients and 3 (5.85) placebo patients and nausea was reported by 4 (7.7%) mAb1 patients and 1 (1.9%) placebo patients.

TABLE 10

Adverse Events.

| Adverse event | Placebo (N = 52) no. of patients (%) | mAb1 300 mg (N = 52) |
|---|---|---|
| Any adverse event | 40 (76.9) | 42 (80.8) |
| Any serious adverse event | 3 (5.8) | 1 (1.9) |
| Study discontinuation owing to adverse event | 3 (5.8) | 3 (5.8) |
| Death | 0 | 0 |
| Most common AEs* | | |
| Injection site reactions† | 5 (9.6) | 15 (28.8) |
| Nasopharyngitis | 2 (3.8) | 7 (13.5) |
| Upper respiratory tract infection | 9 (17.3) | 7 (13.5) |
| Headache | 3 (5.8) | 6 (11.5) |
| Nausea | 1 (1.9) | 4 (7.7) |
| Arthropod bite | 0 | 3 (5.8) |
| Muscle spasms | 0 | 3 (5.8) |
| Nasal congestion | 1 (1.9) | 3 (5.8) |
| Rash | 1 (1.9) | 3 (5.8) |
| Urticaria | 0 | 3 (5.8) |
| Viral upper respiratory tract infection | 0 | 3 (5.8) |

*≥3 patients in any treatment group by Preferred Term

†Injection site reaction includes events reported as: injection site pain, injection site reaction, injection site erythema, injection site rash, injection site haematoma, injection site urticaria, injection site dermatitis, injection sites inflammation, injection site nodule, injection site pruritus and injection site swelling.

There were no deaths reported during the study period. Of the 4 treatment emergent serious adverse events (SAEs) reported: 1 mAb1 patient experienced bipolar disorder and 3 placebo patients experienced SAEs of asthma with pneumonia, gunshot wound with left pneumothorax, and right ankle fracture. None of these SAEs were considered as related to the mAb1 and all but the recent ankle fracture were recovered by the end of the study. There were no deaths.

A total of 6 patients discontinued the study due to a TEAE: 3 patients in the mAb1 group (bipolar disorder, asthma with wheezing, and angioedema) and 3 patients in the placebo group (upper respiratory tract infection, psoriasis and asthma). The TEAE of angioedema occurred in a 42-year old African-American female after the ninth study treatment dose as a pruritic, popular rash observed at, and distant to, the injection site. It persisted for one week, resolved after study treatment discontinuation, and prednisome and diphenhydramine treatment. It was deemed treatment-related. This AE was subsequent to milder rashes at the injection site after the first and sixth study treatment doses.

Among the most common AEs occurring in patients in any treatment group (Table 10), injection site reactions, nasopharyngitis, nausea, and headache occurred more frequently with mAb1 than placebo. No clinically significant changes in vital signs, physical examination, clinical laboratory or ECG findings were reported in either group.

G. Conclusion

Significant improvements were observed for lung function and other asthma control parameters. Efficacy was observed early and sustained despite background therapy withdrawal. A relative reduction of approximately 87% ($p<0.0001$) in the primary endpoint of the incidence of asthma exacerbations in persistent, moderate-to-severe asthma patients with eosinophilia was observed after 12-week treatment with 300 mg of mAb1 once weekly (5.8%) compared with placebo (44.2%). As shown in Table 7, clinically meaningful and statistically significant (without multiplicity adjustment) improvements with treatment compared with placebo were observed in lung function parameters (FEV1, PEF AM), asthma symptom scores (ACQ) and albuterol use. Positive trends were observed for PEF PM ($p=0.0567$) and nocturnal awakenings ($p=0.0518$). A statistically significant (without multiplicity adjustment) improvement was also observed for the SNOT-22 score. Within the active treatment group, a sustained improvement versus baseline was observed during the course of study for all parameters, despite LABA and ICS withdrawal. mAb1 was generally safe and well tolerated.

Example 2: Biomarker Studies

Biomarker analysis was conducted on samples taken from subjects who participated in clinical trials of mAb1 (see Example 1 above). In particular, serum/plasma biomarkers associated with TH2 inflammation such as thymus and activation chemokine (TARC; CCL17), Immunoglobulin E (IgE), eotaxin-3, periostin, carcinoembryonic antigen (CEA), YKL-40 and blood eosinophils were measured in samples from patients at baseline and at different time points following initiation of study treatment(s). Baseline levels of these biomarkers were assessed for potential predictive value for treatment response. In addition, the fraction of exhaled NO (FeNO) and induced sputum eosinophils and neutrophils were measured as biomarkers of bronchial inflammation. Exhaled nitric oxide assessment was conducted prior to spirometry and following a fast of at least 1 hour using a NIOX instrument (Aerocrine AB, Solna, Sweden). Biomarkers were analyzed using a mixed model and the least square mean derived from the model are reported below.

Asthma subjects (N=104) were administered either mAb1 (300 mg) or placebo subcutaneously, on days 1, 8, 15, 22, 29, 36, 43, 50, 57, 64, 71 and 78 of the study (i.e., 12 weekly doses) (see Example 1, above). Samples for biomarker analysis were collected from the antibody- and placebo-treated subjects at week 0, 1, 4, 8 and 12. Antigen-specific IgE was detected using the Phadiatop® test.

TARC, eotaxin-3 and IgE remained unchanged in response to placebo. In contrast, a rapid reduction in TARC (mean % change −22.7% vs +0.3%; p=0.0003) and eotaxin-3 (mean % change −39.62% vs 12.69%; p<0.0001) was observed within one week in patients treated with mAb1 and persisted until week 12: TARC: −26.0% vs +7.6% placebo (p=0.0005); Eotaxin-3: −45.67% vs +5.13% placebo (p<0.0001).

TARC levels responded within a week following exposure to mAb1 at 300 mg administered subcutaneously. TARC levels plateau at approximately 50% of the baseline level in mAb1-treated subjects, regardless of ICS withdrawal. The data suggest that TARC expression is more directly linked to IL-4R signaling, than FEV1 changes (which drop in parallel to ICS withdrawal [after Week 4]) and that IL-4R blockage induces a shift towards a TH1 signature, as observed with, for example, IFNgamma administration. It might be possible to titrate the mAb1 dose using TARC (and for example CXCL10) in particular in patients requiring long term treatment and at risk for TH1 type immune diseases.

Total serum IgE also decreased following mAb1 treatment. Total serum IgE response was more heterogeneous and delayed compared to TARC response. Mean (SD) baseline IgE levels were 694.68 IU/L (1837.82) for the placebo group (n=52) and 657.66 (1482.25) for the mAb1 group (n=52), whereas median was 169.95 for the placebo group and 206.15 for the mAb1 group. Despite this heterogeneity, a trend towards IgE decrease in mAb1-exposed patients compared with placebo was observed—however, starting at week 4 only. Serum IgE was significantly reduced in the mAb1 group compared with placebo (mean % change, −10.1% vs +13.5%; p=0.0325) starting from week 4 and continued to decrease until week 12 (mean % change, −36.8% for mAb1 vs −5.5% for placebo; p<0.0001).

Changes from baseline and placebo at Week 12 for FeNO, TARC, eotaxin-3, and IgE all favored mAb1 (all P<0.001) (Table 11). No differences from baseline or between treatments were observed in YKL-40 or CEA.

TABLE 11

Percent Change From Baseline at Week 12 in Pharmacodynamic Endpoints.

| | Least-Squares Mean Percent Change ± Standard Error | | |
|---|---|---|---|
| Outcome | Placebo (N = 52) | mAb1 (N = 52) | P Value |
| FeNO | 35.0 ± 10.8 | 28.7 ± 11.2 | <0.001 |
| TARC | 7.6 ± 6.9 | −26.0 ± 6.9 | <0.001 |
| Eotaxin-3 | 5.1 ± 4.7 | −45.7 ± 4.7 | <0.001 |
| IgE | 5.5 ± 3.6 | −36.8 ± 3.6 | <0.001 |
| Blood eosinophils | 2.7 ± 15.8 | 41.6 ± 15.7 | 0.078 |

There was a transient decrease in periostin levels, followed by an increase with LABA/ICS withdrawal. Administration of mAb1 delayed the increase, but did not prevent the increase above baseline. No consistent treatment effect was observed with CEA and YKL-40. The number of blood eosinophils remained unchanged through Week 6, but then increased at Weeks 8 and 12. Peripheral blood eosinophil numbers were unchanged on placebo throughout treatment. The difference between the treatments was not significant, with the borderline increase driven by larger blood eosinophil elevations in only a few patients treated with mAb1. Little or no increases were observed in the majority of patients.

TABLE 12

Proportions of Patients Achieving Thresholds of Change in Blood Eosinophil Levels.

| | Number (%) of patients | |
|---|---|---|
| Change in eosinophils | Placebo (n = 52) | mAb1 (n = 52) |
| >15% Decrease | 13 (30.2) | 21 (47.7) |
| 15% Decrease-0% change | 7 (16.3) | 6 (13.6) |
| 0%-15% Increase | 8 (18.6) | 4 (9.1) |
| 15%-100% Increase | 13 (30.2) | 6 (13.6) |
| 100%-200% increase | 2 (4.7) | 3 (6.8) |
| >200% increase | 0 | 4 (9.1) |

Since only 3 mAb1 patients experienced asthma exacerbation during the study, no conclusion could be drawn regarding the association between baseline biomarker levels and asthma exacerbations.

mAb1 treatment was also associated with a significant decrease from baseline in FeNO at Week 4, and FeNo remained below baseline through Week 12, regardless of ICS withdrawal (mean % change at week 12: −28.7 for mAb1 vs 35.0 for placebo; p<0.0001). In contrast, placebo FeNo values remained stable through Week 8, followed by an increase at Week 12 coincident with ICS withdrawal.

Forced expiratory volume in 1 second ($FEV_1$) improvement significantly correlated with FeNO reduction (r=−0.408, p=0.009) at week 12. Similarly, improvements in AM-PEF and PM-PEF correlated with FeNO reduction. Other correlations with FeNO were not significant. See Table 13.

TABLE 13

Correlation between $FEV_1$ and PD Endpoints.

| Outcome | Correlation | P Value |
|---|---|---|
| FeNO | −0.408 | <0.009 |
| TARC | −0.248 | 0.10 |

TABLE 13-continued

| Correlation between $FEV_1$ and PD Endpoints. | | |
|---|---|---|
| Outcome | Correlation | P Value |
| Eotaxin-3 | −0.146 | 0.34 |
| IgE | −0.279 | 0.06 |
| Blood eosinophils | 0.165 | 0.28 |

Scatter plot analysis of baseline eosinophils versus change from baseline in FEV1 at week 12 did not seem to suggest association of baseline eosinophils and treatment effect, as measured by change from baseline in FEV1 at week 12 in the study population (baseline eosinophils 0.3 Giga/L). Baseline eosinophils correlated with decreased ACQ and decreased albuterol/levalbuterol use. Periostin and YKL-40 at baseline correlated with decreased ACQ.

The FEV1 change from baseline at week 12 was compounded by the withdrawal of ICS (starting at week 4). Similar analyses did not suggest association between baseline TARC or IgE and change from baseline in FEV1 at week 12 in the study population (baseline eosinophils ≥0.3 Giga/L).

H. Summary

These results show that mAb1 significantly reduced serum biomarkers associated with Th2 inflammation (TARC, eotaxin-3 and IgE) and bronchial inflammation (FeNO) in adult asthma patients. The correlation between FeNO reduction and FEV, improvement suggests a relationship between IL-4/IL-13 mediated anti-inflammatory activity and improvement in pulmonary function in moderate-to-severe, uncontrolled asthma.

Example 3. Clinical Trial of Subcutaneously Administered Anti-IL-4R Antibody (mAb1) in Patients with Bilateral Nasal Polyposis and Chronic Symptoms of Sinusitis A. Study Objectives and Overview The positive effect of mAb1 on the SNOT-22 test described in Example 1 suggested that the anti-IL-4R antibody might also be effective for treating nasal polyposis. Further, nasal polyps are most commonly eosinophilic/TH2 driven, and mAb1 significantly reduced biomarkers associated with Th2 inflammation (see Example 2). A clinical trial was therefore designed to test the therapeutic effect of mAb1 on nasal polyposis.

A randomized, double-blind, phase 2, placebo controlled, 2 arm study will be performed to evaluate mAb1 administered once a week (QW) subcutaneously (SC) for 16 weeks in patients with bilateral nasal polyposis and chronic symptoms of sinusitis. The primary objective of the study will be to evaluate the efficacy of mAb1 in the treatment of bilateral nasal polyposis (NP) by assessment of the endoscopic nasal polyp score in comparison to placebo. Secondary objectives of the study include evaluation of mAb1 in patients with bilateral nasal polyps with regards to symptoms of sinusitis, Computed Tomography (CT) scan changes, Nasal polyp score in the sub-group of patients with co-morbid asthma, safety and tolerability, pharmacodynamic responses based on suppression of TH2 biomarkers, concentrations of mAb1 in serum, immune response to mAb1 (Anti-drug antibodies (ADA)), and effect of mAb1 in patient reported outcomes and Quality of Life (QoL) scales.

mAb1 will be administered concomitantly with Mometasone furoate nasal spray (MFNS). Also, there is high co-morbidity of NP with asthma, aspirin/nonsteroidal anti-inflammatory drug (NSAID) hypersensitivity and previous surgeries, and therefore patients will be allowed to enter the study unless they present any of the exclusion criteria described below. Approximately 56 patients will be randomized into 2 treatment groups of 28 patients per group. To ensure at least 28 patients with co-morbid asthma are included in the study, recruitment of NP patients without co-morbid asthma will stop when approximately 28 patients without asthma are randomized. Both the patient and the investigator will be blinded to the assigned treatment group.

The study will consist of three periods: 1) a four week screening run in period on MFNS (Visit 1); (2) a 16 week randomized mAb1 or placebo treatment period (Visits 2-18); and (3) a 16 week post-treatment period to assay pharmacokinetics, immunogenicity, safety and efficacy (Visits 19-22). The total duration of the study is up to 36 weeks.

The primary endpoint will be the change from baseline at Week 16 in bilateral nasal polyp score (NPS).

Numerous secondary efficacy endpoints will be measured to more comprehensively evaluate the efficacy of mAb1. The study will explore improvement of nasal polyposis and associated sinus inflammation in CT scan, improvement in condition specific and general medical questionnaires in order to obtain a better understanding of the impact of severe nasal polyposis on the subject's quality of life (QOL).

These endpoints, together with exploratory sub-group analysis and biomarkers will provide the information on the therapeutic value of mAb1 to reduce nasal polyp score and to improve symptoms in NP and its subsets. The sustainability of the effect will be also explored through the 4-month post-treatment evaluation period.

The 300 mg QW dose regimen is anticipated to saturate apparent target mediated clearance level (10-15 mg/L). This regimen has been tested and provided statistically significant and clinically relevant response in two previous proof of concept studies performed with mAb1 in asthma and atopic dermatitis (see, e.g., Example 1 above, U.S. Ser. No. 61/805,797 and U.S. Ser. No. 61/816,191). The first dose will employ a loading dose of 600 mg in order to achieve faster steady-state concentration. This loading dose range is supported by the acceptable safety profile of the highest loading dose (600 mg) demonstrated in a prior study conducted in Japanese healthy subjects.

In addition, given that the Cmax after 600 mg loading dose is around 70 mg/L and that the steady state Ctrough of 300 mg QW is around 150 mg/L, the Cmax after the proposed dosing regimen (ie, 600 mg loading dose followed by 300 mg QW) will be below the mean Cmax of 12 mg/kg IV dose (421 mg/L), the highest single dose tested in healthy subjects that was well tolerated, providing additional confidence that this dose regimen should have an acceptable safety profile.

Patient inclusion criteria include (i) a physician endoscopic diagnosis of bilateral nasal polyposis (i.e., a minimum bilateral nasal polyp score of 5 out of a maximum score of 8 for both nostrils, with at least a score of 2 for each nostril, despite completion of a prior INCS (intranasal corticosteroid) treatment) for at least 8 weeks before screening, and (ii) chronic symptoms of sinusitis, which are the presence of at least two of the following symptoms prior to screening: nasal blockade/obstruction/congestion or nasal discharge (anterior/posterior nasal drip); facial pain/pressure; and reduction or loss of smell.

Patients who have met these criteria will be screened for the following exclusion criteria: age <18 or >65 years; any technical/administrative reason that makes it impossible to randomize the patient in the study; previous participation in any clinical trial of mAb1; a SNOT22 score <7; receipt of any other investigational drug or prohibited therapy for this study within 2 months before screening or 5 half-lives, whichever is longer; receipt of oral corticosteroids (OCS) or intranasal corticosteroid drops within 2 months or 1 month before screening or scheduled to receive OCS during the study period for another condition; treatment with mAB or immunosuppressive therapy; treatment with an anti-immunoglobulin E (IgE) therapy (e.g., omalizumab) within 130 days of Visit 1; treatment with a leukotriene antagonist/modifier for patients who were not on a continuous treatment for 30 days prior to Visit 1; initiation of allergen immunotherapy within 3 months prior to Visit 1 or a plan to begin therapy during the Screening Period or the Randomized Treatment Period; any nasal surgery within six months before screening or have had more than five sinonasal surgeries in the past of which maximal two were surgeries changing the lateral wall structure of the nose; or a condition/concomitant disease that makes a patient non-evaluable for the primary efficacy endpoint (e.g., antrochoanal polyps; nasal septal deviation that would occlude at least one nostril; acute sinusitis, nasal infection or upper respiratory infection at screening or in the 2 weeks before screening; ongoing rhinitis medicamentosa; Churg-Strauss syndrome, Young's syndrome, Kartagener's syndrome or dyskinetic ciliary syndromes, Cystic fibrosis; signs or a CT scan suggestive of Allergic fungal rhinosinusitis). Patients with co-morbid asthma are excluded if: the patient has a forced expiratory volume (FEV1) of 60% or less; an exacerbation requiring systemic (oral and/or parenteral) steroid treatment or Hospitalization (>24h) for treatment of asthma, has occurred within 3 months prior screening; or the patient is receiving a dose higher than 1000 μg fluticasone or the equivalent of inhaled corticosteroids. Other exclusion criteria include patients with short life expectancy (less than 6 months); patients receiving concomitant treatment prohibited in the study; women who are pregnant or intend to become pregnant during the study, or breast-feeding women. Other exclusion criteria include concomitant severe diseases (e.g., active and inactive pulmonary tuberculosis, Diabetes mellitus etc.); diagnosed active parasitic infection; suspected or high risk of parasitic infection; history of human immunodeficiency virus (HIV) infection or positive HIV screen at Visit 1; evidence of acute or chronic infection; known or suspected immunosuppression, including history of invasive opportunistic infections (eg, tuberculosis, histoplasmosis, listeriosis, coccidioidomycosis, pneumocystosis, aspergillosis), despite infection resolution; live vaccinations within 12 weeks prior to Visit 1 or planned vaccinations during the study; patients with active autoimmune disease or patients using immunosuppressive therapy for autoimmune disease (eg, Hashimoto's thyroiditis, Graves' disease, inflammatory bowel disease, primary biliary cirrhosis, systemic lupus erythematous, multiple sclerosis, psoriasis vulgaris, rheumatoid arthritis); patients with positive or indeterminate hepatitis B surface antigen (HBsAg), hepatitis B core antibody (HBcAb), or hepatitis C antibody at Visit 1; patients with liver injury related criteria (e.g., underlying hepatobiliary disease, or ALT>3 ULN).

B. Study Treatments

Investigational Product: Sterile mAb1 of various concentrations will be provided in 5 mL glass vials. Each vial will contain a withdrawable volume of 2 mL: 150 mg/mL solution (300 mg dose/2 mL). Sterile placebo will be provided in identically matched glass 5 mL vials, where each vial contains a deliverable volume of 2 mL.

mAb1 will be administered every 7±2 days (QW). The doses of mAb1 will be separated by ≥5 days to avoid an overdose. At Visit 2 (V2), 2 injections will be performed. After V2 one injection of mAb1 will be performed weekly at the investigational site throughout the randomized treatment period. The mAb1 will be administered following clinic procedures and blood collection. Patients will be monitored for at least 1 hour after each administration for any signs or symptoms of a local site injection or hypersensitivity reaction. Subcutaneous injection sites will be alternated between the 4 quadrants of the abdomen (avoiding navel and waist areas) or upper thighs so that the same site is not injected for two consecutive times/weeks.

On a daily basis throughout the study, the subject will use an electronic diary to record daily use of MFNS. Mometasone furoate (NASONEX®) 50 micrograms/actuation Nasal Spray, is contained in a bottle, that contains 18 g (140 actuations) of product formulation.

Screening Period:

Prior to screening, subjects must be on a stable dose of intranasal corticosteroids (INCS) for ≥2 month prior to Visit 1. If the patient is using an alternative INCS product other than MFNS prior to the screening visit, at V1, the patient will be switched to MFNS. After V1 all patients will enter a run-in period of 4 weeks where they will receive MFNS: 2 actuations (50 μg/actuation) in each nostril twice daily (BID) (total daily dose of 400 μg), unless they are intolerant to BID INCS in which case, they can stay on the lower dose (QD) regimen. To be accepted for the study, patients must also have presence of at least two of the following symptoms prior to screening: Nasal blockade/obstruction/congestion or nasal discharge (anterior/posterior nasal drip); +/−facial pain/pressure or +/−reduction or loss of smell Treatment Period:

The treatment period will proceed as indicated in the Study Flow-chart at Table 14.

TABLE 14

| | Screening | Randomized treatment period | | | | | | | | | | | | | | | | | Post-treatment period | | | |
|---|---|---|---|---|---|---|---|---|---|---|---|---|---|---|---|---|---|---|---|---|---|---|
| | period | RDN | | | | | | | | | | | | | | | | EOT[a] | | | | EOS |
| | VISIT | | | | | | | | | | | | | | | | | | | | | |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| | Week (DAY) | | | | | | | | | | | | | | | | | | | | | |
| | W −4 (D −28) | W 0 (D 1) | 1 | 2 | 3 | 4 | 5 | 6 | 7 | 8 | 9 | 10 | 11 | 12 | 13 | 14 | 15 | 16 | 20 | 24 | 28 | 32 |
| Inclusion Criteria including Informed Consent (s) | X | X | | | | | | | | | | | | | | | | | | | | |
| Exclusion Criteria | X | X | | | | | | | | | | | | | | | | | | | | |
| Patient Demography | X | | | | | | | | | | | | | | | | | | | | | |
| Medical/Surgical History | X | | | | | | | | | | | | | | | | | | | | | |
| Prior Medication History[b] | X | | | | | | | | | | | | | | | | | | | | | |
| Physical Examination | X | | | | | | | | | | | | | | | | | X | | | | X |
| Spirometry[c] | | X | | | | X | | | | X | | | | X | | | | X | | | | |
| Randomization | | X | | | | | | | | | | | | | | | | | | | | |
| Treatment: | | | | | | | | | | | | | | | | | | | | | | |
| mAb1 weekly SC administration[d] | | X (loading) | X | X | X | X | X | X | X | X | X | X | X | X | X | X | X | | | | | |
| Call IVRS | X | X | X | X | X | X | X | X | X | X | X | X | X | X | X | X | X | X | | | | X |
| Dispense or download electronic diary/NPIF[e] | X | X | | | | X | | | | X | | | | X | | | | X | X | X | X | X |
| NIMP (MFNS) | ------------------------------------------------------------------------ | | | | | | | | | | | | | | | | | | | | | |
| Record concomitant medication | ------------------------------------------------------------------------ | | | | | | | | | | | | | | | | | | | | | |
| Efficacy | | | | | | | | | | | | | | | | | | | | | | |
| Nasal endoscopy[f] | X | X | | | | X | | | | X | | | | X | | | | X | | | | X |
| CT scan[g] | | X | | | | | | | | | | | | | | | | X | | | | |
| Smell test (UPSIT) | | X | | | | | | | | X | | | | | | | | X | | | | |
| SNOT- 22 | X | X | | | | X | | | | X | | | | X | | | | X | | | | X |
| Visual analogue scale (VAS) | | X | | | | X | | | | X | | | | X | | | | X | | | | X |
| QoL (SF-36, EQ-5D) | | X | | | | X | | | | X | | | | X | | | | X | | | | X |
| Nasal polyp related resource use questionnaire | | X | | | | X | | | | X | | | | X | | | | X | | | | X |
| ACQ-5[h] | | X | | | | X | | | | X | | | | X | | | | X | | | | X |
| Safety | | | | | | | | | | | | | | | | | | | | | | |
| AE/SAE recording (if any) | ------------------------------------------------------------------------ | | | | | | | | | | | | | | | | | | | | | |
| Vital Signs | X | X | | | | X | | | | X | | | | X | | | | X | X | X | X | X |
| ECG | X | | | | | | | | | X | | | | X | | | | X | | | | X |
| Laboratory Testing | | | | | | | | | | | | | | | | | | | | | | |
| Clinical laboratory testing[i] | X | X | | | | X | | | | X | | | | X | | | | X | | X | | X |
| Urinalysis (dipstick) | X | | | | | | | | | X | | | | | | | | X | | | | X |
| Pregnancy test (for WOCBP)[j] | X | X | | | | X | | | | X | | | | X | | | | X | | | | X |
| PK/Anti-drug antibody sampling PK[k] | | X | | X | | X | | | | X | | | | X | | | | X | X | X | X | X |
| Serum Biomarker sampling | | X | | X | | X | | | | X | | | | X | | | | X | X | | | X |
| Archival nasal secretion sampling[m] | | X | | | | X | | | | X | | | | X | | | | X | X | | | |
| Polyp biopsy[n] | | X | | | | | | | | | | | | | | | | X | | | | |
| Stored DNA sampling | | X | | | | | | | | | | | | | | | | | | | | |

TABLE 14-continued

| | Screening | Randomized treatment period | | | | | | | | | | | | | | | | | Post-treatment period | | | |
|---|---|---|---|---|---|---|---|---|---|---|---|---|---|---|---|---|---|---|---|---|---|---|
| | period | RDN | | | | | | | VISIT | | | | | | | | | EOT[a] | | | | EOS |
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| | | | | | | | | | Week (DAY) | | | | | | | | | | | | | |
| | W −4 (D −28) | W 0 (D 1) | 1 | 2 | 3 | 4 | 5 | 6 | 7 | 8 | 9 | 10 | 11 | 12 | 13 | 14 | 15 | 16 | 20 | 24 | 28 | 32 |
| Stored whole blood RNA sampling[o] | | X | | X | | | | | | | | | | | | | | X | | | | X |

The Screening Period is 28 days in duration to run in any patient on MFNS, and to collect baseline data. V2 will take place 28 days +/− 2 day window after V1

[a]No mAb1 administration during this visit. Patients who discontinue treatment early will be assessed as soon as possible using the procedures normally planned for the End-of-treatment Visit and the 4 Post-treatment Period Visits.

[b]Prior to screening, patients must be on a stable dose of INCS for more than 8 weeks

[c]Spirometry: all patients should have FEV1 anytime during Screening Period (before V2) and at the other scheduled visits during the Randomized treatment period

[d]Weekly mAb1 administrations starting from V2 at the site investigational site must be separated by at least 5 days.

[e]Electronic diary/NPIF meter is used for daily recording of MFNS use, nocturnal awakenings, morning and evening NPIF and rhinosinusitis symptom scores 1) nasal congestion/obstruction 2) anterior rhinorrhea (runny nose), 3) posterior rhinorrhea (post nasal drip), and 4) loss of sense of smell, scored using a 0-3 categorical scale where 0 = no symptoms, 1 = mild symptoms, 2 = moderate symptoms and 3 = severe symptoms); This device is dispensed at Visit 1 and information is downloaded from this device on the other indicated days. The average of the last 7 days before V2 is needed to determine the baseline value

[f]Nasal endoscopy: endoscopy (including use of decongestants before the procedure) will be performed after all other efficacy assessments have been completed for each visit; Standard video sequences will be downloaded by the investigator to the central reader's secured Internet site. For eligibility central reading of V1 will be used. At V2 investigator review V1 results from central reader to confirm entry criteria and reconfirm eligibility based on review of Inclusion/Exclusion Criteria and the V2 endoscopy local reading

[g]CT scan should be performed anytime during Screening Period before a first administration of mAb1 and at EOT. Central reading will be used for comparison baseline (BL) to EOT

[h]Only for patients with co-morbid asthma, ACQ-5 is completed in the patient's electronic diary during clinic visits.

[i]Hematology: hemoglobin, hematocrit, platelet count, total white blood cell count with five-part differential count, differential count, and total red blood cell count. Serum chemistry (Obtain fasting at planned visits but V2): creatinine, blood urea nitrogen, glucose, uric acid, total cholesterol, total protein, albumin, total bilirubin, alanine aminotransferase, aspartate aminotransferase, alkaline phosphatase, electrolytes (sodium, potassium, chloride), bicarbonate, and creatine phosphokinase. Clinical laboratory testing at Visit 1 includes hepatitis screen (hepatitis B surface antigen (HBsAg), Hepatitis B IgM core antibody (HBcAb-IgM), hepatitis C antibodies (HC Ab), HIV screen (Anti-HIV-1 and HIV-2 antibodies), anti-nuclear antibody (ANA). Clinical laboratory testing at Visit 2 is limited to hematology and a separate hematology sample obtained for local analysis. Note: Anti-ds DNA antibody will be tested if ANA is positive (≥1:160 titer). Clinical lab testing at Visit 2 consists of hematology only

[j]Serum pregnancy test at Visit 1 and urine pregnancy tests at other visits. A negative result must be obtained at Visits 1 and 2 prior to randomization visits

[k]Serum pharmacokinetic samples, immune response assessment (ADA) samples and optional whole blood RNA samples will be collected prior to administration of investigational product during the Randomized Treatment Period. During the post-treatment period PK samples will be collected at all visits and ADA samples only at EOS visit. Patients with titers >1000 of the ADA at last visit may be followed after the study. Blood samples for PK and ADA assessment will be collected at any time iln case an SAE occurs.

[m]Nasal secretion samples will be collected and stored for potential future discovery efforts to identify predictors of treatment response

[n]Optional polyp biopsies will be collected in selected clinical centers

[o]Samples will be collected prior to administration of investigational product during the Randomized Treatment Period During the Treatment Period, patients will continue the stable dose of mometasone furoate: two actuations of MFNS in each nostril BID or QD (in case patient cannot tolerate the high dose). At Visit 2, patients will be administered the SNOT-22 test, VAS and QoL questionnaires (SF-36, EQ-5D, Nasal polyp related resource use questionnaire), the smell test, and the ACQ-5 in patients with asthma.

Clinical laboratory testing at Visit 2 is limited to hematology, pharmacokinetics, anti-drug antibodies, biomarkers in serum and plasma, allergen-specific IgE panel sampling. Blood samples are taken prior to administration of mAb1. Nasal secretion sampling for biomarkers. For those patients who have signed a specific informed consent form, collect blood sample for DNA and RNA sampling (prior to administration of investigational product during the Randomized Treatment Period).

Temporary treatment discontinuation may be considered by the Investigator because of suspected AEs. Reinitiation of treatment with mAb1 will be done under close and appropriate clinical/and or laboratory monitoring once the Investigator will have considered according to his/her best medical judgment that the responsibility of mAb1 in the occurrence of the concerned event was unlikely and if the selection criteria for the study are still met.

An adverse event (AE) is any untoward medical occurrence in a patient or clinical investigation patient administered a pharmaceutical product and which does not necessarily have to have a causal relationship with this treatment.

A serious adverse event (SAE) is any untoward medical occurrence that at any dose: results in death, or is life-threatening, (the term "life-threatening" in the definition of "serious" refers to an event in which the patient was at risk of death at the time of the event; it does not refer to an event which hypothetically might have caused death if it were more severe); requires inpatient hospitalization or prolongation of existing hospitalization, or results in persistent or significant disability/incapacity, or is a congenital anomaly/birth defect; is a medically important event Medical and scientific judgment should be exercised in deciding whether expedited reporting is appropriate in other situations, such as important medical events that may not be immediately life-threatening or result in death or hospitalization but may jeopardize the patient or may require intervention (ie, specific measures or corrective treatment) to prevent one of the other outcomes listed in the definition above (the following list of medically important events is intended to serve as a guideline for determining which condition has to be considered as a medically important event. The list is not intended to be exhaustive: intensive treatment in an emergency room or at home for: Allergic bronchospasm, anaphylaxis, blood dyscrasias (ie, agranulocytosis, aplastic anemia, bone marrow aplasia, myelodysplasia, pancytopenia, etc), convulsions (seizures, epilepsy, epileptic fit, absence, etc), development of drug dependency or drug abuse); ALT >3×ULN+total bilirubin >2×ULN or asymptomatic ALT increase >10×ULN; Suicide attempt or any event suggestive of suicidality; syncope, loss of consciousness (except if documented as a consequence of blood sampling); bullous cutaneous eruptions; Cancers diagnosed during the study or aggravated during the study; chronic neurodegenerative diseases (newly diagnosed) or aggravated during the study (only if judged unusual/significant by the Investigators in studies assessing specifically the effect of a study drug on these diseases).

Post-Treatment Period:

Upon completing the Randomized Treatment Period (or following early discontinuation of mAb1), patients will continue treatment with the stable dose of MFNS maintained over the randomized treatment period, or modify treatment based on medical judgment.

The following concomitant treatments are not permitted during the Screening Period and the Randomized treatment period: use of intranasal medication that would interfere with the symptoms of diseases (antihistamines, nasal atropine, ipratropium bromide, nasal cromolyn), except nasal saline; INCS drops; systemic corticosteroid; decongestion (topical or systemic), except before endoscopy; long term use of systemic antibiotics (for 2 weeks or more); lipoxygenase inhibitors; any immunosupressive treatment including but not limited to methotrexate, cyclosporine, mycophenolate, tacrilomus, gold, penicillamine, sulfasalazine, hydroxychloroquine, azathioprine, cyclophosphamide; anti-immunoglobulin E (IgE) therapy (omalizumab); and aspirin or NSAID in patients with hypersensitivity to aspirin.

The following concomitant treatments are allowed: MFNS during the screening and throughout the whole study; Nasal normal saline; Topical decongestants (e.g., Oxymetazoline hydrochloride to reduce the swelling and widen the path for the endoscope), as well as a topical anesthetic e.g. Lidocaine are allowed before endoscopy; short term use of Antibiotics (<2 weeks); and for patients with asthma, SABA, LABA, and Methylxanthines (e.g., theophylline, aminophyllines). The following inhaled corticosteroids are allowed for patients on a stable dose ≤1000 μg Fluticasone (or the equivalent dose of another inhaled CS; see Table 16) and only for patients that were on a stable dose ≥30 days prior to Visit 1: Leukotriene antagonists/modifiers are permitted during the study, only for patients that were on a continuous treatment for ≥30 days prior to Visit 1; Systemic antihistamines; and Initiation of allergen immunotherapy (allergen immunotherapy in place for ≥3 months prior to Visit 1 is permitted).

C. Efficacy of Treatment

The primary endpoint of this study is the change from baseline at week 16 in bilateral endoscopic Nasal Polyp Score.

TABLE 15

| Polyp score | Polyp size |
|---|---|
| 0 | No polyps |
| 1 | Small polyps in the middle meatus not reaching below the inferior border of the middle turbinate |
| 2 | Polyps reaching below the lower border of the middle turbinate |
| 3 | Large polyps reaching the lower border of the inferior turbinate or polyps medial to the middle turbinate |
| 4 | Large polyps causing complete obstruction of the inferior nasal cavity |

Nasal endoscopy will be performed at the end of the scheduled visits and preceded by local administration of anaesthetic drugs in combination with a decongestant. Standard video sequences will be downloaded or sent to a centralized reader. Centralized imaging data assessments and scoring by an independent physician reviewer for the imaging data will be performed for all endoscopies. To confirm eligibility at V2, only the V1 central reading will be made available to the site. The final results of central reading will be made available after the study.

For the analysis of the primary endpoint, central reading of V2 will be used for comparison with EOT reading. The sites will remove subject-identifying information from the imaging data header prior to sending the imaging data to the central reader.

Secondary endpoints of the study will include change from baseline at Week 16 in: patient reported symptoms (including 22-item Sinonasal Outcome Test (SNOT-22)); subject-assessed nasal congestion/obstruction, anterior rhinorrhea (runny nose), posterior rhinorrhea (post nasal drip), and loss of sense of smell, (daily AM and PM e-diary) month average; number of nocturnal awakenings; patient-rated rhinosinusitis symptoms severity using a visual analog scale (VAS); 5-item Asthma control questionnaire (ACQ-5) in asthma sub-group); nasal peak inspiratory flow (NPIF); smell test (UPSIT); NPS in patients with co-morbid asthma; CT scan assessments; Spirometry (overall and in sub-group with asthma); time to first response point improvement) in NPS; time to study treatment discontinuation; and incidence of treatment discontinuation due to need for OCS or nasal surgery.

Quality of life (QoL) end points will include change from baseline at Week 16 in: 36-item short form health survey (SF36); European quality of life scale (EQ-5D); and Nasal polyp related resource use questionnaire.

Disease-specific efficacy measures include: Computed tomography (CT). CT of the sinuses should be performed before V2 and at EOT. For both Lund-Mackay scores and 3D volumetric measurement of the maxillary sinus, the same acquisitions (sequences) will be used for centralized imaging data assessments and scoring by an independent physician reviewer for the imaging data. Central reading of V2 will be used for comparison with EOT. The final results of central reading will be made available after the study.

For Three-Dimensional volumetric measurement of the maxillary sinus, central reading before V2 will be used for comparison with EOT reading. The sites will remove subject-identifying information from the imaging data header prior to sending the imaging data to the central reader. The % change in opacification from BL to EOT will be calculated.

At screening (Visit 1), patients will be issued an NPIF meter for recording morning (AM) and evening (PM) NPIF. The patients will be instructed to record the following variables in the e-diary on a daily basis: AM NPIF performed within 15 minutes after arising (between 6 am and 10 am) prior to taking MFNS; and PM NPIF performed in the evening (between 6 pm and 10 pm) prior to taking MFNS.

Three NPIF efforts will be performed by the patient; all 3 values will be recorded by the patient in the e-diary, and the highest value will be used for evaluation. The baseline AM NPIF will be the mean AM measurement recorded for the 28 days prior to the first dose of investigational product, and baseline PM NPIF will be the mean PM measurement recorded for the 28 days prior to the first dose of investigational product.

To assess disease-specific, daily symptoms, the patient will use an electronic diary to: respond to the morning and evening individual rhinosinusitis symptom questions using a 0-3 categorical scale (where 0=no symptoms, 1=mild symptoms, 2=moderate symptoms and 3=severe symptoms), and including the symptoms of congestion and/or obstruction, anterior rhinorrhea (runny nose), posterior rhinorrhea (post-nasal drip), and loss of sense of smell. The number of nocturnal awakenings will also be recorded.

The same safety assessments will be applied across all arms. Adverse events, including serious adverse events (SAEs) and adverse events of special interest (AESI), will be collected at every visit.

Predose blood samples will be collected for determination of serum functional mAb1 and anti-mAb1 antibodies as designated in Table 14.

Optional sampling for exploratory analysis of DNA and RNA, requiring separate pharmacogenetics informed consent.

Pharmacokinetics.

Functional mAb1 and anti-mAb1 antibodies in serum will be assayed by ELISA. Predose functional mAb1 concentrations in serum at Visit 2 (Day 1), mAb1 trough concentrations at Week 2, Week 4, Week 8, Week 12, Week 16, and follow-up serum mAb1 at Week 20, Week 24, Week 28 and Week 32 will be provided. Anti-mAb1 antibody status (negative or titer value) at Visit 2 (Day 1), Week 2, Week 4, Week 8, Week 12, Week 16, and Week 32 will also be provided. Patients with ADA titers 000 at the end of study visit will be scheduled to return approximately 6 months later for an additional assessment of ADA titer. Further follow-up will be considered based on the overall assessment of antibody titers and clinical presentation.

Pharmacodynamics.

Since the secretion of certain proteins is dependent, at least in part, on Th2 cytokines and is associated with chronic inflammation of the airway mucosa, including sinus tissue, expression of certain biomarkers will be assayed to monitor a therapeutic effect of mAb1. These biomarkers also will be assessed for their value in predicting toxicity and/or in documenting the time course of drug response. The values to be used as baselines will be those collected on Day 1 (predose assessments).

Nasal secretions will be obtained by inserting nasal swabs bilaterally into the nasal cavity for five minutes. The nasal secretions will be preserved for possible analysis of additional biomarkers related to nasal polyposis and responses to mAb1 treatment.

At selected clinical site (s) and with specific informed consent, nasal polyp tissue will be optionally obtained by biopsy. A baseline biopsy will be obtained at V2 of the study. After randomization, another biopsy of nasal polyp tissue will be obtained at the end of treatment visit (Week 16).

The biopsied nasal polyp tissue will be assessed for various biomarkers of inflammation and disease process or response. For example, RNA will be extracted and used for expression profiling (e.g., microarray, transcriptome sequencing or quantitative RT-PCR).

DNA and RNA samples may be used to determine a possible relationship between genes and response to treatment with mAb1 and possible side effects to mAb1.

Analysis of proportion of patients with binary events. Proportion of patients with binary events will be assessed for: ≥1 point improvement (reduction) in NPS at week 16 (as read centrally); 10% or more improvement in CT opacification from baseline at week 16; drop-out due to oral CS or surgery; or INCS increase after 8 weeks will be analyzed using a logistic model with the above responses, respectively, as the response variable, and treatment group, pooled countries/regions and the stratification factor(s) prior to the study as covariates.

Analysis of time to event variables. Time to event (e.g., the first response with ≥1 point improvement (reduction) in NPS, study treatment discontinuation, etc) will be analyzed suing a Cox regression model with time to event as the dependent variable, and treatment, pooled countries/regions, asthma comorbidity prior to the study as covariates. The Kaplan-Meier method will be used to derive the proportion of patients with an event at Week 4, 8, 12 and 16 specific to each treatment group. For analysis during the treatment period, if a patient has no event before treatment discontinuation/completion, then the patient will be considered as free of event till the end of treatment period (last dose date+7 days).

Analysis of change from baseline for continuous variables. The change from baseline at week 16 in: NPS for patients with co-morbid asthma; Lund Mackay score; 22-item Sinonasal Outcome Test (SNOT-22); Subject-assessed congestion and/or obstruction score; nasal peak inspiratory flow (NPIF); ACQ-5 in patients with co-morbid asthma; QoL measures (SF36, EQ-5D), and VAS will be analyzed using MMRM same as the primary endpoints. Descriptive statistics including number of patients, mean, standard error and LS means will be provided. In addition, differences in LS means, the corresponding 95% CI and the p-value will be provided for comparisons of each dose against placebo.

Analysis of efficacy in baseline biomarker of characteristics defined subsets. To examine baseline biomarkers for their potential value to predict treatment response, analyses of change in NPS will also be performed for the following subsets and the entire ITT population by each dose group and selected pooled dose group.

Subgroup analysis. To assess the consistency treatment effects across the subgroup levels and to examine baseline biomarkers for their potential value to predict treatment response, exploratory subgroup analyses will be conducted for the change from baseline in NPS with respect to age group, gender, region, race, INCS dose level, baseline NPS, baseline CT scan score, asthma comorbidity, and selected biomarkers prior to the study.

Listings of anti-mAb1 antibody results (Negative or titer value) will be presented by patient, time point and treatment groups. ADA titer levels will be classified into categories: Low, moderate and high. Low levels of ADA titers are defined as titers below 1000; moderate levels of ADA titers are defined as titers between 1000 and 10,000; high levels of ADA titers are defined as titers >10,000.

Anti-mAb1 antibody assay results will be described categorically. The following summary will be provided for: Patients with any positive ADA assay response during the TEAE period; Patients with treatment induced positive ADA assay response during the TEAE period; Patients with treatment induced positive ADA assay response during the TEAE period will be further described as patients with transient positive response and patients with persistent positive response. Patients with any positive ADA assay response during the TEAE period is defined as those having at least one sample positive in the ADA assay.

The treatment induced positive ADA assay response is defined as: Patients with no positive assay response at baseline but with a positive assay response during the TEAE period or patients with a positive ADA assay response at baseline and also have at least a 4-fold increase in titer during the TEAE period.

A persistent positive response is a treatment induced positive ADA assay response in which at least 2 consecutive post-baseline samples from a patient are positive in the ADA assay or the last post-baseline sample collected is positive in the ADA assay. A transient positive response is defined as any treatment induced positive ADA assay response that is not considered persistent.

TABLE 16

Allowable Inhaled Glucocorticosteroid/Long-Acting Beta2 Agonist Combination Products and Acceptable Dosage Form, Strength and Dosage Schedule

| Generic Name | Brand Name | Acceptable Product | Acceptable Dosage Form, Strength and Dosage Schedule |
|---|---|---|---|
| Fluticasone propionate and salmeterol | Advair ®/ Seretide ® | DPI (250/50 or 500/50) | DPI: 1 puff twice daily (500/50) |
| | | | DPI: 1 puffs twice daily (250/50) |
| | | MDI (115/21 or 230/21) | MDI: 2 puffs twice daily (115/21) |
| | | | MDI: 2 puffs twice daily (230/21) |
| Budesonide and formoterol | Symbicort ® | DPI (200/6 or 400/12 | DPI: 1 puff twice daily (400/12) |
| | | | DPI: 2 puffs twice daily (200/6) |
| | | MDI (160/4.5) | MDI: 2 puffs twice daily (160/4.5) |
| Mometasone furoate and formoterol | Dulera ® | MDI (100/5 or 200/5) | MDI: 2 puffs twice daily (200/5) |
| | | | MDI: 2 puffs twice daily (100/5) |

The present invention is not to be limited in scope by the specific embodiments described herein. Indeed, various modifications in addition to those described herein will become apparent to those skilled in the art from the foregoing description and the accompanying FIGURE. Such modifications are intended to fall within the scope of the appended claims.

What is claimed is:

1. A method for treating nasal polyposis in a subject in need thereof, wherein the subject has nasal polyposis that is inadequately controlled by surgery to remove nasal polyps, comprising:

administering to the subject a full antibody that specifically binds an interleukin-4 receptor (IL-4R), wherein the antibody comprises a heavy chain variable region (HCVR) sequence comprising the amino acid sequence of SEQ ID NO: 1 and a light chain variable region (LCVR) sequence comprising the amino acid sequence of SEQ ID NO: 2.

2. The method of claim 1, wherein the antibody is dupilumab.

3. The method of claim 1, wherein the antibody is administered to the subject subcutaneously.

4. The method of claim 1, wherein the antibody is administered at a dose of 0.1 mg to 600 mg.

5. The method of claim 1, wherein the antibody is administered at a dose of 100 mg to 400 mg.

6. The method of claim 1, wherein the antibody is administered at a dose of 300 mg.

7. The method of claim 1, wherein the antibody is administered to the subject subcutaneously at a dose of 300 mg.

8. The method of claim 1, wherein a second therapeutic agent is administered to the subject before, after or concurrent with the antibody.

9. The method of claim 8, wherein the second therapeutic agent is selected from the group consisting of an IgE inhibitor, an antibiotic agent, and an anti-fungal agent.

10. The method of claim 8, wherein the second therapeutic agent comprises an intranasal corticosteroid.

11. The method of claim 10, wherein the intranasal corticosteroid is mometasone furoate nasal spray (MFNS).

12. The method of claim 8, wherein the second therapeutic agent comprises an inhaled corticosteroid, wherein the inhaled corticosteroid is fluticasone or budesonide.

13. The method of claim 12, wherein the second therapeutic agent is part of a combination therapy further comprising a long-acting $beta_2$ agonist, wherein the long-acting $beta_2$ agonist is salmeterol or formoterol.

14. The method of claim 8, wherein the second therapeutic agent comprises a fluticasone/salmeterol combination therapy.

15. The method of claim 8, wherein the second therapeutic agent comprises a budesonide/formoterol combination therapy.

16. The method of claim 8, wherein a second therapeutic agent selected from the group consisting of a nasal saline, a topical decongestant, a topical anesthetic, a leukotriene antagonist, and a systemic antihistamine is administered to the subject before, after, or concurrent with the antibody.

17. A method for treating nasal polyposis in a subject in need thereof, wherein the subject has nasal polyposis that is inadequately controlled by surgery to remove nasal polyps, comprising:

administering to the subject an initial dose of a full antibody that specifically binds an interleukin-4 receptor (IL-4R), followed by one or more subsequent doses of the antibody, wherein the antibody comprises a heavy chain variable region (HCVR) sequence comprising the amino acid sequence of SEQ ID NO: 1 and a light chain variable region (LCVR) sequence comprising the amino acid sequence of SEQ ID NO: 2.

18. The method of claim 17, wherein the antibody is dupilumab.

19. The method of claim 17, wherein each subsequent dose of the antibody is administered 2 weeks after the immediately preceding dose of the antibody.

20. The method of claim 17, wherein each subsequent dose of the antibody is administered 4 weeks after the immediately preceding dose of the antibody.

21. The method of claim 17, wherein the initial dose of the antibody and the one or more subsequent doses of the antibody are administered subcutaneously.

22. The method of claim 17, wherein the initial dose of the antibody and the one or more subsequent doses of the antibody each comprises 300 mg.

23. The method of claim 17, wherein a second therapeutic agent is administered to the subject before, after or concurrent with the initial dose of the antibody or the one or more subsequent doses of the antibody.

24. The method of claim 23, wherein the second therapeutic agent is selected from the group consisting of an IgE inhibitor, an antibiotic agent, and an anti-fungal agent.

25. The method of claim 23, wherein the second therapeutic agent comprises an intranasal corticosteroid.

26. The method of claim 25, wherein the intranasal corticosteroid is mometasone furoate nasal spray (MFNS).

27. The method of claim 23, wherein the second therapeutic agent comprises an inhaled corticosteroid, wherein the inhaled corticosteroid is fluticasone or budesonide.

28. The method of claim 27, wherein the second therapeutic agent is part of a combination therapy further comprising a long-acting beta$_2$ agonist, wherein the long-acting beta$_2$ agonist is salmeterol or formoterol.

29. The method of claim 23, wherein the second therapeutic agent comprises a fluticasone/salmeterol combination therapy.

30. The method of claim 23, wherein the second therapeutic agent comprises a budesonide/formoterol combination therapy.

31. The method of claim 23, wherein a second therapeutic agent selected from the group consisting of a nasal saline, a topical decongestant, a topical anesthetic, a leukotriene antagonist, and a systemic antihistamine is administered to the subject before, after, or concurrent with the antibody.

32. The method of claim 21, wherein the antibody is administered using an autoinjector, a prefilled syringe, or a prefilled pen.

* * * * *